US005869313A

United States Patent [19]
Reitz, Jr. et al.

[11] Patent Number: 5,869,313
[45] Date of Patent: Feb. 9, 1999

[54] MOLECULAR CLONES OF HIV-1 VIRAL STRAINS MN-ST1 AND BA-L, AND USES THEREOF

[75] Inventors: Marvin S. Reitz, Jr., Derwood, Md.; Genoveffa Franchini, Washington, D.C.; Phillip D. Markham, Rockville, Md.; Robert C. Gallo, Bethesda, Md.; Franco C. Lori, Bethesda, Md.; Mikulas Popovic, Bethesda, Md.; Suzanne Gartner, N. Potomac, Md.

[73] Assignee: The United States of America as represented by the Department of Health and Human Services, Washington, D.C.

[21] Appl. No.: 647,714

[22] Filed: May 14, 1996

Related U.S. Application Data

[62] Division of Ser. No. 388,809, Feb. 15, 1995, Pat. No. 5,576,000, which is a division of Ser. No. 22,835, Feb. 25, 1993, Pat. No. 5,420,030, which is a continuation of Ser. No. 599,491, Oct. 17, 1990, abandoned.

[51] Int. Cl.$^6$ ...................................................... C12N 7/00
[52] U.S. Cl. .............................. 435/35.1; 435/239; 435/6; 435/69.1; 435/69.3; 536/23.72; 530/324
[58] Field of Search .................................. 435/5, 6, 69.1, 435/69.3, 235.1, 239; 530/350, 324, 395, 403; 536/23.72; 935/1

[56] References Cited

PUBLICATIONS

A. Aldovini and R. Young, 1990, "Mutations of RNA and Protein sequences involved in human immunodeficiency virus type 1 packaging results in production of noninfectious virus", *J. Immunol.,* 64:1920–1926.

M. Alizon et., 1984, "Molecular cloning of lymphadenopathy-associated virus", *Nature,* 312:757–760.

S. Chakrabarti et al., 1986, "Expression of the HTLV–III envelope gene by a recombinant vaccinia virus", *Nature,* 320:535–537.

T.W. Chang et al., 1985, "Detection of antibodies to human T–cell lymphotropic virus–III (HTLV–III) with an immunoassay employing a recombinant *Escherichia coli*–derived viral antigenic peptide", *Biotechnology,* 3:905–909.

P.J. Dillon et al., 1990, "Function of the human immunodeficiency virus types 1 and 2 Rev proteins is dependent on their ability to interact with a structured region present in env gene mRNA", *J. Virol.,* 64:4428–4437.

C. Gurgo et al., 1988, "Envelope sequences of two United States HIV–1 isolates", *Virology,* 164:531–536.

M. Hadzopoulo–Cladaras et al., 1989, "The rev (trs/art) protein of human immunodeficiency virus type 1 affects viral mRNA and protein expression via a cis–acting sequence in the env region", *J. Virol.,* 63:1265–1274.

S–L. Hu et al., 1986, "Expression of AIDS virus envelope gene in recombinant vaccinia virus", *Nature,* 320:537–540.

W.C. Koff and D.F. Hoth, 1988, "Development and testing of AIDS vaccines", *Science,* 241:426–432.

P.A. Luciw et al., 1984, "Molecular cloning of AIDS–associated retrovirus", *Nature,* 312:760–763.

S. Modrow et al., 1987, "Computer–assisted analysis of envelope protein sequences of seven human immunodeficiency virus isolates: Prediction of antigenic epitopes in conserved and variable regions", *J. Virol.,* 61:570–578.

M.A. Muesing et al., 1985, "Nucleic acid structure and expression of the human AIDS/lymphadenopathy retrovirus", *Nature,* 313:450–458.

D. Pauletti et al., 1985 "Application of a modified computer algorithm in determining potential antigenic determinants associated with the AIDS virus glycoprotein", *Anal. Biochem.,* 151:540–546.

L. Ratner et al., 1985, "Complete nucleotide sequence of the AIDS virus, HTLV–III" *Nature,* 313:277–284.

H. Rubsamen–Waigmann et al., 1986, "Isolation of variants of lymphocytopathic retroviruses from the peripheral blood and cerebrospinal fluid of patients with ARC or AIDS", *J. Med. Virology,* 19:335–344.

J.R. Rusche et al., 1987, "Humoral immune response to the entire human immunodeficiency virus envelope glycoprotein made in insect cells", *Proc. Natl. Acad. Sci. USA,* 84:6924–6928.

R. Sanchez–Pescador et al., 1985, "Nucleotide sequence and expression of an AIDS–associated retrovirus (ARV–2)", *Science,* 227:484–492.

G.M. Shaw et al., 1984, "Molecular characterization of T–cell leukemia (lymphotropic) virus type III in the acquired immune deficiency syndrome", *Science,* 226;1165–1171.

B.R. Starich et al., 1986, "Identification and characterization of conserved and variable regions in the envelope gene of HTLV–III/LAV, the retrovirus of AIDS", *Cell,* 45:637–648.

S. Wain–Hobson et al., 1985, "Nucleotide sequence of the AIDS virus, LAV", *Cell,* 40:9–17.

Primary Examiner—Donald E. Adams
Assistant Examiner—Jeffrey Stucker
Attorney, Agent, or Firm—Morgan & Finnegan, L.L.P.

[57] ABSTRACT

The present invention relates to the HIV-1 strains MN-ST1 and BA-L which are typical United States HIV-1 isotypes. The present invention relates to DNA segments encoding the envelope protein of MN-ST1 or BA-L, to DNA constructs containing such DNA segments and to host cells transformed with such constructs. The viral isolates and envelope proteins of the present invention are of value for use in vaccines and bioassays for the detection of HIV-1 infection in biological samples, such as blood bank samples.

14 Claims, 54 Drawing Sheets

Figure 2A

```
         10         20         30         40         50         60
TGGAAGGGCT AATTCACTCC CAACGAAGAC AAGATATCCT TGATCTGTGG ATCTACCACA 70         80         90        100        110        120
CACAAGGCTA CTTCCCTGAT TAGCAGAACT ACACACCAGG GCCAGGGATC AGATATCCAC 130        140        150        160        170        180
TGACCTTTGG ATGGTGCTAC AAGCTAGTAC CAGTTGAGCC AGAGAAGTTA GAAGAAGCCA 190        200        210        220        230        240
ACAAAGGAGA GAACACCAGC TTGTTACACC CTGTGAGCCT GCATGGAATG GATGACCCGG 250        260        270        280        290        300
AGAGAGAAGT GTTAGAGTGG AGGTTTGACA GCCGCCTAGC ATTTCATCAC ATGGCCCGAG 310        320        330        340        350        360
AGCTGCATCC GGAGTACTTC AAGAACTGCT GACATCGAGC TTGCTACAAG GGACTTTCCG 370        380        390        400        410        420
CTGGGGACTT TCCAGGGAGG CGTGGCCTGG GCGGGACTGG GGAGTGGCGA GCCCTCAGAT 430        440        450        460        470        480
CCTGCATATA AGCAGCTGCT TTTTGCCTGT ACTGGGTCTC TCTGGTTAGA CCAGATCTGA 490        500        510        520        530        540
GCCTGGGAGC TCTCTGGCTA ACTAGGGAAC CCACTGCTTA AGCCTCAATA AAGCTTGCCT 550        560        570        580        590        600
TGAGTGCTTC AAGTAGTGTG TGCCCGTCTG TTATGTGACT CTGGTAGCTA GAGATCCCTC 610        620        630        640        650        660
AGATCCTTTT AGGCAGTGTG GAAAATCTCT AGCAGTGGCG CCCGAACAGG GACTTGAAAG 670        680        690        700        710        720
CGAAAGAAAA ACCAGAGCTC TCTCGACGCA GGACTCGGCT TGCTGAAGCG CGCACGGCAA 730        740        750        760        770        780
GAGGCGAGGG GCGGCGACTG GTGAGTACGC CAAAAATTCT TGACTAGCGG AGGCTAGAAG 790        800        810        820        830        840
GAGAGAGATG GGTGCGAGAG CGTCGGTATT AAGCGGGGGA GAATTAGATC GATGGGAAAA 850        860        870        880        890        900
CATTCGGTTA AGGCCAGGGG GAAAGAAAAA ATATAAATTA AAACATGTAG TATGGGCAAG 910        920        930        940        950        960
CAGGGAGCTA GAACGATTCG CAGTCAATCC TGGCCTGTTA GAAACATCAG AAGGCTGTAG 970        980        990       1000       1010       1020
ACAAATACTG GGACAGCTAC AACCATCCCT TCAGACAGGA TCAGAAGAAC TTAAATCATT 1030       1040       1050       1060       1070       1080
ATATAATACA GTAGCAACCC TCTATTGTGT GCATCAAAAG ATAGAGATAA AAGACACCAA 1090       1100       1110       1120       1130       1140
GGAAGCTTTA GAGAAAATAG AGGAAGAGCA AAACAAAAGT AAGAAAAAAG CACAGCAAGC 1150       1160       1170       1180       1190       1200
AGCAGCTGAC ACAGGAAACA GAGGAAACAG CAGCCAAGTC AGCCAAAATT ACCCCATAGT 1210       1220       1230       1240       1250       1260
GCAGAACATC GAGGGGCAAA TGGTACATCA GGCCATATCA CCTAGAACTT TAAATGCATG
```

Figure 2B

```
          1270       1280       1290       1300       1310       1320
     GGTAAAAGTA GTAGAAGAGA AGGCTTTCAG CCCAGAAGTA ATACCCATGT TTTCAGCATT
          1330       1340       1350       1360       1370       1380
     ATCAGAAGGA GCCACCCCAC AAGATTTAAA CACCATGCTA AACACAGTGG GGGACATCA
          1390       1400       1410       1420       1430       1440
     AGCAGCCATG CAAATGTTAA AAGAGACCAT CAATGAGGAA GCTGCAGAAT GGGATAGATT
          1450       1460       1470       1480       1490       1500
     GCATCCAGTG CATGCAGGGC CTATTACACC AGGCCAGATG AGAGAACCAA GGGGAAGTGA
          1510       1520       1530       1540       1550       1560
     CATAGCAGGA ACTACTAGTA CCCTTCAGGA ACAAATAGGA TGGATGACAA ATAATCCACC
          1570       1580       1590       1600       1610       1620
     TATCCCAGTA GGAGAAATCT ATAAAAGATG GATAATCCTG GGATTAAATA AAATAGTAAG
          1630       1640       1650       1660       1670       1680
     GATGTATAGC CCTTCCAGCA TTCTGGACAT AAGACAAGGA CCAAAGGAAC CCTTTAGAGA
          1690       1700       1710       1720       1730       1740
     CTATGTAGAC CGGTTCTATA AAACTCTAAG AGCCGAGCAA GCTTCACAGG AGGTAAAAAA
          1750       1760       1770       1780       1790       1800
     CCGGACGACA GAAACCTTGT TGGTCCAAAA TGCGAACCCA GATTGTAAGA CTATTTTAAA
          1810       1820       1830       1840       1850       1860
     AGCATTGGGA CCAGCAGCTA CACTAGAAGA AATGATGACA GCATGTCAGG GAGTGGGAGG
          1870       1880       1890       1900       1910       1920
     ACCTGGTCAT AAAGCAAGAG TTTTGGCGGA AGCGATGAGC CAAGTAACAA ATTCAGCTAC
          1930       1940       1950       1960       1970       1980
     CATAATGATG CAGAGAGGCA ATTTTAGGAA TCAAAGAAAG ATTATCAAGT GCTTCAATTG
          1990       2000       2010       2020       2030       2040
     TGGCAAAGAA GGGCACATAG CCAAAAATTG CAGGGCCCCT AGGAAAAGGG GCTGTTGGAA
          2050       2060       2070       2080       2090       2100
     ATGTGGAAAG GAAGGACACC AAATGAAAGA TTGTACTGAG AGACAGGCTA ATTTTTTAGG
          2110       2120       2130       2140       2150       2160
     GAAGATCTGG CCTTCCTGCA AGGGAAGGCG GAATTTTCCT CAGAGCAGAA CAGAGCCAAC
          2170       2180       2190       2200       2210       2220
     AGCCCCACCA GAAGAGAGCT TCAGGTTTGG GGAAGAGACA ACAACTCCCT ATCAGAAGCA
          2230       2240       2250       2260       2270       2280
     GGAGAAGAAG CAGGAGACGA TAGACAAGGA CCTGTATCCT TTAGCTTCCC TCAAATCACT
          2290       2300       2310       2320       2330       2340
     CTTTGGCAAC GACCCATTGT CACAATAAAG ATAGGGGGC AACTAAAGGA AGCTCTATTA
          2350       2360       2370       2380       2390       2400
     GATACAGGAG CAGATGATAC AGTATTAGGA GAAATGAATT TGCCAAGAAG ATGGAAACCA
          2410       2420       2430       2440       2450       2460
     AAAATGATAG GGGGAATTGG AGGTTTTATC AAAGTAAGAC AGTATGATCA GATAACCATA
          2470       2480       2490       2500       2510       2520
     GGAATCTGTG GACATAAAGC TATAGGTACA GTATTAGTAG GACCTACACC TGTCAACATA
```

Figure 2C

```
           2530       2540       2550       2560       2570       2580
      ATTGGAAGAA ATCTGTTGAC TCAGCTTGGG TGCACTTTAA ATTTTCCCAT TAGTCCTATT 2590       2600       2610       2620       2630       2640
      GAAACTGTAC CAGTAAAATT AAAGCCAGGA ATGGATGGCC CAAAAGTTAA ACAATGGCCA 2650       2660       2670       2680       2690       2700
      TTGACAGAAG AAAAAATAAA AGCATTAATA GAAATTTGTA CAGAAATGGA AAAGGAAGGG 2710       2720       2730       2740       2750       2760
      AAAATTTCAA AAATTGGGCC TGAAAATCCA TACAATACTC CAGTATTTGC CATAAAGAAA 2770       2780       2790       2800       2810       2820
      AAAGACAGTA CTAAATGGAG AAAATTAGTA GATTTCAGAG AACTTAATAA GAAAACTCAA 2830       2840       2850       2860       2870       2880
      GACTTCTGGG AAGTTCAATT AGGAATACCA CATCCTGCAG GGTTAAAAAA GAAAAAATCA 2890       2900       2910       2920       2930       2940
      GTAACAGTAC TGGATGTGGG TGATGCATAT TTTTCAGTTC CCTTAGATAA AGACTTCAGG 2950       2960       2970       2980       2990       3000
      AAGTATACTG CATTTACCAT ACCTAGTATA AACAATGAAA CACCAGGGAT TAGATATCAG 3010       3020       3030       3040       3050       3060
      TACAATGTGC TTCCACAGGG ATGGAAAGGA TCACCAGCAA TATTCCAAAG TAGCATGACA 3070       3080       3090       3100       3110       3120
      AAAATCTTAG AGCCTTTTAG AAAACAAAAT CCAGACATAG TTATCTATCA ATACATGGAT 3130       3140       3150       3160       3170       3180
      GATTTGTATG TAGGATCTGA CTTAGAAATA GGGCAGCATA GAGCAAAAAT AGAGGAACTG 3190       3200       3210       3220       3230       3240
      AGACGACATC TGTTGAGGTG GGGATTTACC ACACCAGACA AAAAACATCA GAAAGAACCT 3250       3260       3270       3280       3290       3300
      CCATTCCTTT GGATGGGTTA TGAACTCCAT CCTGATAAAT GGACAGTACA GCCTATAGTG 3310       3320       3330       3340       3350       3360
      CTACCAGAAA AAGACAGCTG GACTGTCAAT GACATACAGA AGTTAGTGGG AAAATTGAAT 3370       3380       3390       3400       3410       3420
      TGGGCAAGTC AGATTTACGC AGGGATTAAA GTAAAGCAAT TATGTAAACT CCTTAGAGGA 3430       3440       3450       3460       3470       3480
      ACCAAAGCAC TAACAGAAGT AATACCACTA ACAGAAGAAG CAGAGCTAGA ACTGGCAGAA 3490       3500       3510       3520       3530       3540
      AACAGGGAAA TTCTAAAAGA ACCAGTACAT GGAGTGTATT ATGACCCATC AAAAGACTTA 3550       3560       3570       3580       3590       3600
      ATAGCAGAAG TACAGAAGCA GGGGCAAGGC CAATGGACAT ATCAAATTTA TCAAGAGCCA 3610       3620       3630       3640       3650       3660
      TTTAAAAATC TGAAAACAGG CAAATATGCA AGAATGAGGG GTGCCCACAC TAATGATGTA 3670       3680       3690       3700       3710       3720
      AAACAATTAA CAGAGGCAGT GCAAAAAATA GCCACAGAAA GCATAGTAAT ATGGGGAAAG 3730       3740       3750       3760       3770       3780
      ACTCCTAAAT TTAGACTACC CATACAAAAA GAAACATGGG AAACATGGTG GACAGAGTAT
```

Figure 2D

```
          3790       3800       3810       3820       3830       3840
     ACGTAAGCCA CCTGGATTCC TGAGTGGGAG GTTGTCAATA CCCCTCCCTT AGTGAAATTA 3850       3860       3870       3880       3890       3900
     TGGTACCAGT TAGAGAAAGA ACCCATAGTA GGTGCAGAAA CTTTCTATGT AGATGGGGCA 3910       3920       3930       3940       3950       3960
     GCTAACAGGG AGACTAAAAA AGGAAAAGCA GGATATGTTA CTAACAGAGG AAGACAAAAG 3970       3980       3990       4000       4010       4020
     GTTGTCTCCC TAACTGACAC AACAAATCAG AAGACTGAGT TACAAGCAAT TCATCTAGCT 4030       4040       4050       4060       4070       4080
     TTGCAAGATT CAGGGTTAGA AGTAAACATA GTAACAGACT CACAATATGC ATTAGGAATC 4090       4100       4110       4120       4130       4140
     ATTCAAGCAC AACCAGATAA AAGTGAATCA GAGTTAGTCA GTCAAATAAT AGAGCAGTTA 4150       4160       4170       4180       4190       4200
     ATAAAAAAGG AAAAGGTCTA TCTGGCATGG GTACCAGCAC ACAAAGGAAT TGGAGGAAAT 4210       4220       4230       4240       4250       4260
     GAACAAGTAG ATAAATTAGT CAGTGCTGGA ATCAGGAAAG TACTATTTTT AGATGGAATA 4270       4280       4290       4300       4310       4320
     GATAAGGCCC AAGAAGACCA TGAGAAATAT CACAGTAATT GGAGAGCAAT GGCTAGTGAC 4330       4340       4350       4360       4370       4380
     TTTAACCTAC CACCTATAGT AGCAAAAGAA ATAGTAGCCA GCTGTGATAA ATGTCAGCTA 4390       4400       4410       4420       4430       4440
     AAAGGAGAAG CCATGCATGG ACAAGTAGAC TGTAGTCCAG GAATATGGCA ACTAGATTGT 4450       4460       4470       4480       4490       4500
     ACACATTTAG AAGGAAAAGT TATCCTGGTA GCAGTTCATG TAGCCAGTGG ATACATAGAA 4510       4520       4530       4540       4550       4560
     GCAGAAGTTA TTCCAGCAGA GACAGGGCAG GAGACAGCAT ACTTTCTCTT AAAATTAGCA 4570       4580       4590       4600       4610       4620
     GGAAGATGGC CAGTAAAAAC AATACATACA GACAATGGCC CCAATTTCAC CAGTACTACG 4630       4640       4650       4660       4670       4680
     GTTAAGGCCG CCTGTTGGTG GACGGGAATC AAGCAGGAAT TTGGCATTCC CTACAATCCC 4690       4700       4710       4720       4730       4740
     CAAAGTCAAG GAGTAATAGA ATCTATGAAT AAAGAATTAA AGAAAATTAT AGGACAGGTA 4750       4760       4770       4780       4790       4800
     AGAGATCAGG CTGAACATCT TAAGAGAGCA GTACAAATGG CAGTATTCAT CCACAATTTT 4810       4820       4830       4840       4850       4860
     AAAAGAAAAG GGGGGATTGG GGGGTACAGT GCAGGGGAAA GAATAGTAGG CATAATAGCA 4870       4880       4890       4900       4910       4920
     ACAGACATAC AAACTAAAGA ACTACAAAAA CAAATTACAA AAATTCAAAA TTTTCGGGTT 4930       4940       4950       4960       4970       4980
     TATTACAGGG ACAGCAGAGA TCCACTTTGG AAAGGACCAG CAAAGCTTCT CTGGAAAGGT 4990       5000       5010       5020       5030       5040
     GAAGGGGCAG TAGTAATACA AGATAATAAT GACATAAAAG TAGTGCCAAG AAGAAAAGCA
```

Figure 2E

```
        5050       5060       5070       5080       5090       5100
   AAGGTCATTA GGGATTATGG AAAACAGACG GCAGGTGATG ATTGTGTGGC AAGCAGACAG 5110       5120       5130       5140       5150       5160
   GATGAGGATT AGAACATGGA AAAGTTTAGT AAAACACCAT ATGTATATTT CAAAGAAAGC 5170       5180       5190       5200       5210       5220
   TAAAGGACGG TTTTATAGAC ATCACTATGA AAGCACTCAT CCAAGAATAA GTTCAGAAGT 5230       5240       5250       5260       5270       5280
   ACACATCCCA CTAGGGGATG CTAGATTGGT AATAACAACA TATTGGGGTC TGCATACAGG 5290       5300       5310       5320       5330       5340
   AGAAAGAGAC TGGCATTTAG GTCAGGGAGT CTCCATAGAA TGGAGGAAAA AGAGATATAG 5350       5360       5370       5380       5390       5400
   CACACAAGTA GACCCTGACC TAGCAGACCA CCTAATTCAT CTGCATTACT TTGATTGTTT 5410       5420       5430       5440       5450       5460
   TTCAGACTCT GCCATAAGAA AGGCCATATT AGGACATAGA GTTAGTCCTA TTTGTGAATT 5470       5480       5490       5500       5510       5520
   TCAAGCAGGA CATAACAAGG TAGGACCTCT ACAGTACTTG GCACTAACAG CATTAATAAC 5530       5540       5550       5560       5570       5580
   ACCAAAAAAG ATAAAGCCAC CTTTGCCTAG TGTTAAGAAA CTGACAGAGG ATAGATGGAA 5590       5600       5610       5620       5630       5640
   CAAGCCCCAG AAGACCAAGG GCCACAGAGG GAGCCATACA ATCAATGGGC ACTAGAGCTT 5650       5660       5670       5680       5690       5700
   TTAGAGGAGC TTAAGAATGA AGCTGTTAGA CATTTTCCTA GGATATGGCT CCATGGCTTA 5710       5720       5730       5740       5750       5760
   GGGCAACATA TCTATGAAAC TTATGGGGAT ACTTGGGCAG GAGTGGAAGC CATAATAAGA 5770       5780       5790       5800       5810       5820
   ATTCTACAAC AACTGCTGTT TATTCATTTC AGAATTGGGT GTCGACATAG CAGAATAGGC 5830       5840       5850       5860       5870       5880
   ATTATTCGAC AGAGGAGAGC AAGAAATGGA GCCAGTAGAT CCTAGACTAG AGCCCTGGAA 5890       5900       5910       5920       5930       5940
   GCATCCAGGA AGTCAGCCTA AGACTGCTTG TACCACTTGC TATTGTAAAA AGTGTTGCTT 5950       5960       5970       5980       5990       6000
   TCATTGCCAA GTTTGTTTCA CAAAAAAGC CTTAGGCATC TCCTATGGCA GGAAGAAGCG 6010       6020       6030       6040       6050       6060
   GAGACAGCGA CGAAGAGCTC CTGAAGACAG TCAGACTCAT CAAGTTTCTC TACCAAAGCA 6070       6080       6090       6100       6110       6120
   GTAAGTAGTA CATGTAATGC AACCTTTAGT AATAGCAGCA ATAGTAGCAT TAGTAGTAGC 6130       6140       6150       6160       6170       6180
   AGGAATAATA GCAATAGTTG TGTGATCCAT AGTATTCATA GAATATAGGA AAATAAGAAG 6190       6200       6210       6220       6230       6240
   ACAAAGAAAA ATAGACAGGT TAATTGATAG AATAAGCGAA AGAGCAGAAG ACAGTGGCAA 6250       6260       6270       6280       6290       6300
   TGAGAGTGAA GGGGATCAGG AGGAATTATC AGCACTGGTG GGGATGGGGC ACGATGCTCC
```

Figure 2F

```
           6310       6320       6330       6340       6350       6360
      TTGGGTTATT AATGATCTGT AGTGCTACAG AAAAATTGTG GGTCACAGTC TATTATGGGG 6370       6380       6390       6400       6410       6420
      TACCTGTGTG GAAAGAAGCA ACCACCACTC TATTTTGTGC ATCAGATGCT AAAGCATATG 6430       6440       6450       6460       6470       6480
      ATACAGAGGT ACATAATGTT TGGGCCACAC AAGCCTGTGT ACCCACAGAC CCCAACCCAC 6490       6500       6510       6520       6530       6540
      AAGAAGTAGA ATTGGTAAAT GTGACAGAAA ATTTTAACAT GTGGAAAAAT AACATGGTAG 6550       6560       6570       6580       6590       6600
      AACAGATGCA TGAGGATATA ATCAGTTTAT GGGATCAAAG CCTAAAGCCA TGTGTAAAAT 6610       6620       6630       6640       6650       6660
      TAACCCCACT CTGTGTTACT TTAAATTGCA CTGATTTGAG GAATACTACT AATACCAATA 6670       6680       6690       6700       6710       6720
      ATAGTACTGC TAATAACAAT AGTAATAGCG AGGGAACAAT AAAGGGAGGA GAAATGAAAA 6730       6740       6750       6760       6770       6780
      ACTGCTCTTT CAATATCACC ACAAGCATAA GAGATAAGAT GCAGAAAGAA TATGCACTTC 6790       6800       6810       6820       6830       6840
      TTTATAAACT TGATATAGTA TCAATAGATA ATGATAGTAC CAGCTATAGG TTGATAAGTT 6850       6860       6870       6880       6890       6900
      GTAATACCTC AGTCATTACA CAAGCTTGTC CAAAGATATC CTTTGAGCCA ATTCCCATAC 6910       6920       6930       6940       6950       6960
      ACTATTGTGC CCCGGCTGGT TTTGCGATTC TAAAATGTAA CGATAAAAAG TTCAGTGGAA 6970       6980       6990       7000       7010       7020
      AAGGATCATG TAAAAATGTC AGCACAGTAC AATGTACACA TGGAATTAGG CCAGTAGTAT 7030       7040       7050       7060       7070       7080
      CAACTCAACT GCTGTTAAAT GGCAGTCTAG CAGAAGAAGA GGTAGTAATT AGATCTGAGA 7090       7100       7110       7120       7130       7140
      ATTTCACTGA TAATGCTAAA ACCATCATAG TACATCTGAA TGAATCTGTA CAAATTAATT 7150       7160       7170       7180       7190       7200
      GTACAAGACC CAACTACAAT AAAAGAAAAA GGATACATAT AGGACCAGGG AGAGCATTTT 7210       7220       7230       7240       7250       7260
      ATACAACAAA AAATATAATA GGAACTATAA GACAAGCACA TTGTAACATT AGTAGAGCAA 7270       7280       7290       7300       7310       7320
      AATGGAATGA CACTTTAAGA CAGATAGTTA GCAAATTAAA AGAACAATTT AAGAATAAAA 7330       7340       7350       7360       7370       7380
      CAATAGTCTT TAATCAATCC TCAGGAGGGG ACCCAGAAAT TGTAATGCAC AGTTTTAATT 7390       7400       7410       7420       7430       7440
      GTGGAGGGGA ATTTTTCTAC TGTAATACAT CACCACTGTT TAATAGTACT TGGAATGGTA 7450       7460       7470       7480       7490       7500
      ATAATACTTG GAATAATACT ACAGGGTCAA ATAACAATAT CACACTTCAA TGCAAAATAA 7510       7520       7530       7540       7550       7560
      AACAAATTAT AAACATGTGG CAGGAAGTAG GAAAAGCAAT GTATGCCCCT CCCATTGAAG
```

Figure 2G

```
          7570       7580       7590       7600       7610       7620
    GACAAATTAG ATGTTCATCA AATATTACAG GGCTACTATT AACAAGAGAT GGTGGTAAGG
          7630       7640       7650       7660       7670       7680
    ACACGGACAC GAACGACACC GAGATCTTCA GACCTGGAGG AGGAGATATG AGGGACAATT
          7690       7700       7710       7720       7730       7740
    GGAGAAGTGA ATTATATAAA TATAAAGTAG TAACAATTGA ACCATTAGGA GTAGCACCCA
          7750       7760       7770       7780       7790       7800
    CCAAGGCAAA GAGAAGAGTG GTGCAGAGAG AAAAAAGAGC AGCGATAGGA GCTCTGTTCC
          7810       7820       7830       7840       7850       7860
    TTGGGTTCTT AGGAGCAGCA GGAAGCACTA TGGGCGCAGC GTCAGTGACG CTGACGGTAC
          7870       7880       7890       7900       7910       7920
    AGGCCAGACT ATTATTGTCT GGTATAGTGC AACAGCAGAA CAATTTGCTG AGGGCCATTG
          7930       7940       7950       7960       7970       7980
    AGGCGCAACA GCATATGTTG CAACTCACAG TCTGGGGCAT CAAGCAGCTC CAGGCAAGAG
          7990       8000       8010       8020       8030       8040
    TCCTGGCTGT GGAAAGATAC CTAAAGGATC AACAGCTCCT GGGGTTTTGG GGTTGCTCTG
          8050       8060       8070       8080       8090       8100
    GAAAACTCAT TTGCACCACT ACTGTGCCTT GGAATGCTAG TTGGAGTAAT AAATCTCTGG
          8110       8120       8130       8140       8150       8160
    ATGATATTTG GAATAACATG ACCTGGATGC AGTGGGAAAG AGAAATTGAC AATTACACAA
          8170       8180       8190       8200       8210       8220
    GCTTAATATA CTCATTACTA GAAAAATCGC AAACCCAACA AGAAAAGAAT GAACAAGAAT
          8230       8240       8250       8260       8270       8280
    TATTGGAATT GGATAAATGG GCAAGTTTGT GGAATTGGTT TGACATAACA AATTGGCTGT
          8290       8300       8310       8320       8330       8340
    GGTATATAAA AATATTCATA ATGATAGTAG GAGGCTTGGT AGGTTTAAGA ATAGTTTTTG
          8350       8360       8370       8380       8390       8400
    CTGTACTTTC TATAGTGAAT AGAGTTAGGC AGGGATACTC ACCATTGTCG TTGCAGACCC
          8410       8420       8430       8440       8450       8460
    GCCCCCCAGT TCCGAGGGGA CCCGACAGGC CCGAAGGAAT CGAAGAAGAA GGTGGAGAGA
          8470       8480       8490       8500       8510       8520
    GAGACAGAGA CACATCCGGT CGATTAGTGC ATGGATTCTT AGCAATTATC TGGGTCGACC
          8530       8540       8550       8560       8570       8580
    TGCGGAGCCT GTTCCTCTTC AGCTACCACC ACAGAGACTT ACTCTTGATT GCAGCGAGGA
          8590       8600       8610       8620       8630       8640
    TTGTGGAACT TCTGGGACGC AGGGGGTGGG AAGTCCTCAA ATATTGGTGG AATCTCCTAC
          8650       8660       8670       8680       8690       8700
    AGTATTGGAG TCAGGAACTA*AAGAGTAGTG CTGTTAGCTT GCTTAATGCC ACAGCTATAG
          8710       8720       8730       8740       8750       8760
    CAGTAGCTGA GGGGACAGAT AGGGTTATAG AAGTACTGCA AAGAGCTGGT AGAGCTATTC
          8770       8780       8790       8800       8810       8820
    TCCACATACC TACAAGAATA AGACAGGGCT TGGAAAGGGC TTTGCTATAA GATGGGTGGC
```

Figure 2H

```
          8830       8840       8850       8860       8870       8880
    AAATGGTCAA AACGTGTGAC TGGATGGCCT ACTGTAAGGG AAAGAATGAG ACGAGCTGAA 8890       8900       8910       8920       8930       8940
    CCAGCTGAGC TAGCAGCAGA TGGGGTGGGA GCAGCATCCC GAGACCTGGA AAAACATGGA 8950       8960       8970       8980       8990       9000
    GCACTCACAA GTAGCAATAC AGCAGCTACC AATGCTGATT GTGCCTGGCT AGAAGCACAA 9010       9020       9030       9040       9050       9060
    GAGGAGGAGG AAGTGGGTTT TCCAGTCAAA CCTCAGGTAC CTTTAAGACC AATGACTTAC 9070       9080       9090       9100       9110       9120
    AAAGCAGCTT TAGATCTTAG CCACTTTTTA AAAGAAAAGG GGGGACTGGA TGGGTTAATT 9130       9140       9150       9160       9170       9180
    TACTCCCAAA AGAGACAAGA CATCCTTGAT CTGTGGGTCT ACCACACACA AGGCTACTTC 9190       9200       9210       9220       9230       9240
    CCTGATTGGC AGAACTACAC ACCAGGGCCA GGGATCAGAT ATCCACTGAC CTTTGGATGG 9250       9260       9270       9280       9290       9300
    TGCTTCAAGC TAGTACCAGT TGAGCCAGAG AAGATAGAAG AGGCCAATAA AGGAGAGAAC 9310       9320       9330       9340       9350       9360
    AACTGCTTGT TACACCCTAT GAGCCAGCAT GGATGGATGA CCCGGAGAGA GAAGTGTTAG 9370       9380       9390       9400       9410       9420
    TGTGGAAGTC TGACAGCCAC CTAGCATTTC AGCATTATGC CCGAGAGCTG CATCCGGAGT 9430       9440       9450       9460       9470       9480
    ACTACAAGAA CTGCTGACAT CGAGCTATCT ACAAGGGACT TTCCGCTGGG GACTTTCCAG 9490       9500       9510       9520       9530       9540
    GGAGGTGTGG CCTGGGCGGG ACCGGGGAGT GGCGAGCCCT CAGATCGTGC ATATAAGCAG 9550       9560       9570       9580       9590       9600
    CTGCTTTCTG CCTGTACTGG GTCTCTCTGG TTAGACCAGA TCTGAGCCTG GGAGCTCTCT 9610       9620       9630       9640       9650       9660
    GGCTAACTAG GGAACCCACT GCTTAAGCCT CAATAAAGCT TGCCTTGAGT GCTTCAAGTA 9670       9680       9690       9700       9710       9720
    GTGTGTGCCC GTCTGTTATG TGACTCTGGT AGCTAGAGAT CCCTCAGATC CTTTTAGGCA

9730
    GTGTGGAAAA TCTCTAGCA
```

```
           10        20        30        40        50        60
TGGATGGGTTAATTTACTCCCAAAGAGACAAGACATCCTTGATCTGTGGGTCTACCACAC
 W  M  G  *  F  T  P  K  E  T  R  H  P  *  S  V  G  L  P  H
  G  W  V  N  L  L  P  K  R  Q  D  I  L  D  L  W  V  Y  H  T
   D  G  L  I  Y  S  Q  R  D  K  T  S  L  I  C  G  S  T  T 70        80        90       100       110       120
ACAAGGCTACTTCCCTGATTGGCAGAACTACACACCAGGGCCAGGGATCAGATATCCACT
 T  R  L  L  P  *  L  A  E  L  H  T  R  A  R  D  Q  I  S  T
  Q  G  Y  F  P  D  W  Q  N  Y  T  P  G  P  G  I  R  Y  P  L
   H  K  A  T  S  L  I  G  R  T  T  H  Q  G  Q  G  S  D  I  H 130       140       150       160       170       180
GACCTTTGGATGGTGCTTCAAGCTAGTACCAGTTGAGCCAGAGAAGATAGAAGAGGCCAA
 D  L  W  M  V  L  Q  A  S  T  S  *  A  R  E  D  R  R  G  Q
  T  F  G  W  C  F  K  L  V  P  V  E  P  E  K  I  E  E  A  N
   *  P  L  D  G  A  S  S  *  Y  Q  L  S  Q  R  R  *  K  R  P 190       200       210       220       230       240
TAAAGGAGAGAACAACTGCTTGTTACACCCTATGAGCCAGCATGGGATGGATGACCCGGA
 *  R  R  E  Q  L  L  V  T  P  Y  E  P  A  W  D  G  *  P  G
  K  G  E  N  N  C  L  L  H  P  M  S  Q  H  G  M  D  D  P  E
   I  K  E  R  T  T  A  C  Y  T  L  *  A  S  M  G  W  M  T  R 250       260       270       280       290       300
GAGAGAAGTGTTAGTGTGGAAGTCTGACAGCCACCTAGCATTTCAGCATTATGCCCGAGA
 E  R  S  V  S  V  E  V  *  Q  P  P  S  I  S  A  L  C  P  R
  R  E  V  L  V  W  K  S  D  S  H  L  A  F  Q  H  Y  A  R  E
   R  E  K  C  *  C  G  S  L  T  A  T  *  H  F  S  I  M  P  E 310       320       330       340       350       360
GCTGCATCCGGAGTACTACAAGAACTGCTGACATCGAGCTATCTACAAGGGACTTTCCGC
 A  A  S  G  V  L  Q  E  L  L  T  S  S  Y  L  Q  G  T  F  R
  L  H  P  E  Y  Y  K  N  C  *  H  R  A  I  Y  K  G  L  S  A
   S  C  I  R  S  T  T  R  T  A  D  I  E  L  S  T  R  D  F  P 370       380       390       400       410       420
TGGGGACTTTCCAGGGAGGTGTGGCCTGGGCGGGACCGGGGAGTGGCGAGCCCTCAGATG
 W  G  L  S  R  E  V  W  P  G  R  D  R  G  V  A  S  P  Q  M
  G  D  F  P  G  R  C  G  L  G  G  T  G  E  W  R  A  L  R  C
   L  G  T  F  Q  G  G  V  A  W  A  G  P  G  S  G  E  P  S  D 430       440       450       460       470       480
CTGCATATAAGCAGCTGCTTTCTGCCTGTACTGGGTCTCTCTGGTTAGACCAGATCTGAG
 L  H  I  S  S  C  F  L  P  V  L  G  L  S  G  *  T  R  S  E
  C  I  *  A  A  A  F  C  L  Y  W  V  S  L  V  R  P  D  L  S
   A  A  Y  K  Q  L  L  S  A  C  T  G  S  L  W  L  D  Q  I  *

490       500       510       520       530       540
CCTGGGAGCTCTCTGGCTAACTAGGGAACCCACTGCTTAAGCCTCAATAAAGCTTGCCTT
 P  G  S  S  L  A  N  *  G  T  H  C  L  S  L  N  K  A  C  L
  L  G  A  L  W  L  T  R  E  P  T  A  *  A  S  I  K  L  A  L
   A  W  E  L  S  G  *  L  G  N  P  L  L  K  P  Q  *  S  L  P
```

Figure 6B

```
            550       560       570       580       590       600
     GAGTGCTTCAAGTAGTGTGTGCCCGTCTGTTATGTGACTCTGGTAGCTAGAGATCCCTCA
      E  C  F  K  *  C  V  P  V  C  Y  V  T  L  V  A  R  D  P  S
       S  A  S  S  S  V  C  P  S  V  M  *  L  W  *  L  E  I  P  Q
      *  V  L  Q  V  V  C  A  R  L  L  C  D  S  G  S  *  R  S  L 610       620       630       640       650       660
     GATCCTTTTAGGCAGTGTGGAAAATCTCTAGCAGTGGCGCCCGAACAGGGACTTGAAAGC
      D  P  F  R  Q  C  G  K  S  L  A  V  A  P  E  Q  G  L  E  S
       I  L  L  G  S  V  E  N  L  *  Q  W  R  P  N  R  D  L  K  A
      R  S  F  *  A  V  W  K  I  S  S  S  G  A  R  T  G  T  *  K 670       680       690       700       710       720
     GAAAGAGAAACCAGAGGAGCTCTCTCGACGCAGGACTCGGCTTGCTGAAGCGCGCACGGC
      E  R  E  T  R  G  A  L  S  T  Q  D  S  A  C  *  S  A  H  G
       K  E  K  P  E  E  L  S  R  R  R  T  R  L  A  E  A  R  T  A
      R  K  R  N  Q  R  S  S  L  D  A  G  L  G  L  L  K  R  A  R 730       740       750       760       770       780
     AAGAGGCGAGGGGCGGCGACTGGTGAGTACGCCAAAATTCTTGACTAGCGGAGGCTAGAA
      K  R  R  G  A  A  T  G  E  Y  A  K  I  L  D  *  R  R  L  E
       R  G  E  G  R  R  L  V  S  T  P  K  F  L  T  S  G  G  *  K
      Q  E  A  R  G  G  D  W  *  V  R  Q  N  S  *  L  A  E  A  R 790       800       810       820       830       840
     GGAGAGAGATGGGTGCGAGAGCGTCGGTATTAAGCGGGGGAGAATTAGATCGATGGGAAA
      G  E  R  W  V  R  E  R  R  Y  *  A  G  E  N  *  I  D  G  K
       E  R  D  G  C  E  S  V  G  I  K  R  G  R  I  R  S  M  G  K
      R  R  E  M  G  A  R  A  S  V  L  S  G  G  E  L  D  R  W  E 850       860       870       880       890       900
     AAATTCGGTTAAGGCCAGGGGGAAAGAAAAAATATAAATTAAAACATGTAGTATGGGCAA
      K  F  G  *  G  Q  G  E  R  K  N  I  N  *  N  M  *  Y  G  Q
       N  S  V  K  A  R  G  K  E  K  I  *  I  K  T  C  S  M  G  K
      K  I  R  L  R  P  G  G  K  K  K  Y  K  L  K  H  V  V  W  A 910       920       930       940       950       960
     GCAGGGAGCTAGAACGATTCGCAGTCAATCCTGGCCTGTTAGAAACATCAGAAGGCTGTA
      A  G  S  *  N  D  S  Q  S  I  L  A  C  *  K  H  Q  K  A  V
       Q  G  A  R  T  I  R  S  Q  S  W  P  V  R  N  I  R  R  L  *
      S  R  E  L  E  R  F  A  V  N  P  G  L  L  E  T  S  E  G  C 970       980       990      1000      1010      1020
     GACAAATACTGGGACAGCTACAACCATCCCTTCAGACAGGATCAGAAGAACTTAAATCAT
      D  K  Y  W  D  S  Y  N  H  P  F  R  Q  D  Q  K  N  L  N  H
       T  N  T  G  T  A  T  T  I  P  S  D  R  I  R  R  T  *  I  I
      R  Q  I  L  G  Q  L  Q  P  S  L  Q  T  G  S  E  E  L  K  S 1030      1040      1050      1060      1070      1080
     TATATAATACAGTAGCAACCCTCTATTGTGTGCATCAAAAGATAGAGATAAAAGACACCA
      Y  I  I  Q  *  Q  P  S  I  V  C  I  K  R  *  R  *  K  T  P
       I  *  Y  S  S  N  P  L  L  C  A  S  K  D  R  D  K  R  H  Q
      L  Y  N  T  V  A  T  L  Y  C  V  H  Q  K  I  E  I  K  D  T
```

Figure 6C

```
        1090      1100      1110      1120      1130      1140
AGGAAGCTTTAGAGAAAATAGAGGAAGAGCAAAACAAAAGTAAGAAAAAAGCACAGCAAG
  R  K  L  *  R  K  *  R  K  S  K  T  K  V  R  K  K  H  S  K
   G  S  F  R  E  N  R  G  R  A  K  Q  K  *  E  K  S  T  A  S
 K  E  A  L  E  K  I  E  E  E  Q  N  K  S  K  K  K  A  Q  Q 1150      1160      1170      1180      1190      1200
CAGTAGCTGACACAGGAAACAGAGGAAACAGCAGCCAAGTCAGCCAAAATTACCCCATAG
  Q  *  L  T  Q  E  T  E  E  T  A  A  K  S  A  K  I  T  P  *
   S  S  *  H  R  K  Q  R  K  Q  Q  P  S  Q  P  K  L  P  H  S
 A  V  A  D  T  G  N  R  G  N  S  S  Q  V  S  Q  N  Y  P  I 1210      1220      1230      1240      1250      1260
TGCAGAACATCCAGGGGCAAATGGTACATCAGGCCATATCACCTAGAACTTTAAATGCAT
  C  R  T  S  R  G  K  W  Y  I  R  P  Y  H  L  E  L  *  M  H
   A  E  H  P  G  A  N  G  T  S  G  H  I  T  *  N  F  K  C  M
 V  Q  N  I  Q  G  Q  M  V  H  Q  A  I  S  P  R  T  L  N  A 1270      1280      1290      1300      1310      1320
GGGTAAAAGTAGTAGAAGAGAAGGCTTTCAGCCCAGAAGTAATACCCATGTTTTCAGCAT
  G  *  K  *  *  K  R  R  L  S  A  Q  K  *  Y  P  C  F  Q  H
   G  K  S  S  R  R  E  G  F  Q  P  R  S  N  T  H  V  F  S  I
 W  V  K  V  V  E  E  K  A  F  S  P  E  V  I  P  M  F  S  A 1330      1340      1350      1360      1370      1380
TATCAGAAGGAGCCACCCCACAAGATTTAAACACCATGCTAAACACAGTGGGGGGACATC
  Y  Q  K  E  P  P  H  K  I  *  T  P  C  *  T  Q  W  G  D  I
   I  R  R  S  H  P  T  R  F  K  H  H  A  K  H  S  G  G  T  S
 L  S  E  G  A  T  P  Q  D  L  N  T  M  L  N  T  V  G  G  H 1390      1400      1410      1420      1430      1440
AAGCAGCCATGCAAATGTTAAAAGAGACCATCAATGAGGAAGCTGCAGAATGGGATAGAT
  K  Q  P  C  K  C  *  K  R  P  S  M  R  K  L  Q  N  G  I  D
   S  S  H  A  N  V  K  R  D  H  Q  *  G  S  C  R  M  G  *  I
 Q  A  A  M  Q  M  L  K  E  T  I  N  E  E  A  A  E  W  D  R 1450      1460      1470      1480      1490      1500
TGCATCCAGTGCATGCAGGGCCTATTGCACCAGGCCAGATGAGAGAACCAAGGGGAAGTG
  C  I  Q  C  M  Q  G  L  L  H  Q  A  R  *  E  N  Q  G  E  V
   A  S  S  A  C  R  A  Y  C  T  R  P  D  E  R  T  K  G  K  *
 L  H  P  V  H  A  G  P  I  A  P  G  Q  M  R  E  P  R  G  S 1510      1520      1530      1540      1550      1560
ACATAGCAGGAACTACTAGTACCCTTCAGGAACAAATAGGATGGATGACAAATAATCCAC
  T  *  Q  E  L  L  V  P  F  R  N  K  *  D  G  *  Q  I  I  H
   H  S  R  N  Y  *  Y  P  S  G  T  N  R  M  D  D  K  *  S  T
 D  I  A  G  T  T  S  T  L  Q  E  Q  I  G  W  M  T  N  N  P 1570      1580      1590      1600      1610      1620
CTATCCCAGTAGGAGAAATCTATAAAAGATGGATAATCCTGGGATTAAATAAAATAGTAA
  L  S  Q  *  E  K  S  I  K  D  G  *  S  W  D  *  I  K  *  *
   Y  P  S  R  R  N  L  *  K  M  D  N  P  G  I  K  *  N  S  K
 P  I  P  V  G  E  I  Y  K  R  W  I  I  L  G  L  N  K  I  V
```

Figure 6D

```
        1630      1640      1650      1660      1670      1680
GGATGTATAGCCCTTCCAGCATTCTGGACATAAGACAAGGACCAAAGGAACCCTTTAGAG
  G  C  I  A  L  P  A  F  W  T  *  D  K  D  Q  R  N  P  L  E
 D  V  *  P  F  Q  H  S  G  H  K  T  R  T  K  G  T  L  *  R
R  M  Y  S  P  S  S  I  L  D  I  R  Q  G  P  K  E  P  F  R 1690      1700      1710      1720      1730      1740
ACTATGTAGACCGGTTCTATAAAACTCTAAGAGCCGAGCAAGCTTCACAGGAGGTAAAAA
  T  M  *  T  G  S  I  K  L  *  E  P  S  K  L  H  R  R  *  K
 L  C  R  P  V  L  *  N  S  K  S  R  A  S  F  T  G  G  K  K
D  Y  V  D  R  F  Y  K  T  L  R  A  E  Q  A  S  Q  E  V  K 1750      1760      1770      1780      1790      1800
ATTGGATGACAGAAACCTTGTTGGTCCAAAATGCGAACCCAGATTGTAAGACTATTTTAA
  I  G  *  Q  K  P  C  W  S  K  M  R  T  Q  I  V  R  L  F  *
 L  D  D  R  N  L  V  G  P  K  C  E  P  R  L  *  D  Y  F  K
N  W  M  T  E  T  L  L  V  Q  N  A  N  P  D  C  K  T  I  L 1810      1820      1830      1840      1850      1860
AAGCATTGGGACCAGCAGCTACACTAGAAGAAATGATGACAGCATGTCAGGGAGTGGGAG
  K  H  W  D  Q  Q  L  H  *  K  K  *  *  Q  H  V  R  E  W  E
 S  I  G  T  S  S  Y  T  R  R  N  D  D  S  M  S  G  S  G  R
K  A  L  G  P  A  A  T  L  E  E  M  M  T  A  C  Q  G  V  G 1870      1880      1890      1900      1910      1920
GACCTGGTCATAAAGCAAGAGTTTTGGCGGAAGCGATGAGCCAAGTAACAAATTCAGCTA
  D  L  V  I  K  Q  E  F  W  R  K  R  *  A  K  *  Q  I  Q  L
 T  W  S  *  S  K  S  F  G  G  S  D  E  P  S  N  K  F  S  Y
G  P  G  H  K  A  R  V  L  A  E  A  M  S  Q  V  T  N  S  A 1930      1940      1950      1960      1970      1980
CCATAATGATGCAGAGAGGCAATTTTAGGAATCAAAGAAAGATTATCAAGTGCTTCAATT
  P  *  *  C  R  E  A  I  L  G  I  K  E  R  L  S  S  A  S  I
 H  N  D  A  E  R  Q  F  *  E  S  K  K  D  Y  Q  V  L  Q  L
T  I  M  M  Q  R  G  N  F  R  N  Q  R  K  I  I  K  C  F  N 1990      2000      2010      2020      2030      2040
GTGGCAAAGAAGGGCACATAGCCAAAAATTGCAGGGCCCCTAGGAAAAGGGGCTGTTGGA
  V  A  K  K  G  T  *  P  K  I  A  G  P  L  G  K  G  A  V  G
 W  Q  R  R  A  H  S  Q  K  L  Q  G  P  *  E  K  G  L  L  E
C  G  K  E  G  H  I  A  K  N  C  R  A  P  R  K  R  G  C  W 2050      2060      2070      2080      2090      2100
AATGTGGAAAGGAAGGACACCAAATGAAAGATTGTACTGAGAGACAGGCTAATTTTTTAG
  N  V  E  R  K  D  T  K  *  K  I  V  L  R  D  R  L  I  F  *
 M  W  K  G  R  T  P  N  E  R  L  Y  *  E  T  G  *  F  F  R
K  C  G  K  E  G  H  Q  M  K  D  C  T  E  R  Q  A  N  F  L 2110      2120      2130      2140      2150      2160
GGAAGATCTGGCCTTCCTGCAAGGGAAGGCAGGGAATTTTCCTCAGAGCAGAACAGAGCC
  G  R  S  G  L  P  A  R  E  G  R  E  F  S  S  E  Q  N  R  A
 E  D  L  A  F  L  Q  G  K  A  G  N  F  P  Q  S  R  T  E  P
G  K  I  W  P  S  C  K  G  R  Q  G  I  F  L  R  A  E  Q  S
```

Figure 6E

```
         2170      2180      2190      2200      2210      2220
AACAGCCCCACCAGAAGAGAGCTTCAGGTTTGGGGAAGAGACAACAACTCCCTATCAGAA
  N  S  P  T  R  R  R  E  L  Q  V  W  G  R  D  N  N  S  L  S  E
   T  A  P  P  E  E  S  F  R  F  G  E  E  T  T  T  P  Y  Q  K
 Q  Q  P  H  Q  K  R  A  S  G  L  G  K  R  Q  Q  L  P  I  R 2230      2240      2250      2260      2270      2280
GCAGGAGAAGAAGCAGGAGACGATAGACAAGGACCTGTATCCTTTAGCTTCCCTCAAATC
  A  G  E  E  A  G  D  D  R  Q  G  P  V  S  F  S  F  P  Q  I
   Q  E  K  K  Q  E  T  I  D  K  D  L  Y  P  L  A  S  L  K  S
 S  R  R  R  S  R  R  R  *  T  R  T  C  I  L  *  L  P  S  N 2290      2300      2310      2320      2330      2340
ACTCTTTGGCAACGACCCATTGTCACAATAAAGATAGGGGGGCAACTAAAGGAAGCTCTA
  T  L  W  Q  R  P  I  V  T  I  K  I  G  G  Q  L  K  E  A  L
   L  F  G  N  D  P  L  S  Q  *  R  *  G  G  N  *  R  K  L  Y
 H  S  L  A  T  T  H  C  H  N  K  D  R  G  A  T  K  G  S  S 2350      2360      2370      2380      2390      2400
TTAGATACAGGAGCAGATGATACAGTATTAGAAGAAATGAATTTGCCAGGAAGATGGAAA
  L  D  T  G  A  D  D  T  V  L  E  E  M  N  L  P  G  R  W  K
   *  I  Q  E  Q  M  I  Q  Y  *  K  K  *  I  C  Q  E  D  G  N
 I  R  Y  R  S  R  *  Y  S  I  R  R  N  E  F  A  R  K  M  E 2410      2420      2430      2440      2450      2460
CCAAAAATGATAGGGGGAATTGGAGGTTTTATCAAAGTAAGACAGTATGATCAGATAACC
  P  K  M  I  G  G  I  G  G  F  I  K  V  R  Q  Y  D  Q  I  T
   Q  K  *  *  G  E  L  E  V  L  S  K  *  D  S  M  I  R  *  P
 T  K  N  D  R  G  N  W  R  F  Y  Q  S  K  T  V  *  S  D  N 2470      2480      2490      2500      2510      2520
ATAGAAATCTGTGGACATAAAGCTATAGGTACAGTATTAGTAGGACCTACACCTGTCAAC
  I  E  I  C  G  H  K  A  I  G  T  V  L  V  G  P  T  P  V  N
   *  K  S  V  D  I  K  L  *  V  Q  Y  *  *  D  L  H  L  S  T
 H  R  N  L  W  T  *  S  Y  R  Y  S  I  S  R  T  Y  T  C  Q 2530      2540      2550      2560      2570      2580
ATAATTGGAAGAAATCTGTTGACTCAGCTTGGGTGCACTTTAAATTTTCCCATTAGTCCT
  I  I  G  R  N  L  L  T  Q  L  G  C  T  L  N  F  P  I  S  P
   *  L  E  E  I  C  *  L  S  L  G  A  L  *  I  F  P  L  V  L
 H  N  W  K  K  S  V  D  S  A  W  V  H  F  K  F  S  H  *  S 2590      2600      2610      2620      2630      2640
ATTGAAACTGTACCAGTAAAATTAAAGCCAGGAATGGATGGCCCAAAAGTTAAACAATGG
  I  E  T  V  P  V  K  L  K  P  G  M  D  G  P  K  V  K  Q  W
   L  K  L  Y  Q  *  N  *  S  Q  E  W  M  A  Q  K  L  N  N  G
 Y  *  N  C  T  S  K  I  K  A  R  N  G  W  P  K  S  *  T  M 2650      2660      2670      2680      2690      2700
CCATTGACAGAAGAAAAAATAAAAGCATTAATAGAAATTTGTACAGAAATGGAAAAGGAA
  P  L  T  E  E  K  I  K  A  L  I  E  I  C  T  E  M  E  K  E
   H  *  Q  K  K  K  *  K  H  *  *  K  F  V  Q  K  W  K  R  K
 A  I  D  R  R  K  N  K  S  I  N  R  N  L  Y  R  N  G  K  G
```

Figure 6F

```
        2710      2720      2730      2740      2750      2760
GGGAAAATTTCAAAAATTGGGCCTGAAAATCCATACAATACTCCAGTATTTGCCATAAAG
 G  K  I  S  K  I  G  P  E  N  P  Y  N  T  P  V  F  A  I  K
  G  K  F  Q  K  L  G  L  K  I  H  T  I  L  Q  Y  L  P  *  R
R  E  N  F  K  N  W  A  *  K  S  I  Q  Y  S  S  I  C  H  K 2770      2780      2790      2800      2810      2820
AAAAAAGACAGTACTAAATGGAGAAAATTAGTAGATTTCAGAGAACTTAATAAGAAAACT
 K  K  D  S  T  K  W  R  K  L  V  D  F  R  E  L  N  K  K  T
  K  K  T  V  L  N  G  E  N  *  *  I  S  E  N  L  I  R  K  L
E  K  R  Q  Y  *  M  E  K  I  S  R  F  Q  R  T  *  *  E  N 2830      2840      2850      2860      2870      2880
CAAGACTTCTGGGAAGTTCAATTAGGAATACCACATCCTGCAGGGTTAAAAAAGAAAAAA
 Q  D  F  W  E  V  Q  L  G  I  P  H  P  A  G  L  K  K  K  K
  K  T  S  G  K  F  N  *  E  Y  H  I  L  Q  G  *  K  R  K  N
S  R  L  L  G  S  S  I  R  N  T  T  S  C  R  V  K  K  E  K 2890      2900      2910      2920      2930      2940
TCAGTAACAGTACTGGATGTGGGTGATGCATATTTTTCAGTTCCCTTAGATAAAGACTTC
 S  V  T  V  L  D  V  G  D  A  Y  F  S  V  P  L  D  K  D  F
  Q  *  Q  Y  W  M  W  V  M  H  I  F  Q  F  P  *  I  K  T  S
I  S  N  S  T  G  C  G  *  C  I  F  F  S  S  L  R  *  R  L 2950      2960      2970      2980      2990      3000
AGGAAGTATACTGCATTTACCATACCTAGTATAAACAATGAAACACCAGGGATTAGATAT
 R  K  Y  T  A  F  T  I  P  S  I  N  N  E  T  P  G  I  R  Y
  G  S  I  L  H  L  P  Y  L  V  *  T  M  K  H  Q  G  L  D  I
Q  E  V  Y  C  I  Y  H  T  *  Y  K  Q  *  N  T  R  D  *  I 3010      3020      3030      3040      3050      3060
CAGTACAATGTGCTTCCACAGGGATGGAAAGGATCACCAGCAATATTCCAAAGTAGCATG
 Q  Y  N  V  L  P  Q  G  W  K  G  S  P  A  I  F  Q  S  S  M
  S  T  M  C  F  H  R  D  G  K  D  H  Q  Q  Y  S  K  V  A  *
S  V  Q  C  A  S  T  G  M  E  R  I  T  S  N  I  P  K  *  H 3070      3080      3090      3100      3110      3120
ACAAAAATCTTAGAGCCTTTTAGAAAACAAAATCCAGACATAGTTATCTATCAATACATG
 T  K  I  L  E  P  F  R  K  Q  N  P  D  I  V  I  Y  Q  Y  M
  Q  K  S  *  S  L  L  E  N  K  I  Q  T  *  L  S  I  N  T  W
D  K  N  L  R  A  F  *  K  T  K  S  R  H  S  Y  L  S  I  H 3130      3140      3150      3160      3170      3180
GATGATTTGTATGTAGGATCTGACTTAGAAATAGGGCAGCATAGAGCAAAAATAGAGGAA
 D  D  L  Y  V  G  S  D  L  E  I  G  Q  H  R  A  K  I  E  E
  M  I  C  M  *  D  L  T  *  K  *  G  S  I  E  Q  K  *  R  N
G  *  F  V  C  R  I  *  L  R  N  R  A  A  *  S  K  N  R  G 3190      3200      3210      3220      3230      3240
CTGAGACGACATCTGTTGAGGTGGGGATTTACCACACCAGACAAAAAACATCAGAAAGAA
 L  R  R  H  L  L  R  W  G  F  T  T  P  D  K  K  H  Q  K  E
  *  D  D  I  C  *  G  G  D  L  P  H  Q  T  K  N  I  R  K  N
T  E  T  T  S  V  E  V  G  I  Y  H  T  R  Q  K  T  S  E  R
```

Figure 6G

```
          3250      3260      3270      3280      3290      3300
    CCTCCATTCCTTTGGATGGGTTATGAACTCCATCCTGATAAATGGACAGTACAGCCTATA
      P  P  F  L  W  M  G  Y  E  L  H  P  D  K  W  T  V  Q  P  I
       L  H  S  F  G  W  V  M  N  S  I  L  I  N  G  Q  Y  S  L  *
     T  S  I  P  L  D  G  L  *  T  P  S  *  *  M  D  S  T  A  Y 3310      3320      3330      3340      3350      3360
    GTGCTGCCAGAAAAAGACAGCTGGACTGTCAATGACATACAGAAGTTAGTGGGAAAATTG
      V  L  P  E  K  D  S  W  T  V  N  D  I  Q  K  L  V  G  K  L
       C  C  Q  K  K  T  A  G  L  S  M  T  Y  R  S  *  W  E  N  *
     S  A  A  R  K  R  Q  L  D  C  Q  *  H  T  E  V  S  G  K  I 3370      3380      3390      3400      3410      3420
    AATTGGGCAAGTCAAATTTACGCAGGGATTAAAGTAAAGCAATTATGTAAACTCCTTAGA
      N  W  A  S  Q  I  Y  A  G  I  K  V  K  Q  L  C  K  L  L  R
       I  G  Q  V  K  F  T  Q  G  L  K  *  S  N  Y  V  N  S  L  E
     E  L  G  K  S  N  L  R  R  D  *  S  K  A  I  M  *  T  P  *

3430      3440      3450      3460      3470      3480
    GGAACCAAAGCACTAACAGAAGTAATACCACTAACAGAAGAAGCAGAGCTAGAACTGGCA
      G  T  K  A  L  T  E  V  I  P  L  T  E  E  A  E  L  E  L  A
       E  P  K  H  *  Q  K  *  Y  H  *  Q  K  K  Q  S  *  N  W  Q
     R  N  Q  S  T  N  R  S  N  T  T  N  R  R  S  R  A  R  T  G 3490      3500      3510      3520      3530      3540
    GAAAACAGGGAAATTCTAAAAGAACCAGTACATGGAGTGTATTATGACCCATCAAAAGAC
      E  N  R  E  I  L  K  E  P  V  H  G  V  Y  Y  D  P  S  K  D
       K  T  G  K  F  *  K  N  Q  Y  M  E  C  I  M  T  H  Q  K  T
     R  K  Q  G  N  S  K  R  T  S  T  W  S  V  L  *  P  I  K  R 3550      3560      3570      3580      3590      3600
    TTAATAGCAGAAGTACAGAAGCAGGGGCAAGGCCAATGGACATATCAAATTTATCAAGAG
      L  I  A  E  V  Q  K  Q  G  Q  G  Q  W  T  Y  Q  I  Y  Q  E
       *  *  Q  K  Y  R  S  R  G  K  A  N  G  H  I  K  F  I  K  S
     L  N  S  R  S  T  E  A  G  A  R  P  M  D  I  S  N  L  S  R 3610      3620      3630      3640      3650      3660
    CCATTTAAAAATCTGAAAACAGGCAAATATGCAAGAATGAGGGGTGCCCACACTAATGAT
      P  F  K  N  L  K  T  G  K  Y  A  R  M  R  G  A  H  T  N  D
       H  L  K  I  *  K  Q  A  N  M  Q  E  *  G  V  P  T  L  M  M
     A  I  *  K  S  E  N  R  Q  I  C  K  N  E  G  C  P  H  *  *

3670      3680      3690      3700      3710      3720
    GTAAAACAATTAACAGAGGCAGTGCAAAAAATAGCCACAGAAAGCATAGTAATATGGGGA
      V  K  Q  L  T  E  A  V  Q  K  I  A  T  E  S  I  V  I  W  G
       *  N  N  *  Q  R  Q  C  K  K  *  P  Q  K  A  *  *  Y  G  E
     C  K  T  I  N  R  G  S  A  K  N  S  H  R  K  H  S  N  M  G 3730      3740      3750      3760      3770      3780
    AAGACTCCTAAATTTAGACTACCCATACAAAAAGAAACATGGGAAACATGGTGGACAGAG
      K  T  P  K  F  R  L  P  I  Q  K  E  T  W  E  T  W  W  T  E
       R  L  L  N  L  D  Y  P  Y  K  K  K  H  G  K  H  G  G  Q  S
     K  D  S  *  I  *  T  T  H  T  K  R  N  M  G  N  M  V  D  R
```

Figure 6H

```
          3790       3800       3810       3820       3830       3840
     TATTGGCAAGCCACCTGGATTCCTGAGTGGGAGTTTGTCAATACCCCTCCCTTAGTGAAA
       Y  W  Q  A  T  W  I  P  E  W  E  F  V  N  T  P  P  L  V  K
      I  G  K  P  P  G  F  L  S  G  S  L  S  I  P  L  P  *  *  N
     V  L  A  S  H  L  D  S  *  V  G  V  C  Q  Y  P  S  L  S  E 3850       3860       3870       3880       3890       3900
     TTATGGTACCAGTTAGAGAAAGAACCCATAGTAGGAGCAGAAACTTTCTATGTAGATGGG
       L  W  Y  Q  L  E  K  E  P  I  V  G  A  E  T  F  Y  V  D  G
      Y  G  T  S  *  R  K  N  P  *  *  E  Q  K  L  S  M  *  M  G
     I  M  V  P  V  R  E  R  T  H  S  R  S  R  N  F  L  C  R  W 3910       3920       3930       3940       3950       3960
     GCAGCTAACAGGGAGACTAAAAAAGGAAAAGCAGGATATGTTACTAACAGAGGAAGACAA
       A  A  N  R  E  T  K  K  G  K  A  G  Y  V  T  N  R  G  R  Q
      Q  L  T  G  R  L  K  K  E  K  Q  D  M  L  L  T  E  E  D  K
     G  S  *  Q  G  D  *  K  R  K  S  R  I  C  Y  *  Q  R  K  T 3970       3980       3990       4000       4010       4020
     AAGGTTGTCTCCCTAACTGACACAACAAATCAGAAGACTGAGTTACAAGCAATTCATCTA
       K  V  V  S  L  T  D  T  T  N  Q  K  T  E  L  Q  A  I  H  L
      R  L  S  P  *  L  T  Q  Q  I  R  R  L  S  Y  K  Q  F  I  *
     K  G  C  L  P  N  *  H  N  K  S  E  D  *  V  T  S  N  S  S 4030       4040       4050       4060       4070       4080
     GCTTTGCAAGATTCAGGGTTAGAAGTAAACATAGTAACAGACTCACAATATGCATTAGGA
       A  L  Q  D  S  G  L  E  V  N  I  V  T  D  S  Q  Y  A  L  G
      L  C  K  I  Q  G  *  K  *  T  *  *  Q  T  H  N  M  H  *  E
     S  F  A  R  F  R  V  R  S  K  H  S  N  R  L  T  I  C  I  R 4090       4100       4110       4120       4130       4140
     ATCATTCAAGCACAACCAGATAAAAGTGAATCAGAGTTAGTCAGTCAAATAATAGAGCAG
       I  I  Q  A  Q  P  D  K  S  E  S  E  L  V  S  Q  I  I  E  Q
      S  F  K  H  N  Q  I  K  V  N  Q  S  *  S  V  K  *  *  S  S
     N  H  S  S  T  T  R  *  K  *  I  R  V  S  Q  S  N  N  R  A 4150       4160       4170       4180       4190       4200
     TTAATAAAAAAGGAAAAGGTCTATCTGGCATGGGTACCAGCACACAAAGGAATTGGAGGA
       L  I  K  K  E  K  V  Y  L  A  W  V  P  A  H  K  G  I  G  G
      *  *  K  R  K  R  S  I  W  H  G  Y  Q  H  T  K  E  L  E  E
     V  N  K  K  G  K  G  L  S  G  M  G  T  S  T  Q  R  N  W  R 4210       4220       4230       4240       4250       4260
     AATGAACAAGTAGATAAATTAGTCAGTGCTGGAATCAGGAAAGTACTATTTTTAGATGGA
       N  E  Q  V  D  K  L  V  S  A  G  I  R  K  V  L  F  L  D  G
      M  N  K  *  I  N  *  S  V  L  E  S  G  K  Y  Y  F  *  M  E
     K  *  T  S  R  *  I  S  Q  C  W  N  Q  E  S  T  I  F  R  W 4270       4280       4290       4300       4310       4320
     ATAGATAAGGCCCAAGAAGACCATGAGAAATATCACAGTAATTGGAGAGCAATGGCTAGT
       I  D  K  A  Q  E  D  H  E  K  Y  H  S  N  W  R  A  M  A  S
      *  I  R  P  K  K  T  M  R  N  I  T  V  I  G  E  Q  W  L  V
     N  R  *  G  P  R  R  P  *  E  I  S  Q  *  L  E  S  N  G  *
```

Figure 6I

```
          4330      4340      4350      4360      4370      4380
     GACTTTAACCTACCACCTATAGTAGCAAAAGAAATAGTAGCCAGCTGTGATAAATGTCAG
      D  F  N  L  P  P  I  V  A  K  E  I  V  A  S  C  D  K  C  Q
       T  L  T  Y  H  L  *  *  Q  K  K  *  *  P  A  V  I  N  V  S
        *  L  *  P  T  T  Y  S  S  K  R  N  S  S  Q  L  *  *  M  S 4390      4400      4410      4420      4430      4440
     CTAAAAGGAGAAGCCATGCATGGACAAGTAGACTGTAGTCCAGGAATATGGCAACTAGAT
      L  K  G  E  A  M  H  G  Q  V  D  C  S  P  G  I  W  Q  L  D
       *  K  E  K  P  C  M  D  K  *  T  V  V  Q  E  Y  G  N  *  I
        A  K  R  R  S  H  A  W  T  S  R  L  *  S  R  N  M  A  T  R 4450      4460      4470      4480      4490      4500
     TGTACACATTTAGAAGGAAAAGTTATCCTGGTAGCAGTTCATGTAGCCAGTGGATACATA
      C  T  H  L  E  G  K  V  I  L  V  A  V  H  V  A  S  G  Y  I
       V  H  I  *  K  E  K  L  S  W  *  Q  F  M  *  P  V  D  T  *
        L  Y  T  F  R  R  K  S  Y  P  G  S  S  S  C  S  Q  W  I  H 4510      4520      4530      4540      4550      4560
     GAAGCAGAAGTTATTCCAGCAGAGACAGGGCAGGAGACAGCATACTTTCTCTTAAAATTA
      E  A  E  V  I  P  A  E  T  G  Q  E  T  A  Y  F  L  L  K  L
       K  Q  K  L  F  Q  Q  R  Q  G  R  R  Q  H  T  F  S  *  N  *
        R  S  R  S  Y  S  S  R  D  R  A  G  D  S  I  L  S  L  K  I 4570      4580      4590      4600      4610      4620
     GCAGGAAGATGGCCAGTAAAAACAATACATACAGACAATGGCCCCAATTTCACCAGTACT
      A  G  R  W  P  V  K  T  I  H  T  D  N  G  P  N  F  T  S  T
       Q  E  D  G  Q  *  K  Q  Y  I  Q  T  M  A  P  I  S  P  V  L
        S  R  K  M  A  S  K  N  N  T  Y  R  Q  W  P  Q  F  H  Q  Y 4630      4640      4650      4660      4670      4680
     ACGGTTAAGGCCGCCTGTTGGTGGGCGGGGATCAAGCAGGAATTTGGCATTCCCTACAAT
      T  V  K  A  A  C  W  W  A  G  I  K  Q  E  F  G  I  P  Y  N
       R  L  R  P  P  V  G  G  R  G  S  S  R  N  L  A  F  P  T  I
        Y  G  *  G  R  L  L  V  G  G  D  Q  A  G  I  W  H  S  L  Q 4690      4700      4710      4720      4730      4740
     CCCCAAAGTCAAGGAGTAATAGAATCTATGAATAAAGAATTAAAGAAAATTATAGGACAG
      P  Q  S  Q  G  V  I  E  S  M  N  K  E  L  K  K  I  I  G  Q
       P  K  V  K  E  *  *  N  L  *  I  K  N  *  R  K  L  *  D  R
        S  P  K  S  R  S  N  R  I  Y  E  *  R  I  K  E  N  Y  R  T 4750      4760      4770      4780      4790      4800
     GTAAGAGATCAGGCTGAACATCTTAAGACAGCAGTACAAATGGCAGTATTCATCCACAAT
      V  R  D  Q  A  E  H  L  K  T  A  V  Q  M  A  V  F  I  H  N
       *  E  I  R  L  N  I  L  R  Q  Q  Y  K  W  Q  Y  S  S  T  I
        G  K  R  S  G  *  T  S  *  D  S  S  T  N  G  S  I  H  P  Q 4810      4820      4830      4840      4850      4860
     TTTAAAAGAAAAGGGGGGATTGGGGGGTACAGTGCAGGGGAAAGAATAGTAGACATAATA
      F  K  R  K  G  G  I  G  G  Y  S  A  G  E  R  I  V  D  I  I
       L  K  E  K  G  G  L  G  G  T  V  Q  G  K  E  *  *  T  *  *
        F  *  K  K  R  G  D  W  G  V  Q  C  R  G  K  N  S  R  H  N
```

Figure 6J

```
         4870      4880      4890      4900      4910      4920
    GCAACAGACATACAAACTAAAGAACTACAAAAACAAATTACAAAAATTCAAAATTTTCGG
     A  T  D  I  Q  T  K  E  L  Q  K  Q  I  T  K  I  Q  N  F  R
    Q  Q  T  Y  K  L  K  N  Y  K  N  K  L  Q  K  F  K  I  F  G
   S  N  R  H  T  N  *  R  T  T  K  T  N  Y  K  N  S  K  F  S 4930      4940      4950      4960      4970      4980
    GTTTATTACAGGGACAGCAGAGATCCACTTTGGAAAGGACCAGCAAAGCTTCTCTGGAAA
     V  Y  Y  R  D  S  R  D  P  L  W  K  G  P  A  K  L  L  W  K
    F  I  T  G  T  A  E  I  H  F  G  K  D  Q  Q  S  F  S  G  K
   G  L  L  Q  G  Q  Q  R  S  T  L  E  R  T  S  K  A  S  L  E 4990      5000      5010      5020      5030      5040
    GGTGAAGGGGCAGTAGTAATACAAGATAATAGTGACATAAAAGTAGTGCCAAGAAGAAAA
     G  E  G  A  V  V  I  Q  D  N  S  D  I  K  V  V  P  R  R  K
    V  K  G  Q  *  *  Y  K  I  I  V  T  *  K  *  C  Q  E  E  K
   R  *  R  G  S  S  N  T  R  *  *  *  H  K  S  S  A  K  K  K 5050      5060      5070      5080      5090      5100
    GCAAAGATCATTAGGGATTATGGAAAACAGATGGCAGGTGATGATTGTGTGGCAAGTAGA
     A  K  I  I  R  D  Y  G  K  Q  M  A  G  D  D  C  V  A  S  R
    Q  R  S  L  G  I  M  E  N  R  W  Q  V  M  I  V  W  Q  V  D
   S  K  D  H  *  G  L  W  K  T  D  G  R  *  *  L  C  G  K  *

5110      5120      5130      5140      5150      5160
    CAGGATGAGGATTAGAACATGGAAAAGTTTAGTAAAACACCATATGTATATTTCAAAGAA
     Q  D  E  D  *  N  M  E  K  F  S  K  T  P  Y  V  Y  F  K  E
    R  M  R  I  R  T  W  K  S  L  V  K  H  H  M  Y  I  S  K  K
   T  G  *  G  L  E  H  G  K  V  *  *  N  T  I  C  I  F  Q  R 5170      5180      5190      5200      5210      5220
    AGCTAAAGGATGGTTTTATAGACATCACTATGAAAGCACTCATCCAAGAATAAGTTCAGA
     S  *  R  M  V  L  *  T  S  L  *  K  H  S  S  K  N  K  F  R
    A  K  G  W  F  Y  R  H  H  Y  E  S  T  H  P  R  I  S  S  E
   K  L  K  D  G  F  I  D  I  T  M  K  A  L  I  Q  E  *  V  Q 5230      5240      5250      5260      5270      5280
    AGTACACATCCCACTAGGGGATGCTAGATTGGTAATAACAACATATTGGGGTCTGCATAC
     S  T  H  P  T  R  G  C  *  I  G  N  N  N  I  L  G  S  A  Y
    V  H  I  P  L  G  D  A  R  L  V  I  T  T  Y  W  G  L  H  T
   K  Y  T  S  H  *  G  M  L  D  W  *  *  Q  H  I  G  V  C  I 5290      5300      5310      5320      5330      5340
    AGGAGAAAGAGACTGGCATTTAGGTCAGGGAGTCTCCATAGAATGGAGGAAAAAGAGATA
     R  R  K  R  L  A  F  R  S  G  S  L  H  R  M  E  E  K  E  I
    G  E  R  D  W  H  L  G  Q  G  V  S  I  E  W  R  K  K  R  Y
   Q  E  K  E  T  G  I  *  V  R  E  S  P  *  N  G  G  K  R  D 5350      5360      5370      5380      5390      5400
    TAGCACACAAGTAGACCCTGACCTAGCAGACCACCTAATTCATCTGCATTACTTTGATTG
     *  H  T  S  R  P  *  P  S  R  P  P  N  S  S  A  L  L  *  L
    S  T  Q  V  D  P  D  L  A  D  H  L  I  H  L  H  Y  F  D  C
   I  A  H  K  *  T  L  T  *  Q  T  T  *  F  I  C  I  T  L  I
```

Figure 6K

```
            5410      5420      5430      5440      5450      5460
      TTTTTCAGACTCTGCCATAAGAAAGGCCATATTAGGACATAGAGTTAGTCCTATTTGTGA
       F  F  R  L  C  H  K  K  G  H  I  R  T  *  S  *  S  Y  L  *
        F  S  D  S  A  I  R  K  A  I  L  G  H  R  V  S  P  I  C  E
      V  F  Q  T  L  P  *  E  R  P  Y  *  D  I  E  L  V  L  F  V 5470      5480      5490      5500      5510      5520
      ATTTCAAGCAGGACATAACAAGGTAGGATCTCTACAGTACTTGGCACTAACAGCATTAAT
       I  S  S  R  T  *  Q  G  R  I  S  T  V  L  G  T  N  S  I  N
        F  Q  A  G  H  N  K  V  G  S  L  Q  Y  L  A  L  T  A  L  I
      N  F  K  Q  D  I  T  R  *  D  L  Y  S  T  W  H  *  Q  H  *

5530      5540      5550      5560      5570      5580
      AACACCAAAAAAGATAAAGCCACCTTTGCCTAGTGTTAAGAAACTGACAGAGGATAGATG
       N  T  K  K  D  K  A  T  F  A  *  C  *  E  T  D  R  G  *  M
        T  P  K  K  I  K  P  P  L  P  S  V  K  K  L  T  E  D  R  W
      *  H  Q  K  R  *  S  H  L  C  L  V  L  R  N  *  Q  R  I  D 5590      5600      5610      5620      5630      5640
      GAACAAGCCCCAGAAGACCAAGGGCCACAGAGGGAGCCATACAATCAATGGGCATTAGAG
       E  Q  A  P  E  D  Q  G  P  Q  R  E  P  Y  N  Q  W  A  L  E
        N  K  P  Q  K  T  K  G  H  R  G  S  H  T  I  N  G  H  *  S
      G  T  S  P  R  R  P  R  A  T  E  G  A  I  Q  S  M  G  I  R 5650      5660      5670      5680      5690      5700
      CTTTTAGAGGAGCTTAAGAATGAAGCTGTTAGACATTTTCCTAGGATATGGCTCCATGGC
       L  L  E  E  L  K  N  E  A  V  R  H  F  P  R  I  W  L  H  G
        F  *  R  S  L  R  M  K  L  L  D  I  F  L  G  Y  G  S  M  A
      A  F  R  G  A  *  E  *  S  C  *  T  F  S  *  D  M  A  P  W 5710      5720      5730      5740      5750      5760
      TTAGGGCAACATATCTATGAAACTTATGGGGATACTTGGGCAGGAGTGGAAGCCATAATA
       L  G  Q  H  I  Y  E  T  Y  G  D  T  W  A  G  V  E  A  I  I
        *  G  N  I  S  M  K  L  M  G  I  L  G  Q  E  W  K  P  *  *
      L  R  A  T  Y  L  *  N  L  W  G  Y  L  G  R  S  G  S  H  N 5770      5780      5790      5800      5810      5820
      AGAATTCTACAACAACTGCTGTTTATTCATTTCAGAATTGGGTGTCGACATAGCAGAATA
       R  I  L  Q  Q  L  L  F  I  H  F  R  I  G  C  R  H  S  R  I
        E  F  Y  N  N  C  C  L  F  I  S  E  L  G  V  D  I  A  E  *
      K  N  S  T  T  T  A  V  Y  S  F  Q  N  W  V  S  T  *  Q  N 5830      5840      5850      5860      5870      5880
      GGCATTATTCGACAGAGGAGAGCAAGAAATGGAGCCAGTAGATCCTAGACTAGAGCCCTG
       G  I  I  R  Q  R  R  A  R  N  G  A  S  R  S  *  T  R  A  L
        A  L  F  D  R  G  E  Q  E  M  E  P  V  D  P  R  L  E  P  W
      R  H  Y  S  T  E  E  S  K  K  W  S  Q  *  I  L  D  *  S  P 5890      5900      5910      5920      5930      5940
      GAAGCATCCAGGAAGTCAGCCTAAGACTGCTTGTACCACTTGCTATTGTAAAAAGTGTTG
       E  A  S  R  K  S  A  *  D  C  L  Y  H  L  L  L  *  K  V  L
        K  H  P  G  S  Q  P  K  T  A  C  T  T  C  Y  C  K  K  K  C  C
      G  S  I  Q  E  V  S  L  R  L  L  V  P  L  A  I  V  K  S  V
```

Figure 6L

```
         5950       5960       5970       5980       5990       6000
    CTTTCATTGCCAAGTTTGTTTCACAAAAAAAGCCTTAGGCATCTCCTATGGCAGGAAGAA
      L  S  L  P  S  L  F  H  K  K  S  L  R  H  L  L  W  Q  E  E
     F  H  C  Q  V  C  F  T  K  K  A  L  G  I  S  Y  G  R  K  K
    A  F  I  A  K  F  V  S  Q  K  K  P  *  A  S  P  M  A  G  R 6010       6020       6030       6040       6050       6060
    GCGGAGACAGCGACGAAGAGCTCCTGAAGACAGTCAGACTCATCAAGTTTCTCTACCAAA
      A  E  T  A  T  K  S  S  *  R  Q  S  D  S  S  S  F  S  T  K
     R  R  Q  R  R  R  A  P  E  D  S  Q  T  H  Q  V  S  L  P  K
    S  G  D  S  D  E  E  L  L  K  T  V  R  L  I  K  F  L  Y  Q 6070       6080       6090       6100       6110       6120
    GCAGTAAGTAGTACATGTAATGCAACCTTTAGTAATAGCAGCAATAGTAGCATTAGTAGT
      A  V  S  S  T  C  N  A  T  F  S  N  S  S  N  S  S  I  S  S
     Q  *  V  V  H  V  M  Q  P  L  V  I  A  A  I  V  A  L  V  V
    S  S  K  *  Y  M  *  C  N  L  *  *  *  Q  Q  *  *  H  *  *

6130       6140       6150       6160       6170       6180
    AGCAGGAATAATAGCAATAGTTGTGTGATCCATAGTATTCATAGAATATAGGAAAATAAG
      S  R  N  N  S  N  S  C  V  I  H  S  I  H  R  I  *  E  N  K
     A  G  I  I  A  I  V  V  *  S  I  V  F  I  E  Y  R  K  I  R
    *  Q  E  *  *  Q  *  L  C  D  P  *  Y  S  *  N  I  G  K  *

6190       6200       6210       6220       6230       6240
    AAGACAAAGAAAAATAGACAGGGTAATTGACAGAATAAGCGAAAGAGCAGAAGACAGTGG
      K  T  K  K  N  R  Q  G  N  *  Q  N  K  R  K  S  R  R  Q  W
     R  Q  R  K  I  D  R  V  I  D  R  I  S  E  R  A  E  D  S  G
    E  D  K  E  K  *  T  G  *  L  T  E  *  A  K  E  Q  K  T  V 6250       6260       6270       6280       6290       6300
    CAATGAGAGTGAAGGGGATCAGGAGGAATTATCAGCACTGGTGGGGATGGGGCACGATGC
      Q  *  E  *  R  G  S  G  G  I  I  S  T  G  G  D  G  A  R  C
     N  E  S  E  G  D  Q  E  E  L  S  A  L  V  G  M  G  H  D  A
    A  M  R  V  K  G  I  R  R  N  Y  Q  H  W  W  G  W  G  T  M 6310       6320       6330       6340       6350       6360
    TCCTTGGGTTATTAATGATCTGTAGTGCTACAGAAAAATTGTGGGTCACAGTCTATTATG
      S  L  G  Y  *  *  S  V  V  L  Q  K  N  C  G  S  Q  S  I  M
     P  W  V  I  N  D  L  *  C  Y  R  K  I  V  G  H  S  L  L  W
    L  L  G  L  L  M  I  C  S  A  T  E  K  L  W  V  T  V  Y  Y 6370       6380       6390       6400       6410       6420
    GGGTACCTGTGTGGAAAGAAGCAACCACCACTCTATTTTGTGCATCAGATGCTAAAGCAT
      G  Y  L  C  G  K  K  Q  P  P  L  Y  F  V  H  Q  M  L  K  H
     G  T  C  V  E  R  S  N  H  H  S  I  L  C  I  R  C  *  S  I
    G  V  P  V  W  K  E  A  T  T  T  L  F  C  A  S  D  A  K  A 6430       6440       6450       6460       6470       6480
    ATGATACAGAGGTACATAATGTTTGGGCCACACATGCCTGTGTACCCACAGACCCCAACC
      M  I  Q  R  Y  I  M  F  G  P  H  M  P  V  Y  P  Q  T  P  T
     *  Y  R  G  T  *  C  L  G  H  T  C  L  C  T  H  R  P  Q  P
    Y  D  T  E  V  H  N  V  W  A  T  H  A  C  V  P  T  D  P  N
```

Figure 6M

```
        6490      6500      6510      6520      6530      6540
CACAAGAAGTAGAATTGGTAAATGTGACAGAAAATTTTAACATGTGGAAAAATAACATGG
  H  K  K  *  N  W  *  M  *  Q  K  I  L  T  C  G  K  I  T  W
   T  R  S  R  I  G  K  C  D  R  K  F  *  H  V  E  K  *  H  G
    P  Q  E  V  E  L  V  N  V  T  E  N  F  N  M  W  K  N  N  M 6550      6560      6570      6580      6590      6600
TAGAACAGATGCATGAGGATATAATCAGTTTATGGGATCAAAGCCTAAAGCCATGTGTAA
  *  N  R  C  M  R  I  *  S  V  Y  G  I  K  A  *  S  H  V  *
   R  T  D  A  *  G  Y  N  Q  F  M  G  S  K  P  K  A  M  C  K
    V  E  Q  M  H  E  D  I  I  S  L  W  D  Q  S  L  K  P  C  V 6610      6620      6630      6640      6650      6660
AATTAACCCCACTCTGTGTTACTTTAAATTGCACTGATTTGAGGAATACTACTAATACCA
  N  *  P  H  S  V  L  L  *  I  A  L  I  *  G  I  L  L  I  P
   I  N  P  T  L  C  Y  F  K  L  H  *  F  E  E  Y  Y  *  Y  Q
    K  L  T  P  L  C  V  T  L  N  C  T  D  L  R  N  T  T  N  T 6670      6680      6690      6700      6710      6720
ATAATAGTACTGCTAATAACAATAGTAATAGCGAGGGAACAATAAAGGGAGGAGAAATGA
  I  I  V  L  L  I  T  I  V  I  A  R  E  Q  *  R  E  E  K  *
   *  *  Y  C  *  *  Q  *  *  *  R  G  N  N  K  G  R  R  N  E
    N  N  S  T  A  N  N  N  S  N  S  E  G  T  I  K  G  G  E  M 6730      6740      6750      6760      6770      6780
AAAACTGCTCTTTCAATATCACCACAAGCATAAGAGATAAGATGCAGAAAGAATATGCAC
  K  T  A  L  S  I  S  P  Q  A  *  E  I  R  C  R  K  N  M  H
   K  L  L  F  Q  Y  H  H  K  H  K  R  *  D  A  E  R  I  C  T
    K  N  C  S  F  N  I  T  T  S  I  R  D  K  M  Q  K  E  Y  A 6790      6800      6810      6820      6830      6840
TTCTTTATAAACTTGATATAGTATCAATAAATAATGATAGTACCAGCTATAGGTTGATAA
  F  F  I  N  L  I  *  Y  Q  *  I  M  I  V  P  A  I  G  *  *
   S  L  *  T  *  Y  S  I  N  K  *  *  *  Y  Q  L  *  V  D  K
    L  L  Y  K  L  D  I  V  S  I  N  N  D  S  T  S  Y  R  L  I 6850      6860      6870      6880      6890      6900
GTTGTAATACCTCAGTCATTACACAAGCTTGTCCAAAGATATCCTTTGAGCCAATTCCCA
  V  V  I  P  Q  S  L  H  K  L  V  Q  R  Y  P  L  S  Q  F  P
   L  *  Y  L  S  H  Y  T  S  L  S  K  D  I  L  *  A  N  S  H
    S  C  N  T  S  V  I  T  Q  A  C  P  K  I  S  F  E  P  I  P 6910      6920      6930      6940      6950      6960
TACACTATTGTGCCCCGGCTGGTTTTGCGATTCTAAAGTGTAACGATAAAAAGTTCAGTG
  Y  T  I  V  P  R  L  V  L  R  F  *  S  V  T  I  K  S  S  V
   T  L  L  C  P  G  W  F  C  D  S  K  V  *  R  *  K  V  Q  W
    I  H  Y  C  A  P  A  G  F  A  I  L  K  C  N  D  K  K  F  S 6970      6980      6990      7000      7010      7020
GAAAAGGATCATGTAAAAATGTCAGCACAGTACAATGTACACATGGAATTAGGCCAGTAG
  E  K  D  H  V  K  M  S  A  Q  Y  N  V  H  M  E  L  G  Q  *
   K  R  I  M  *  K  C  Q  H  S  T  M  Y  T  W  N  *  A  S  S
    G  K  G  S  C  K  N  V  S  T  V  Q  C  T  H  G  I  R  P  V
```

Figure 6N

```
            7030      7040      7050      7060      7070      7080
        TATCAACTCAACTGCTGTTAAATGGCAGTCTAGCAGAAGAAGAGGTAGTAATTAGATCTG
         Y  Q  L  N  C  C  *  M  A  V  *  Q  K  K  R  *  *  L  D  L
          I  N  S  T  A  V  K  W  Q  S  S  R  R  R  G  S  N  *  I  *
        V  S  T  Q  L  L  L  N  G  S  L  A  E  E  E  V  V  I  R  S 7090      7100      7110      7120      7130      7140
        AGAATTTCAATGATAATGCTAAAACCATCATAGTACATCTGAATGAATCTGTACAAATTA
         R  I  S  M  I  M  L  K  P  S  *  Y  I  *  M  N  L  Y  K  L
          E  F  Q  *  *  C  *  N  H  H  S  T  S  E  *  I  C  T  N  *
        E  N  F  N  D  N  A  K  T  I  I  V  H  L  N  E  S  V  Q  I 7150      7160      7170      7180      7190      7200
        ATTGTACAAGACCCAACTACAATAAAAGAAAAAGGATACATATAGGACCAGGGAGAGCAT
         I  V  Q  D  P  T  T  I  K  E  K  G  Y  I  *  D  Q  G  E  H
          L  Y  K  T  Q  L  Q  *  K  K  K  D  T  Y  R  T  R  E  S  I
        N  C  T  R  P  N  Y  N  K  R  K  R  I  H  I  G  P  G  R  A 7210      7220      7230      7240      7250      7260
        TTTATACAACAAAAAATATAATAGGAACTATAAGACAAGCACATTGTAACATTAGTAGAG
         F  I  Q  Q  K  I  *  *  E  L  *  D  K  H  I  V  T  L  V  E
          L  Y  N  K  K  Y  N  R  N  Y  K  T  S  T  L  *  H  *  *  S
        F  Y  T  T  K  N  I  I  G  T  I  R  Q  A  H  C  N  I  S  R 7270      7280      7290      7300      7310      7320
        CAAAATGGAATGACACTTTAAGACAGATAGTTAGCAAATTAAAAGAACAATTTAAGAATA
         Q  N  G  M  T  L  *  D  R  *  L  A  N  *  K  N  N  L  R  I
          K  M  E  *  H  F  K  T  D  S  *  Q  I  K  R  T  I  *  E  *
        A  K  W  N  D  T  L  R  Q  I  V  S  K  L  K  E  Q  F  K  N 7330      7340      7350      7360      7370      7380
        AAACAATAGTCTTTAATCAATCCTCAGGAGGGGACCCAGAAATTGTAATGCACAGTTTTA
         K  Q  *  S  L  I  N  P  Q  E  G  T  Q  K  L  *  C  T  V  L
          N  N  S  L  *  S  I  L  R  R  G  P  R  N  C  N  A  Q  F  *
        K  T  I  V  F  N  Q  S  S  G  G  D  P  E  I  V  M  H  S  F 7390      7400      7410      7420      7430      7440
        ATTGTGGAGGGGAATTTTTCTACTGTAATACATCACCACTGTTTAATAGTACTTGGAATG
         I  V  E  G  N  F  S  T  V  I  H  H  H  C  L  I  V  L  G  M
          L  W  R  G  I  F  L  L  *  Y  I  T  T  V  *  *  Y  L  E  W
        N  C  G  G  E  F  F  Y  C  N  T  S  P  L  F  N  S  T  W  N 7450      7460      7470      7480      7490      7500
        GTAATAATACTTGGAATAATACTACAGGGTCAAATAACAATATCACACTTCAATGCAAAA
         V  I  I  L  G  I  I  L  Q  G  Q  I  T  I  S  H  F  N  A  K
          *  *  Y  L  E  *  Y  Y  R  V  K  *  Q  Y  H  T  S  M  Q  N
        G  N  N  T  W  N  N  T  T  G  S  N  N  N  I  T  L  Q  C  K 7510      7520      7530      7540      7550      7560
        TAAAACAAATTATAAACATGTGGCAGGAAGTAGGAAAAGCAATATATGCCCCTCCCATTG
         *  N  K  L  *  T  C  G  R  K  *  E  K  Q  Y  M  P  L  P  L
          K  T  N  Y  K  H  V  A  G  S  R  K  S  N  I  C  P  S  H  *
        I  K  Q  I  I  N  M  W  Q  E  V  G  K  A  I  Y  A  P  P  I
```

Figure 6O

```
          7570      7580      7590      7600      7610      7620
     AAGGACAAATTAGATGTTCATCAAATATTACAGGGCTACTATTAACAAGAGATGGTGGTA
      K  D  K  L  D  V  H  Q  I  L  Q  G  Y  Y  *  Q  E  M  V  V
       R  T  N  *  M  F  I  K  Y  Y  R  A  T  I  N  K  R  W  W  *
     E  G  Q  I  R  C  S  S  N  I  T  G  L  L  L  T  R  D  G  G 7630      7640      7650      7660      7670      7680
     AGGACACGGACACGAACGACACCGAGATCTTCAGACCTGGAGGAGGAGATATGAGGGACA
      R  T  R  T  R  T  T  P  R  S  S  D  L  E  E  E  I  *  G  T
       G  H  G  H  E  R  H  R  D  L  Q  T  W  R  R  R  Y  E  G  Q
     K  D  T  D  T  N  D  T  E  I  F  R  P  G  G  G  D  M  R  D 7690      7700      7710      7720      7730      7740
     ATTGGAGAAGTGAATTATATAAATATAAAGTAGTAACAATTGAACCATTAGGAGTAGCAC
      I  G  E  V  N  Y  I  N  I  K  *  *  Q  L  N  H  *  E  *  H
       L  E  K  *  I  I  *  I  *  S  S  N  N  *  T  I  R  S  S  T
     N  W  R  S  E  L  Y  K  Y  K  V  V  T  I  E  P  L  G  V  A 7750      7760      7770      7780      7790      7800
     CCACCAAGGCAAAGAGAAGAGTGGTGCAGAGAGAAAAAAGAGCAGCGATAGGAGCTCTGT
      P  P  R  Q  R  E  E  W  C  R  E  K  K  E  Q  R  *  E  L  C
       H  Q  G  K  E  K  S  G  A  E  R  K  K  S  S  D  R  S  S  V
     S  T  K  A  K  R  R  V  V  Q  R  E  K  R  A  A  I  G  A  L 7810      7820      7830      7840      7850      7860
     TCCTTGGGTTCTTAGGAGCAGCAGGAAGCACTATGGGCGCAGCGTCAGTGACGCTGACGG
      S  L  G  S  *  E  Q  Q  E  A  L  W  A  Q  R  Q  *  R  *  R
       P  W  V  L  R  S  S  R  K  H  Y  G  R  S  V  S  D  A  D  G
     F  L  G  F  L  G  A  A  G  S  T  M  G  A  A  S  V  T  L  T 7870      7880      7890      7900      7910      7920
     TACAGGCCAGACTATTATTGTCTGGTATAGTGCAACAGCAGAACAATTTGCTGAGGGCCA
      Y  R  P  D  Y  Y  C  L  V  *  C  N  S  R  T  I  C  *  G  P
       T  G  Q  T  I  I  V  W  Y  S  A  T  A  E  Q  F  A  E  G  H
     V  Q  A  R  L  L  L  S  G  I  V  Q  Q  Q  N  N  L  L  R  A 7930      7940      7950      7960      7970      7980
     TTGAGGCGCAACAGCATATGTTGCAACTCACAGTCTGGGGCATCAAGCAGCTCCAGGCAA
      L  R  R  N  S  I  C  C  N  S  Q  S  G  A  S  S  S  S  R  Q
       *  G  A  T  A  Y  V  A  T  H  S  L  G  H  Q  A  A  P  G  K
     I  E  A  Q  Q  H  M  L  Q  L  T  V  W  G  I  K  Q  L  Q  A 7990      8000      8010      8020      8030      8040
     GAATCCTGGCTGTGGAAAGATACCTAAAGGATCAACAGCTCCTGGGGATTTGGGGTTGCT
      E  S  W  L  W  K  D  T  *  R  I  N  S  S  W  G  F  G  V  A
       N  P  G  C  G  K  I  P  K  G  S  T  A  P  G  D  L  G  L  L
     R  I  L  A  V  E  R  Y  L  K  D  Q  Q  L  L  G  I  W  G  C 8050      8060      8070      8080      8090      8100
     CTGGAAAACTCATTTGCACCACTACTGTGCCTTGGAATGCTAGTTGGAGTAATAAATCTC
      L  E  N  S  F  A  P  L  L  C  L  G  M  L  V  G  V  I  N  L
       W  K  T  H  L  H  H  H  Y  C  A  L  E  C  *  L  E  *  *  I  S
     S  G  K  L  I  C  T  T  T  V  P  W  N  A  S  W  S  N  K  S
```

Figure 6P

```
           8110      8120      8130      8140      8150      8160
     TGGATGATATTTGGAATAACATGACCTGGATGCAGTGGGAAAGAGAAATTGACAATTACA
      W  M  I  F  G  I  T  *  P  G  C  S  G  K  E  K  L  T  I  T
        G  *  Y  L  E  *  H  D  L  D  A  V  G  K  R  N  *  Q  L  H
       L  D  D  I  W  N  N  M  T  W  M  Q  W  E  R  E  I  D  N  Y 8170      8180      8190      8200      8210      8220
     CAAGCTTAATATACTCATTACTAGAAAAATCGCAAACCCAACAAGAAATGAATGAACAAG
      Q  A  *  Y  T  H  Y  *  K  N  R  K  P  N  K  K  *  M  N  K
        K  L  N  I  L  I  T  R  K  I  A  N  P  T  R  N  E  *  T  R
       T  S  L  I  Y  S  L  L  E  K  S  Q  T  Q  Q  E  M  N  E  Q 8230      8240      8250      8260      8270      8280
     AATTATTGGAATTGGATAAATGGGCAAGTTTGTGGAATTGGTTTGACATAACAAATTGGC
      N  Y  W  N  W  I  N  G  Q  V  C  G  I  G  L  T  *  Q  I  G
        I  I  G  I  G  *  M  G  K  F  V  E  L  V  *  H  N  K  L  A
       E  L  L  E  L  D  K  W  A  S  L  W  N  W  F  D  I  T  N  W 8290      8300      8310      8320      8330      8340
     TGTGGTATATAAAAATATTCATAATGATAGTAGGAGGCTTGGTAGGTTTAAGAATAGTTT
      C  G  I  *  K  Y  S  *  *  *  *  E  A  W  *  V  *  E  *  F
        V  V  Y  K  N  I  H  N  D  S  R  R  L  G  R  F  K  N  S  F
       L  W  Y  I  K  I  F  I  M  I  V  G  G  L  V  G  L  R  I  V 8350      8360      8370      8380      8390      8400
     TTGCTGTACTTTCTATAGTGAATAGAGTTAGGCAGGGATACTCACCATTGTCGTTGCAGA
      L  L  Y  F  L  *  *  I  E  L  G  R  D  T  H  H  C  R  C  R
        C  C  T  F  Y  S  E  *  S  *  A  G  I  L  T  I  V  V  A  D
       F  A  V  L  S  I  V  N  R  V  R  Q  G  Y  S  P  L  S  L  Q 8410      8420      8430      8440      8450      8460
     CCCGCCCCCCAGTTCCGAGGGGACCCGACAGGCCCGAAGGAATCGAAGAAGAAGGTGGAG
      P  A  P  Q  F  R  G  D  P  T  G  P  K  E  S  K  K  K  V  E
        P  P  P  S  S  E  G  T  R  Q  A  R  R  N  R  R  R  R  W  R
       T  R  P  P  V  P  R  G  P  D  R  P  E  G  I  E  E  E  G  G 8470      8480      8490      8500      8510      8520
     AGAGAGACAGAGACACATCCGGTCGATTAGTGCATGGATTCTTAGCAATTATCTGGGTCG
      R  E  T  E  T  H  P  V  D  *  C  M  D  S  *  Q  L  S  G  S
        E  R  Q  R  H  I  R  S  I  S  A  W  I  L  S  N  Y  L  G  R
       E  R  D  R  D  T  S  G  R  L  V  H  G  F  L  A  I  I  W  V 8530      8540      8550      8560      8570      8580
     ACCTGCGGAGCCTGTTCCTCTTCAGCTACCACCACTTGAGAGACTTACTCTTGATTGCAG
      T  C  G  A  C  S  S  S  A  T  T  T  *  E  T  Y  S  *  L  Q
        P  A  E  P  V  P  L  Q  L  P  P  L  E  R  L  T  L  D  C  S
       D  L  R  S  L  F  L  F  S  Y  H  H  L  R  D  L  L  L  I  A 8590      8600      8610      8620      8630      8640
     CGAGGATTGTGGAACTTCTGGGACGCAGGGGGTGGGAAGTCCTCAAATATTGGTGGAATC
      R  G  L  W  N  F  W  D  A  G  G  G  K  S  S  N  I  G  G  I
        E  D  C  G  T  S  G  T  Q  G  V  G  S  P  Q  I  L  V  E  S
       A  R  I  V  E  L  L  G  R  R  G  W  E  V  L  K  Y  W  W  N
```

Figure 6Q

```
        8650      8660      8670      8680      8690      8700
TCCTACAGTATTGGAGTCAGGAACTAAAGAGTAGTGCTGTTAGCTTGCTTAATGCCACAG
  S  Y  S  I  G  V  R  N  *  R  V  V  L  L  A  C  L  M  P  Q
   P  T  V  L  E  S  G  T  K  E  *  C  C  *  L  A  *  C  H  R
 L  L  Q  Y  W  S  Q  E  L  K  S  S  A  V  S  L  L  N  A  T 8710      8720      8730      8740      8750      8760
ATATAGCAGTAGCTGAGGGGACAGATAGGGTTATAGAAGTACTGCAAAGAGCTGGTAGAG
  I  *  Q  *  L  R  G  Q  I  G  L  *  K  Y  C  K  E  L  V  E
   Y  S  S  S  *  G  D  R  *  G  Y  R  S  T  A  K  S  W  *  S
 D  I  A  V  A  E  G  T  D  R  V  I  E  V  L  Q  R  A  G  R 8770      8780      8790      8800      8810      8820
CTATTCTCCACATACCTACAAGAATAAGACAGGGCTTGGAAAGGGCTTTGCTATAAGATG
  L  F  S  T  Y  L  Q  E  *  D  R  A  W  K  G  L  C  Y  K  M
   Y  S  P  H  T  Y  K  N  K  T  G  L  G  K  G  F  A  I  R  W
 A  I  L  H  I  P  T  R  I  R  Q  G  L  E  R  A  L  L  *  D 8830      8840      8850      8860      8870      8880
GGTGGCAAATGGTCAAAACGTGTGACTGGATGGCCTACTGTAAGGGAAAAAATGAGACGA
  G  G  K  W  S  K  R  V  T  G  W  P  T  V  R  E  K  M  R  R
   V  A  N  G  Q  N  V  *  L  D  G  L  L  *  G  K  K  *  D  E
 G  W  Q  M  V  K  T  C  D  W  M  A  Y  C  K  G  K  N  E  T 8890      8900      8910      8920      8930      8940
GCTGAACCAGCTGAGCCAGCAGCAGATGGGGTGGGAGCAGCATCCCGAGACCTGGAAAAA
  A  E  P  A  E  P  A  A  D  G  V  G  A  A  S  R  D  L  E  K
   L  N  Q  L  S  Q  Q  Q  M  G  W  E  Q  H  P  E  T  W  K  N
 S  *  T  S  *  A  S  S  R  W  G  G  S  S  I  P  R  P  G  K 8950      8960      8970      8980      8990      9000
CATGGAGCACTCACAAGTAGCAATACAGCAGCTACCAATGCTGATTGTGCCTGGCTAGAA
  H  G  A  L  T  S  S  N  T  A  A  T  N  A  D  C  A  W  L  E
   M  E  H  S  Q  V  A  I  Q  Q  L  P  M  L  I  V  P  G  *  K
 T  W  S  T  H  K  *  Q  Y  S  S  Y  Q  C  *  L  C  L  A  R 9010      9020      9030      9040      9050      9060
GCACAAGAGGAGGAGGAAGTGGGTTTTCCAGTCAGACCTCAGGTACCTTTAAGACCAATG
  A  Q  E  E  E  E  V  G  F  P  V  R  P  Q  V  P  L  R  P  M
   H  K  R  R  R  K  W  V  F  Q  S  D  L  R  Y  L  *  D  Q  *
 S  T  R  G  G  G  S  G  F  S  S  Q  T  S  G  T  F  K  T  N 9070      9080      9090      9100      9110      9120
ACTTACAAAGCAGCTTTAGATCTTAGCCACTTTTTAAAAGAAAAGGGGGGACTGGATGGG
  T  Y  K  A  A  L  D  L  S  H  F  L  K  E  K  G  G  L  D  G
   L  T  K  Q  L  *  I  L  A  T  F  *  K  K  R  G  D  W  M  G
 D  L  Q  S  S  F  R  S  *  P  L  F  K  R  K  G  G  T  G  W 9130      9140      9150      9160      9170      9180
TTAATTTACTCCCAAAAGAGACAAGACATCCTTGATCTGTGGGTCTACCACACACAAGGC
  L  I  Y  S  Q  K  R  Q  D  I  L  D  L  W  V  Y  H  T  Q  G
   *  F  T  P  K  R  D  K  T  S  L  I  C  G  S  T  T  H  K  A
 V  N  L  L  P  K  E  T  R  H  P  *  S  V  G  L  P  H  T  R
```

Figure 6R

```
         9190      9200      9210      9220      9230      9240
TACTTCCCTGATTGGCAGAACTACACACCAGGGCCAGGGATCAGATATCCACTGACCTTT
  Y  F  P  D  W  Q  N  Y  T  P  G  P  G  I  R  Y  P  L  T  F
   T  S  L  I  G  R  T  T  H  Q  G  Q  G  S  D  I  H  *  P  L
 L  L  P  *  L  A  E  L  H  T  R  A  R  D  Q  I  S  T  D  L 9250      9260      9270      9280      9290      9300
GGATGGTGCTTCAAGCTAGTACCAGTTGAGCCAGAGAAGATAGAAGAGGCCAATAAAGGA
  G  W  C  F  K  L  V  P  V  E  P  E  K  I  E  E  A  N  K  G
   D  G  A  S  S  *  Y  Q  L  S  Q  R  R  *  K  R  P  I  K  E
 W  M  V  L  Q  A  S  T  S  *  A  R  E  D  R  R  G  Q  *  R 9310      9320      9330      9340      9350      9360
GAGAACAACTGCTTGTTACACCCTATGAGCCAGCATGGGATGGATGACCCGGAGAGAGAA
  E  N  N  C  L  L  H  P  M  S  Q  H  G  M  D  D  P  E  R  E
   R  T  T  A  C  Y  T  L  *  A  S  M  G  W  M  T  R  R  E  K
 R  E  Q  L  L  V  T  P  Y  E  P  A  W  D  G  *  P  G  E  R 9370      9380      9390      9400      9410      9420
GTGTTAGTGTGGAAGTCTGACAGCCACCTAGCATTTCAGCATTATGCCCGAGAGCTGCAT
  V  L  V  W  K  S  D  S  H  L  A  F  Q  H  Y  A  R  E  L  H
   C  *  C  G  S  L  T  A  T  *  H  F  S  I  M  P  E  S  C  I
 S  V  S  V  E  V  *  Q  P  P  S  I  S  A  L  C  P  R  A  A 9430      9440      9450      9460      9470      9480
CCGGAGTACTACAAGAACTGCTGACATCGAGCTATCTACAAGGGACTTTCCGCTGGGGAC
  P  E  Y  Y  K  N  C  *  H  R  A  I  Y  K  G  L  S  A  G  D
   R  S  T  T  R  T  A  D  I  E  L  S  T  R  D  F  P  L  G  T
 S  G  V  L  Q  E  L  L  T  S  S  Y  L  Q  G  T  F  R  W  G 9490      9500      9510      9520      9530      9540
TTTCCAGGGAGGTGTGGCCTGGGCGGGACCGGGGAGTGGCGAGCCCTCAGATGCTGCATA
  F  P  G  R  C  G  L  G  G  T  G  E  W  R  A  L  R  C  C  I
   F  Q  G  G  V  A  W  A  G  P  G  S  G  E  P  S  D  A  A  Y
 L  S  R  E  V  W  P  G  R  D  R  G  V  A  S  P  Q  M  L  H 9550      9560      9570      9580      9590      9600
TAAGCAGCTGCTTTCTGCCTGTACTGGGTCTCTCTGGTTAGACCAGATCTGAGCCTGGGA
  *  A  A  A  F  C  L  Y  W  V  S  L  V  R  P  D  L  S  L  G
   K  Q  L  L  S  A  C  T  G  S  L  W  L  D  Q  I  *  A  W  E
 I  S  S  C  F  L  P  V  L  G  L  S  G  *  T  R  S  E  P  G 9610      9620      9630      9640      9650      9660
GCTCTCTGGCTAACTAGGGAACCCACTGCTTAAGCCTCAATAAAGCTTGCCTTGAGTGCT
  A  L  W  L  T  R  E  P  T  A  *  A  S  I  K  L  A  L  S  A
   L  S  G  *  L  G  N  P  L  L  K  P  Q  *  S  L  P  *  V  L
 S  S  L  A  N  *  G  T  H  C  L  S  L  N  K  A  C  L  E  C 9670      9680      9690      9700      9710      9720
TCAAGTAGTGTGTGCCCGTCTGTTATGTGACTCTGGTAGCTAGAGATCCCTCAGATCCTT
  S  S  S  V  C  P  S  V  M  *  L  W  *  L  E  I  P  Q  I  L
   Q  V  V  C  A  R  L  L  C  D  S  G  S  *  R  S  L  R  S  F
 F  K  *  C  V  P  V  C  Y  V  T  L  V  A  R  D  P  S  D  P
```

Figure 6S

```
       9730          9740
TTAGGCAGTGTGGAAAATCTCTAGCA
  L   G   S   V   E   N   L   *
    *   A   V   W   K   I   S   S
F   R   Q   C   G   K   S   L   A
```

Figure 8A

```
          10         20         30         40         50         60
GATCAAGGGCCACAGAGGGAGCCACACAATGAATGGACACTAGAGCTTTTAGAGGAGCTT
 D  Q  G  P  Q  R  E  P  H  N  E  W  T  L  E  L  L  E  E  L
  I  K  G  H  R  G  S  H  T  M  N  G  H  *  S  F  *  R  S  L
   S  R  A  T  E  G  A  T  Q  *  M  D  T  R  A  F  R  G  A 70         80         90        100        110        120
AAGAGTGAAGCTGTTAGACACTTTCCTAGGATATGGCTTCATGGCTTAGGGCAACATATC
 K  S  E  A  V  R  H  F  P  R  I  W  L  H  G  L  G  Q  H  I
  R  V  K  L  L  D  T  F  L  G  Y  G  F  M  A  *  G  N  I  S
   *  E  *  S  C  *  T  L  S  *  D  M  A  S  W  L  R  A  T  Y 130        140        150        160        170        180
TATGAAACTTATGGGGATACTTGGGCAGGAGTGGAAGCCATAATAAGAATTCTGCAACAA
 Y  E  T  Y  G  D  T  W  A  G  V  E  A  I  I  R  I  L  Q  Q
  M  K  L  M  G  I  L  G  Q  E  W  K  P  *  *  E  F  C  N  N
   L  *  N  L  W  G  Y  L  G  R  S  G  S  H  N  K  N  S  A  T 190        200        210        220        230        240
CTGCTGTTTATCCATTTCAGGATTGGGTGCCAACATAGCAGAATAGGTATTATTCAACAG
 L  L  F  I  H  F  R  I  G  C  Q  H  S  R  I  G  I  I  Q  Q
  C  C  L  S  I  S  G  L  G  A  N  I  A  E  *  V  L  F  N  R
   T  A  V  Y  P  F  Q  D  W  V  P  T  *  Q  N  R  Y  Y  S  T 250        260        270        280        290        300
AGGAGAGCAAGAAATGGAGCCAGTAGATCCTAAACTAGAGCCCTGGAAGCATCCAGGAAG
 R  R  A  R  N  G  A  S  R  S  *  T  R  A  L  E  A  S  R  K
  G  E  Q  E  M  E  P  V  D  P  K  L  E  P  W  K  H  P  G  S
   E  E  S  K  K  W  S  Q  *  I  L  N  *  S  P  G  S  I  Q  E 310        320        330        340        350        360
TCAGCCTAAGACTGCTTGTACCACTTGCTATTGTAAAAAGTGTTGCTTTCATTGCCAAGT
 S  A  *  D  C  L  Y  H  L  L  L  *  K  V  L  L  S  L  P  S
  Q  P  K  T  A  C  T  T  C  Y  C  K  K  C  C  F  H  C  Q  V
   V  S  L  R  L  L  V  P  L  A  I  V  K  S  V  A  F  I  A  K 370        380        390        400        410        420
TTGCTTCATAACAAAAGGCTTAGGCATCTCCTATGGCAGGAAGAAGCGGAGACAGCGACG
 L  L  H  N  K  R  L  R  H  L  L  W  Q  E  E  A  E  T  A  T
  C  F  I  T  K  G  L  G  I  S  Y  G  R  K  K  R  R  Q  R  R
   F  A  S  *  Q  K  A  *  A  S  P  M  A  G  R  S  G  D  S  D
                                    ‾‾‾‾‾‾‾‾‾‾‾‾‾‾‾‾‾‾‾‾‾‾‾‾‾‾
                                         (Rev)
         430        440        450        460        470        480
AAGAGCTCCTCAAGACAGTGAGACTCATCAAGTTTCTCTATCAAAGCAGTAAGTAGTACA
 K  S  S  S  R  Q  *  D  S  S  S  F  S  I  K  A  V  S  S  T
  R  A  P  Q  D  S  E  T  H  Q  V  S  L  S  K  Q  *  V  V  H
   E  E  L  L  K  T  V  R  L  I  K  F  L  Y  Q  S  S  K  *  Y
   ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
         490        500        510        520        530        540
TGTAATGCAAGCTTTACAAATATCAGCTATAGTAGGATTAGTAGTAGCAGCAATAATAGC
 C  N  A  S  F  T  N  I  S  Y  S  R  I  S  S  S  N  N  S
  V  M  Q  A  L  Q  I  S  A  I  V  G  L  V  V  A  A  I  I  A
   M  *  C  K  L  Y  K  Y  Q  L  *  *  D  *  *  *  Q  Q  *  *
```

Figure 8B

```
          550         560         570         580         590         600
    AATAGTTGTGTGGACCATAGTATTCATAGAATATAGGAAAATATTAAGGCAAAGAAAAAT
     N  S  C  V  D  H  S  I  H  R  I  *  E  N  I  K  A  K  K  N
      I  V  V  W  T  I  V  F  I  E  Y  R  K  I  L  R  Q  R  K  I
       Q  *  L  C  G  P  *  Y  S  *  N  I  G  K  Y  *  G  K  E  K 610         620         630         640         650         660
    AGACAGGTTAATTGATAGAATAACAGAAAGAGCAGAAGACAGTGGCAATGAGAGTGACGG
     R  Q  V  N  *  *  N  N  R  K  S  R  R  Q  W  Q  *  E  *  R
      D  R  L  I  D  R  I  T  E  R  A  E  D  S  G  N  E  S  D  G
       *  T  G  *  L  I  E  *  Q  K  E  Q  K  T  V  A  M  R  V  T
                                                       (Env)
          670         680         690         700         710         720
    AGATCAGGAAGAGTTATCAGCACTGGTGGAGATGGGGCATCATGCTCCTTGGGATATTAA
     R  S  G  R  V  I  S  T  G  G  D  G  A  S  C  S  L  G  Y  *
      D  Q  E  E  L  S  A  L  V  E  M  G  H  H  A  P  W  D  I  N
       E  I  R  K  S  Y  Q  H  W  W  R  W  G  I  M  L  L  G  I  L 730         740         750         760         770         780
    TGATCTGTAATGCTGAAGAAAAATTGTGGGTCACAGTCTATTATGGGGTACCTGTGTGGA
     *  S  V  M  L  K  K  N  C  G  S  Q  S  I  M  G  Y  L  C  G
      D  L  *  C  *  R  K  I  V  G  H  S  L  L  W  G  T  C  V  E
       M  I  C  N  A  E  E  K  L  W  V  T  V  Y  Y  G  V  P  V  W 790         800         810         820         830         840
    AAGAAGCAACCACCACTCTATTTTGTGCATCAGATCGTAAAGCATATGATACAGAGGTAC
     K  K  Q  P  P  L  Y  F  V  H  Q  I  V  K  H  M  I  Q  R  Y
      R  S  N  H  H  S  I  L  C  I  R  S  *  S  I  *  Y  R  G  T
       K  E  A  T  T  T  L  F  C  A  S  D  R  K  A  Y  D  T  E  V 850         860         870         880         890         900
    ATAATGTTTGGGCCACACATGCCTGTGTACCCACAGACCCCAACCCACAAGAAGTAGAAT
     I  M  F  G  P  H  M  P  V  Y  P  Q  T  P  T  H  K  K  *  N
      *  C  L  G  H  T  C  L  C  T  H  R  P  Q  P  T  R  S  R  I
       H  N  V  W  A  T  H  A  C  V  P  T  D  P  N  P  Q  E  V  E 910         920         930         940         950         960
    TGAAAAATGTGACAGAAAATTTTAACATGTGGAAAAATAACATGGTAGAACAAATGCATG
     *  K  M  *  Q  K  I  L  T  C  G  K  I  T  W  *  N  K  C  M
      E  K  C  D  R  K  F  *  H  V  E  K  *  H  G  R  T  N  A  *
       L  K  N  V  T  E  N  F  N  M  W  K  N  N  M  V  E  Q  M  H 970         980         990        1000        1010        1020
    AGGATATAATCAGTTTATGGGATCAAAGCCTAAAGCCATGTGTAAAATTAACCCCACTCT
     R  I  *  S  V  Y  G  I  K  A  *  S  H  V  *  N  *  P  H  S
      G  Y  N  Q  F  M  G  S  K  P  K  A  M  C  K  I  N  P  T  L
       E  D  I  I  S  L  W  D  Q  S  L  K  P  C  V  K  L  T  P  L 1030        1040        1050        1060        1070        1080
    GTGTTACTTTAAATTGCACTGATTTGAGGAATGCTACTAATGGGAATGACACTAATACCA
     V  L  L  *  I  A  L  I  *  G  M  L  L  M  G  M  T  L  I  P
      C  Y  F  K  L  H  *  F  E  E  C  Y  *  W  E  *  H  *  Y  H
       C  V  T  L  N  C  T  D  L  R  N  A  T  N  G  N  D  T  N  T
```

Figure 8C

```
         1090      1100      1110      1120      1130      1140
     CTAGTAGTAGCAGGGGAATGGTGGGGGGAGGAGAAATGAAAAATTGCTCTTTCAATATCA
       L  V  V  A  G  E  W  W  G  E  E  K  *  K  I  A  L  S  I  S
        *  *  *  Q  G  N  G  G  G  R  R  N  E  K  L  L  F  Q  Y  H
         T  S  S  S  R  G  M  V  G  G  G  E  M  K  N  C  S  F  N  I 1150      1160      1170      1180      1190      1200
     CCACAAACATAAGAGGTAAGGTGCAGAAAGAATATGCACTTTTTTATAAACTTGATATAG
       P  Q  T  *  E  V  R  C  R  K  N  M  H  F  F  I  N  L  I  *
        H  K  H  K  R  *  G  A  E  R  I  C  T  F  L  *  T  *  Y  S
         T  T  N  I  R  G  K  V  Q  K  E  Y  A  L  F  Y  K  L  D  I 1210      1220      1230      1240      1250      1260
     CACCAATAGATAATAATAGTAATAATAGATATAGGTTGATAAGTTGTAACACCTCAGTCA
       H  Q  *  I  I  I  V  I  I  D  I  G  *  *  V  V  T  P  Q  S
        T  N  R  *  *  *  *  *  *  I  *  V  D  K  L  *  H  L  S  H
         A  P  I  D  N  N  S  N  N  R  Y  R  L  I  S  C  N  T  S  V 1270      1280      1290      1300      1310      1320
     TTACACAGGCCTGTCCAAAGGTATCCTTTGAGCCAATTCCCATACATTATTGTGCCCCGG
       L  H  R  P  V  Q  R  Y  P  L  S  Q  F  P  Y  I  I  V  P  R
        Y  T  G  L  S  K  G  I  L  *  A  N  S  H  T  L  L  C  P  G
         I  T  Q  A  C  P  K  V  S  F  E  P  I  P  I  H  Y  C  A  P 1330      1340      1350      1360      1370      1380
     CTGGTTTTGCGATTCTAAAGTGTAAAGATAAGAAGTTCAATGGAAAAGGACCATGTACAA
       L  V  L  R  F  *  S  V  K  I  R  S  S  M  E  K  D  H  V  Q
        W  F  C  D  S  K  V  *  R  *  E  V  Q  W  K  R  T  M  Y  K
         A  G  F  A  I  L  K  C  K  D  K  K  F  N  G  K  G  P  C  T 1390      1400      1410      1420      1430      1440
     ATGTCAGCACAGTACAATGTACACATGGAATTAGGCCAGTAGTATCAACTCAACTGCTGT
       M  S  A  Q  Y  N  V  H  M  E  L  G  Q  *  Y  Q  L  N  C  C
        C  Q  H  S  T  M  Y  T  W  N  *  A  S  S  I  N  S  T  A  V
         N  V  S  T  V  Q  C  T  H  G  I  R  P  V  V  S  T  Q  L  L 1450      1460      1470      1480      1490      1500
     TAAATGGCAGTCTAGCAGAAGAAGAGGTAGTAATTAGATCCGCCAATTTCGCGGACAATG
       *  M  A  V  *  Q  K  K  R  *  *  L  D  P  P  I  S  R  T  M
        K  W  Q  S  S  R  R  R  G  S  N  *  I  R  Q  F  R  G  Q  C
         L  N  G  S  L  A  E  E  E  V  V  I  R  S  A  N  F  A  D  N 1510      1520      1530      1540      1550      1560
     CTAAAGTCATAATAGTACAGCTGAATGAATCTGTAGAAATTAATTGTACAAGACCCAACA
       L  K  S  *  *  Y  S  *  M  N  L  *  K  L  I  V  Q  D  P  T
        *  S  H  N  S  T  A  E  *  I  C  R  N  *  L  Y  K  T  Q  Q
         A  K  V  I  I  V  Q  L  N  E  S  V  E  I  N  C  T  R  P  N 1570      1580      1590      1600      1610      1620
     ACAATACAAGAAAAAGTATACATATAGGACCAGGCAGAGCATTTTATACAACAGGAGAAA
       T  I  Q  E  K  V  Y  I  *  D  Q  A  E  H  F  I  Q  Q  E  K
        Q  Y  K  K  K  Y  T  Y  R  T  R  Q  S  I  L  Y  N  R  R  N
         N  N  T  R  K  S  I  H  I  G  P  G  R  A  F  Y  T  T  G  E
```

Figure 8D

```
           1630        1640        1650        1660        1670        1680
      TAATAGGAGATATAAGACAAGCACATTGTAACCTTAGTAGAGCAAAATGGAATGACACTT
        *  *  E  I  *  D  K  H  I  V  T  L  V  E  Q  N  G  M  T  L
         N  R  R  Y  K  T  S  T  L  *  P  *  *  S  K  M  E  *  H  F
        I  I  G  D  I  R  Q  A  H  C  N  L  S  R  A  K  W  N  D  T 1690        1700        1710        1720        1730        1740
      TAAATAAGATAGTTATAAAATTAAGAGAACAATTTGGGAATAAAACAATAGTCTTTAAGC
        *  I  R  *  L  *  N  *  E  N  N  L  G  I  K  Q  *  S  L  S
         K  *  D  S  Y  K  I  K  R  T  I  W  E  *  N  N  S  L  *  A
        L  N  K  I  V  I  K  L  R  E  Q  F  G  N  K  T  I  V  F  K 1750        1760        1770        1780        1790        1800
      ACTCCTCAGGAGGGGACCCAGAAATTGTGACGCACAGTTTTAATTGTGGAGGGGAATTTT
        T  P  Q  E  G  T  Q  K  L  *  R  T  V  L  I  V  E  G  N  F
         L  L  R  R  G  P  R  N  C  D  A  Q  F  *  L  W  R  G  I  F
        H  S  S  G  G  D  P  E  I  V  T  H  S  F  N  C  G  G  E  F 1810        1820        1830        1840        1850        1860
      TCTACTGTAATTCAACACAACTGTTTAATAGTACTTGGAATGTTACTGAAGAGTCAAATA
        S  T  V  I  Q  H  N  C  L  I  V  L  G  M  L  L  K  S  Q  I
         L  L  *  F  N  T  T  V  *  *  Y  L  E  C  Y  *  R  V  K  *
        F  Y  C  N  S  T  Q  L  F  N  S  T  W  N  V  T  E  E  S  N 1870        1880        1890        1900        1910        1920
      ACACTGTAGAAAATAACACAATCACACTCCCATGCAGAATAAAACAAATTATAAACATGT
        T  L  *  K  I  T  Q  S  H  S  H  A  E  *  N  K  L  *  T  C
         H  C  R  K  *  H  N  H  T  P  M  Q  N  K  T  N  Y  K  H  V
        N  T  V  E  N  N  T  I  T  L  P  C  R  I  K  Q  I  I  N  M 1930        1940        1950        1960        1970        1980
      GGCAGGAAGTAGGAAGAGCAATGTATGCCCCTCCCATCAGAGGACAAATTAGATGTTCAT
        G  R  K  *  E  E  Q  C  M  P  L  P  S  E  D  K  L  D  V  H
         A  G  S  R  K  S  N  V  C  P  S  H  Q  R  T  N  *  M  F  I
        W  Q  E  V  G  R  A  M  Y  A  P  P  I  R  G  Q  I  R  C  S 1990        2000        2010        2020        2030        2040
      CAAATATTACAGGGCTGCTATTAACAAGAGATGGTGGTCCTGAGGACAACAAGACCGAGG
        Q  I  L  Q  G  C  Y  *  Q  E  M  V  V  L  R  T  T  R  P  R
         K  Y  Y  R  A  A  I  N  K  R  W  W  S  *  G  Q  Q  D  R  G
        S  N  I  T  G  L  L  L  T  R  D  G  G  P  E  D  N  K  T  E 2050        2060        2070        2080        2090        2100
      TCTTCAGACCTGGAGGAGGAGATATGAGGGATAATTGGAGAAGTGAATTATATAAATATA
        S  S  D  L  E  E  E  I  *  G  I  I  G  E  V  N  Y  I  N  I
         L  Q  T  W  R  R  R  Y  E  G  *  L  E  K  *  I  I  *  I  *
        V  F  R  P  G  G  G  D  M  R  D  N  W  R  S  E  L  Y  K  Y 2110        2120        2130        2140        2150        2160
      AAGTAGTAAAAATTGAACCATTAGGAGTAGCACCCACCAAGGCAAAGAGAAGAGTGGTGC
        K  *  *  K  L  N  H  *  E  *  H  P  P  R  Q  R  E  E  W  C
         S  S  K  N  *  T  I  R  S  S  T  H  Q  G  K  E  K  S  G  A
        K  V  V  K  I  E  P  L  G  V  A  P  T  K  A  K  R  R  V  V
```

Figure 8E

```
          2170      2180      2190      2200      2210      2220
     AGAGAGAAAAAAGAGCAGTGGGAATAGGAGCTGTGTTCCTTGGGTTCTTGGGAGCAGCAG
      R  E  K  K  E  Q  W  E  *  E  L  C  S  L  G  S  W  E  Q  Q
       E  R  K  K  S  S  G  N  R  S  C  V  P  W  V  L  G  S  S  R
     Q  R  E  K  R  A  V  G  I  G  A  V  F  L  G  F  L  G  A  A 2230      2240      2250      2260      2270      2280
     GAAGCACTATGGGCGCAGCGGCAATGACGCTGACGGTACAGGCCAGACTATTATTGTCTG
      E  A  L  W  A  Q  R  Q  *  R  *  R  Y  R  P  D  Y  Y  C  L
       K  H  Y  G  R  S  G  N  D  A  D  G  T  G  Q  T  I  I  V
     G  S  T  M  G  A  A  A  M  T  L  T  V  Q  A  R  L  L  L  S 2290      2300      2310      2320      2330      2340
     GTATAGTGCAACAGCAGAACAATCTGCTGAGGGCTATTGAGGCGCAACAGCATCTGTTGC
      V  *  C  N  S  R  T  I  C  *  G  L  L  R  R  N  S  I  C  C
       Y  S  A  T  A  E  Q  S  A  E  G  Y  *  G  A  T  A  S  V  A
     G  I  V  Q  Q  Q  N  N  L  L  R  A  I  E  A  Q  Q  H  L  L 2350      2360      2370      2380      2390      2400
     AACTCACAGTCTGGGGCATCAAGCAGCTCCAGGCAAGAGTCCTGGCTGTGGAAAGATACC
      N  S  Q  S  G  A  S  S  S  S  R  Q  E  S  W  L  W  K  D  T
       T  H  S  L  G  H  Q  A  A  P  G  K  S  P  G  C  G  K  I  P
     Q  L  T  V  W  G  I  K  Q  L  Q  A  R  V  L  A  V  E  R  Y 2410      2420      2430      2440      2450      2460
     TAAGGGATCAACAGCTCCTGGGGATTTGGGGTTGCTCTGGAAAACTCATCTGCACCACTG
      *  G  I  N  S  S  W  G  F  G  V  A  L  E  N  S  S  A  P  L
       K  G  S  T  A  P  G  D  L  G  L  L  W  K  T  H  L  H  H  C
     L  R  D  Q  Q  L  L  G  I  W  G  C  S  G  K  L  I  C  T  T 2470      2480      2490      2500      2510      2520
     CTGTGCCTTGGAATGCTAGTTGGAGTAATAAATCTCTGAATAAGATTTGGGATAACATGA
      L  C  L  G  M  L  V  G  V  I  N  L  *  I  R  F  G  I  T  *
       C  A  L  E  C  *  L  E  *  *  I  S  E  *  D  L  G  *  H  D
     A  V  P  W  N  A  S  W  S  N  K  S  L  N  K  I  W  D  N  M 2530      2540      2550      2560      2570      2580
     CCTGGATAGAGTGGGACAGAGAAATTAACAATTACACAAGCATAATATACAGCTTAATTG
      P  G  *  S  G  T  E  K  L  T  I  T  Q  A  *  Y  T  A  *  L
       L  D  R  V  G  Q  R  N  *  Q  L  H  K  H  N  I  Q  L  N  *
     T  W  I  E  W  D  R  E  I  N  N  Y  T  S  I  I  Y  S  L  I 2590      2600      2610      2620      2630      2640
     AAGAATCGCAGAACCAACAAGAAAAGAATGAACAAGAATTATTAGAATTAGATAAATGGG
      K  N  R  R  T  N  K  K  R  M  N  K  N  Y  *  N  *  I  N  G
       R  I  A  E  P  T  R  K  E  *  T  R  I  I  R  I  R  *  M  G
     E  E  S  Q  N  Q  Q  E  K  N  E  Q  E  L  L  E  L  D  K  W 2650      2660      2670      2680      2690      2700
     CAAGTTTGTGGAATTGGTTTGACATAACAAAATGGCTGTGGTATATAAAAATATTCATAA
      Q  V  C  G  I  G  L  T  *  Q  N  G  C  G  I  *  K  Y  S  *
       K  F  V  E  L  V  *  H  N  K  M  A  V  V  Y  K  N  I  H  N
     A  S  L  W  N  W  F  D  I  T  K  W  L  W  Y  I  K  I  F  I
```

Figure 8F

```
          2710       2720       2730       2740       2750       2760
       TGATAGTAGGAGGCTTGATAGGTTTAAGAATAGTTTTTCTGTACTTTCTATAGTAATA
        *  *  *  E  A  *  *  V  *  E  *  F  F  L  Y  F  L  *  *  I
         D  S  R  R  L  D  R  F  K  N  S  F  F  C  T  F  Y  S  E  *
          M  I  V  G  G  L  I  G  L  R  I  V  F  S  V  L  S  I  V  N 2770       2780       2790       2800       2810       2820
       GAGTTAGGCAGGGATACTCACCATTATCGTTTCAGACCCACCTCCCATCCTCGAGGGGAC
         E  L  G  R  D  T  H  H  Y  R  F  R  P  T  S  H  P  R  G  D
          S  *  A  G  I  L  T  I  I  V  S  D  P  P  P  I  L  E  G  T  (Rev)
           R  V  R  Q  G  Y  S  P  L  S  F  Q  T  H  L  P  S  S  R  G  (Env)

2830       2840       2850       2860       2870       2880
       CCGACAGGCCCGGAGGAATCGAAGAAGAAGGTGGAGAGAGAGACAGAGACAGATCCGGTC
          P  T  G  P  E  E  S  K  K  K  V  E  R  E  T  E  T  D  P  V
           R  Q  A  R  R  N  R  R  R  R  W  R  E  R  Q  R  Q  I  R  S
         P  D  R  P  G  G  I  E  E  E  G  G  E  R  D  R  D  R  S  G 2890       2900       2910       2920       2930       2940
       CATTAGTGAACGGATTCTTGGCGCTTATCTGGGTCGATCTGCGGAGCCTGTTCCTCTTCA
         H  *  *  T  D  S  W  R  L  S  G  S  I  C  G  A  C  S  S  S
          I  S  E  R  I  L  G  A  Y  L  G  R  S  A  E  P  V  P  L  Q
           P  L  V  N  G  F  L  A  L  I  W  V  D  L  R  S  L  F  L  F 2950       2960       2970       2980       2990       3000
       GCTACCACCGCTTGAGAGACTTACTCTTGATTGTGATGAGGATTGTGGAACTTCTGGGAC
         A  T  T  A  *  E  T  Y  S  *  L  *  *  G  L  W  N  F  W  D
          L  P  P  L  E  R  L  T  L  D  C  D  E  D  C  G  T  S  G  T
           S  Y  H  R  L  R  D  L  L  L  I  V  M  R  I  V  E  L  L  G 3010       3020       3030       3040       3050       3060
       TAGCAGGGGGGTGGGAAGTCCTCAAATATTGGTGGAATCTCCTACAGTATTGGAGTCAGG
         *  Q  G  G  G  K  S  S  N  I  G  G  I  S  Y  S  I  G  V  R
           S  R  G  V  G  S  P  Q  I  L  V  E  S  P  T  V  L  E  S  G
          L  A  G  G  W  E  V  L  K  Y  W  W  N  L  L  Q  Y  W  S  Q 3070       3080       3090       3100       3110       3120
       AACTAAAGAATAGTGCTGTTAGCTTGCTAATGCCACAGCTGTAGCAGTAGCTGAAGGGA
         N  *  R  I  V  L  L  A  C  S  M  P  Q  L  *  Q  *  L  K  G
          T  K  E  *  C  C  *  L  A  Q  C  H  S  C  S  S  *  R  D
           E  L  K  N  S  A  V  S  L  L  N  A  T  A  V  A  V  A  E  G 3130       3140       3150       3160       3170       3180
       CAGATAGGGTTATAGAAGTATTACAGAGAGCTGTTAGAGCTATTCTCCACATACCTAGAA
         Q  I  G  L  *  K  Y  Y  R  E  L  L  E  L  F  S  T  Y  L  E
          R  *  G  Y  R  S  I  T  E  S  C  *  S  Y  S  P  H  T  *  K
           T  D  R  V  I  E  V  L  Q  R  A  V  R  A  I  L  H  I  P  R 3190       3200       3210       3220       3230       3240
       GAATAAGACAGGGCTTGGAAAGGGCTTTGCTATAAGATGGGTGGCAAGTGGTCAAAAAGT
         E  *  D  R  A  W  K  G  L  C  Y  K  M  G  G  K  W  S  K  S
          N  K  T  G  L  G  K  G  F  A  I  R  W  V  A  S  G  Q  K  V
           R  I  R  Q  G  L  E  R  A  L  L  *  D  G  W  Q  V  V  K  K
```

Figure 8G

```
        3250      3260      3270      3280      3290      3300
AGTATAGTCGTATGGCCTGCTGTAAGGAAAAGAATGAGAAGAACTGAGCCAGCAGCAGAT
  S  I  V  V  W  P  A  V  R  K  R  M  R  R  T  E  P  A  A  D
   V  *  S  Y  G  L  L  *  G  K  E  *  E  E  L  S  Q  Q  Q  M
 *  Y  S  R  M  A  C  C  K  E  K  N  E  K  N  *  A  S  S  R 3310      3320      3330      3340      3350      3360
GGAGTAGGAGCAGTATCTAGAGACCTGGAAAAACATGGAGCAATCACAAGTAGCAATACA
  G  V  G  A  V  S  R  D  L  E  K  H  G  A  I  T  S  S  N  T
   E  *  E  Q  Y  L  E  T  W  K  N  M  E  Q  S  Q  V  A  I  Q
 W  S  R  S  S  I  *  R  P  G  K  T  W  S  N  H  K  *  Q  Y 3370      3380      3390      3400      3410      3420
GCAGCTAACAATGCTGATTGTGCCTGGCTAGAAGCACAAGAGGATGAAGAAGTGGGTTTT
  A  A  N  N  A  D  C  A  W  L  E  A  Q  E  D  E  E  V  G  F
   Q  L  T  M  L  I  V  P  G  *  K  H  K  R  M  K  K  W  V  F
 S  S  *  Q  C  *  L  C  L  A  R  S  T  R  G  *  R  S  G  F 3430      3440      3450      3460      3470      3480
CCAGTCAGACCTCAGGTACCTTTAAGACCAATGACTCGCAGTGCAGCTATAGATCTTAGC
  P  V  R  P  Q  V  P  L  R  P  M  T  R  S  A  A  I  D  L  S
   Q  S  D  L  R  Y  L  *  D  Q  *  L  A  V  Q  L  *  I  L  A
 S  S  Q  T  S  G  T  F  K  T  N  D  S  Q  C  S  Y  R  S  *

3490      3500      3510      3520      3530      3540
CACTTTTTTAAGAAAAAGGGGGGACTGGAAGGGCTAATTCACTCCCAAAAAAGACAAGAT
  H  F  F  K  K  K  G  G  L  E  G  L  I  H  S  Q  K  R  Q  D
   T  F  L  R  K  R  G  D  W  K  G  *  F  T  P  K  K  D  K  I
 P  L  F  *  E  K  G  G  T  G  R  A  N  S  L  P  K  K  T  R 3550      3560      3570      3580      3590      3600
ATCCTTGATTTGTGGGTCTACCACACACAAGGCTACTTCCCTGATTGGCAGAACTACACA
  I  L  D  L  W  V  Y  H  T  Q  G  Y  F  P  D  W  Q  N  Y  T
   S  L  I  C  G  S  T  T  H  K  A  T  S  L  I  G  R  T  T  H
 Y  P  *  F  V  G  L  P  H  T  R  L  L  P  *  L  A  E  L  H 3610      3620      3630      3640      3650      3660
CCAGGGCCAGGGACCAGATTTCCACTGACCTTTGGATGGTGCTTCAAGCTAGTACCAGTT
  P  G  P  G  T  R  F  P  L  T  F  G  W  C  F  K  L  V  P  V
   Q  G  Q  G  P  D  F  H  *  P  L  D  G  A  S  S  *  Y  Q  L
 T  R  A  R  D  Q  I  S  T  D  L  W  M  V  L  Q  A  S  T  S 3670      3680      3690      3700      3710      3720
GAGCCAGAGAAGGTAGAAGAGGCCAATGAAGGAGAGAACAACTGCTTGTCACACCCTATG
  E  P  E  K  V  E  E  A  N  E  G  E  N  N  C  L  S  H  P  M
   S  Q  R  R  *  K  R  P  M  K  E  R  T  T  A  C  H  T  L  *
 *  A  R  E  G  R  R  G  Q  *  R  R  E  Q  L  L  V  T  P  Y 3730      3740      3750      3760      3770      3780
AGCCTGCATGGGATGGATGACCCGGAGAAAGAAGTGTTAGCATGGAAGTTTGACAGCAGC
  S  L  H  G  M  D  D  P  E  K  E  V  L  A  W  K  F  D  S  S
   A  C  M  G  W  M  T  R  R  K  K  C  *  H  G  S  L  T  A  A
 E  P  A  W  D  G  *  P  G  E  R  S  V  S  M  E  V  *  Q  Q
```

Figure 8H

```
      3790       3800
CTAGCATTCCATCACGTGGCCCGAGAA
 L  A  F  H  H  V  A  R  E
  *  H  S  I  T  W  P  E
P  S  I  P  S  R  G  P  R
```

MOLECULAR CLONES OF HIV-1 VIRAL STRAINS MN-ST1 AND BA-L, AND USES THEREOF

This is a divisional of application Ser. No. 08/388,809, filed Feb. 15, 1995, now U.S. Pat. No. 5,576,000, which is a divisional of application Ser. No. 08/022,835 filed Feb. 25, 1993, now U.S. Pat. No. 5,420,030, which is a continuation of application Ser. No. 07/599,491, filed Oct. 17, 1990, abandoned.

BACKGROUND OF THE INVENTION

HIV-1 has been identified as the etiologic agent of the acquired immunodeficiency syndrome (AIDS) (Barre-Sinoussi et al., Science 220, 868–871, 1983; Popovic et al, Science 224, 497–500, 1984; Gallo et al., Science 224, 500–503, 1984). Infected individuals generally develop antibodies to the virus within several months of exposure (Sarngadharan et al., Science 224, 506–508, 1984), which has made possible the development of immunologically based tests which can identify most of blood samples from infected individuals. This is a great advantage in diagnosis, and is vital to maintaining the maximum possible safety of samples from blood banks.

An important aspect of HIV-1 is its genetic variability (Hahn et al., Proc. Natl. Acad. Sci. U.S.A. 82, 4813–4817, 1985). This is particularly evident in the gene for the outer envelope glycoprotein (Starcich et al., Cell 45, 637–648, 1986; Alizon et al., Cell 46, 63–74, 1986; Gurgo et al., Virology 164, 531–536, 1988). Since the outer envelope glycoprotein is on the surface of the virus particle and the infected cell, it is potentially one of the primary targets of the immune system, including the target of neutralizing antibodies and cytotoxic T cells. This variability may also lead to differences in the ability of antigens from different strains of HIV-1 to be recognized by antibodies from a given individual, as well as to differences in the ability of proteins from different strains of virus to elicit an immune response which would be protective against the mixture of virus strains that exists in the at risk populations.

Several biologically active complete molecular clones of various strains of HIV-1 have been obtained and sequenced. These clones, however, seem to represent viral genotypes which are relatively atypical of United States HIV-1 isolates. In addition, several of the translational reading frames for non-structural viral proteins are not complete. Further, viruses derived from these clones do not grow in macrophages, in contrast to many HIV-1 field isolates and, perhaps, because of this lack of ability to infect macrophage efficiently, these clones do not replicate well in chimpanzees. This latter ability is important for testing candidate vaccines in animal systems. In addition, the ability to infect macrophages is critical in evaluating the possible protective efficacy of an elicited immune response since neutralization of infectivity on macrophages may differ from the better studied neutralization on T cells.

Neutralizing antibodies (Robert-Guroff et al., Nature 316, 72–74, 1985; Weiss et al., Nature 316, 69–72, 1985) have been demonstrated in infected individuals, as have cytotoxic T cell responses (Walker et al, Nature 328, 345–348, 1988). Although these do not appear to be protective, it is likely that if they were present prior to infection, they would prevent infection, especially by related strains of virus. This is supported by the finding that macaques can be protected by immunization with inactivated simian immunodeficiency virus (SIV) from infection with the homologous live virus (Murphy-Corb et al., Science 246, 1293–1297, 1989). Chimps also have been passively protected against challenge by live virus by prior administration of neutralizing antibodies to the same virus (Emini et al., J. Virol. 64, 3674–3678, 1989). One problem, however, is that at least some of the neutralizing antibodies studied depend on recognition of a variable region on the envelope (Matsushita et al., J. Virol. 62, 2107–2114, 1988; Rusche et al., Proc. Natl. Acad. Sci. U.S.A. 85, 3198–3202, 1988; Skinner et al., AIDS Res. Hum. Retroviruses 4, 187–197, 1988) called the V3 region (Starcich et al., Cell 45, 637–648, 1986).

An at least partial solution to the problem of viral heterogeneity is to identify prototypical HIV-1 strains, that is, those that are most similar by DNA sequence data or serologic reactivity to strains present in the population at risk. The inclusion of a limited number of such prototype strains in a polyvalent vaccine cocktail might then result in elicitation of an immune response protective against most naturally occurring viruses within a given population. Such a mixture should also provide the maximum possible sensitivity in diagnostic tests for antibodies in infected individuals.

Components of highly representative isolates of a geographical area provide the maximum possible sensitivity in diagnostic tests and vaccines. Production of viral proteins from molecular clones by recombinant DNA techniques is the preferred and safest means to provide such proteins. Molecular clones of prototype HIV-1 strains can serve as the material from which such recombinant proteins can be made. The use of recombinant DNA avoids any possibility of the presence of live virus and affords the opportunity of genetically modifying viral gene products. The use of biological active clones ensures that the gene products are functional and hence, maximizes their potential relevance.

Infectious clones, that is, those which after transfection into recipient cells produce complete virus, are desirable for several reasons. One reason is that the gene products are by definition functional; this maximizes their potential relevance to what is occurring in vivo. A second reason is that genetically altered complete virus is easy to obtain. Consequently, the biological consequences of variability can be easily assessed. For example, the effect of changes in the m envelope gene on the ability of the virus to be neutralized by antibody can be easily addressed. Using this technique, a single point mutation in the envelope gene has been shown to confer resistance to neutralizing antibody (Reitz et al., Cell 54, 57–63, 1988). A third reason is that a clonal virus population provides the greatest possible definition for challenge virus in animals receiving candidate vaccines, especially those including components of the same molecularly cloned virus.

SUMMARY OF THE INVENTION

It is an object of the present invention to provide vaccine components for an anti HIV-1 vaccine which would represent a typical United States isolate HIV-1.

It is another object of the present invention to provide diagnostic tests for the detection of HIV-1.

Various other objects and advantages of the present invention will become apparent from the drawings and the following description of the invention.

BRIEF DESCRIPTION OF THE DRAWINGS

FIGS. 2A–2H shows the DNA sequence representing the MN-PH1 genome (SEQ ID NO:1).

FIGS. 3A–3C shows the predicted amino acid sequence of the MN-PH1 envelope (env) protein (SEQ ID NO:2).

FIGS. 6A–6S shows the DNA sequence representing the MN-ST1 genome (SEQ ID NO:3) and the predicted amino acid sequence of the MN-ST1 genome and env protein (SEQ ID NO:4).

FIGS. 8A–8H shows the DNA sequence of the env gene of BA-L (SEQ ID NO:5).

FIGS. 9A–9C shows the predicted amino acid sequence of the BA-L env protein (SEQ ID NO:6).

DETAILED DISCLOSURE OF THE INVENTION

Figure 1:
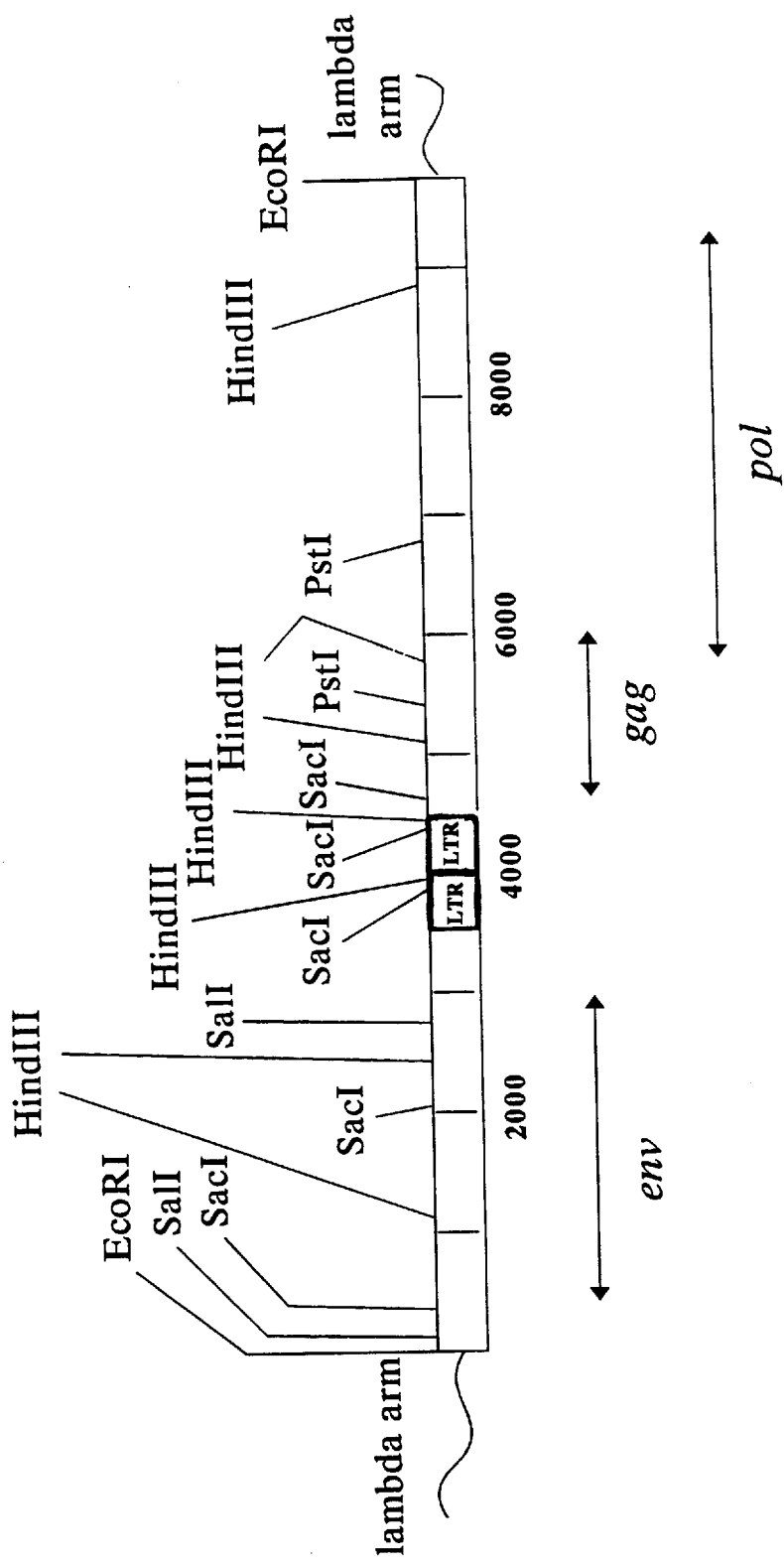
FIG. 1 shows the structure and restriction map of the lambda MN-PH1 clone.

The present invention relates to the HIV-1 virus strains, MN-ST1 and BA-L, which are more typical of the HIV-1 isolates found in the United States than previously known HIV-1 strains. Local isolates provide better material for vaccine and for the detection of the virus in biological samples, such as blood bank samples.

The present invention relates to DNA segments encoding the env protein of MN-ST1 or BA-L (the DNA sequence given in FIGS. 6A–6S and FIGS. 8A–8H, and shown in SEQ ID NO:3 and SEQ ID NO:5, respectively being two such examples) and to nucleotide sequences complementary to the segments referenced above as well as to other genes and nucleotide sequences contained in these clones. The present invention also relates to DNA segments encoding a unique portion of the MN-ST1 env protein or the BA-L env protein. (A "unique portion" consists of at least five (or six) amino acids or corresponding to at least 15 (or 18) nucleotides.)

The invention further relates to the HIV-1 virus strains MN-ST1 and BA-L themselves. The HIV-1 virus strains of the present invention are biologically active and can easily be isolated by one skilled in the art using known methodologies.

The above-described DNA segments of the present invention can be placed in DNA constructs which are then used in the transformation of host cells for generation of recombinantly produced viral proteins. DNA constructs of the present invention comprise a DNA segment encoding the env protein and the flanking region of MN-ST1 (or BA-L) or a portion thereof and a vector. The constructs can further comprise a second DNA segment encoding both a rev protein and a rev-responsive region of the env gene operably linked to the first DNA segment encoding the env protein. The rev protein facilitates efficient expression of the env protein in eucaryotic cells. Suitable vectors for use in the present invention include, but are not limited to, pSP72, lambda EMBL3 and SP65gpt.

Host cells to which the present invention relates are stably transformed with the above-described DNA constructs. The cells are transformed under conditions such that the viral protein encoded in the transforming construct is expressed. The host cell can be procaryotic (such as bacterial), lower eucaryotic (such as fungal, including yeast) or higher eucaryotic (such as mammalian). The host cells can be used to generate recombinantly produced MN-ST1 (or BA-L) env protein by culturing the cells in a manner allowing expression of the viral protein encoded in the construct. The recombinantly produced protein is easily isolated from the host cells using standard protein isolation protocols.

Since HIV-1 strains MN-ST1 and BA-L represent relatively typical United States genotypes, non-infectious MN-ST1 or BA-L proteins (for example, the env protein), peptides or unique portions of MN-ST1 or BA-L proteins (for example, a unique portion of the env protein), and even whole inactivated MN-ST1 or BA-L can be used as an immunogen in mammals, such as primates, to generate antibodies capable of neutralization and T cells capable of killing infected cells. The protein can be isolated from the virus or made recombinantly from a cloned envelope gene. Accordingly, the virus and viral proteins of the present invention are of value as either a vaccine or a component thereof, or an agent in immunotherapeutic treatment of individuals already infected with HIV-1.

As is customary for vaccines, a non-infectious antigenic portion of MN-ST1 or BA-L, for example, the env protein, can be delivered to a mammal in a pharmacologically acceptable carrier. The present invention relates to vaccines comprising non-infectious antigenic portions of either MN-ST1 or BA-L and vaccines comprising non-infectious antigenic portions of both MN-ST1 and BA-L. Vaccines of the present invention can include effective amounts of immunological adjuvants known to enhance an immune response. The viral protein or polypeptide is present in the vaccine in an amount sufficient to induce an immune response against the antigenic protein and thus to protect against HIV-1 infection. Protective antibodies are usually best elicited by a series of 2–3 doses given about 2 to 3 weeks apart. The series can be repeated when circulating antibody concentration in the patient drops.

Virus derived from the infectious HIV-1(MN) clones, MN-ST1, may also be used for reproducible challenge experiments in chimpanzees treated with candidate HIV-1 vaccines or in vitro with human antiserum from individuals treated with candidate vaccines. A candidate vaccine can be administered to a test mammal, such as a chimpanzee prior to or simultaneously with the infectious MN-ST1 virus of the present invention. Effectiveness of the vaccine can be determined by detecting the presence or absence of HIV-1 infection in the test mammals. Side-by-side comparative tests can be run by further administering to a second set of test mammals the virus alone and comparing the number of infections which develop in the two sets of test mammals. Alternatively, candidate vaccines can be evaluated in humans by administering the vaccine to a patient and then testing the ability of the MN-ST1 virus to infect blood cells from the patient.

The present invention also relates to the detection of HIV-1 virus in a biological sample. For detection of an HIV-1 infection the presence of the virus, proteins encoded in the viral genome, or antibodies to HIV-1 is determined. Many types of tests, as one skilled in the art will recognize, can be used for detection. Such tests include, but are not limited to, ELISA and RIA.

In one bioassay of the present invention all, or a unique portion, of the env protein is coated on a surface and contacted with the biological sample. The presence of a resulting complex formed between the protein and antibodies specific therefor in the serum can be detected by any of the known methods commonly used in the art, such as, for example, fluorescent antibody spectroscopy or colorimetry.

The following non-limiting examples are given to further demonstrate the present invention without being deemed limitative thereof.

EXAMPLES

MN-PH1 Clone

Figure 3A:
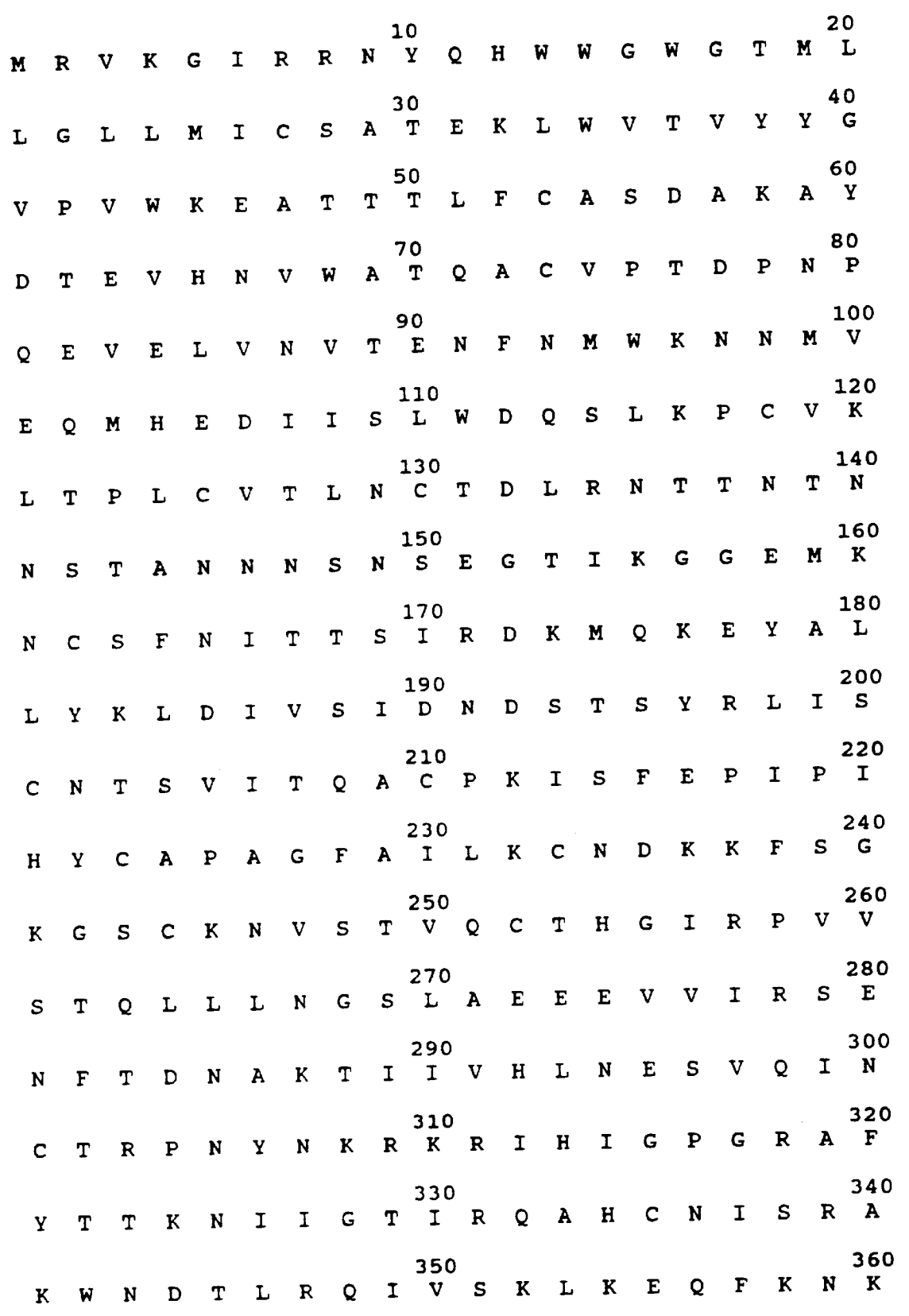
Figure 3B:
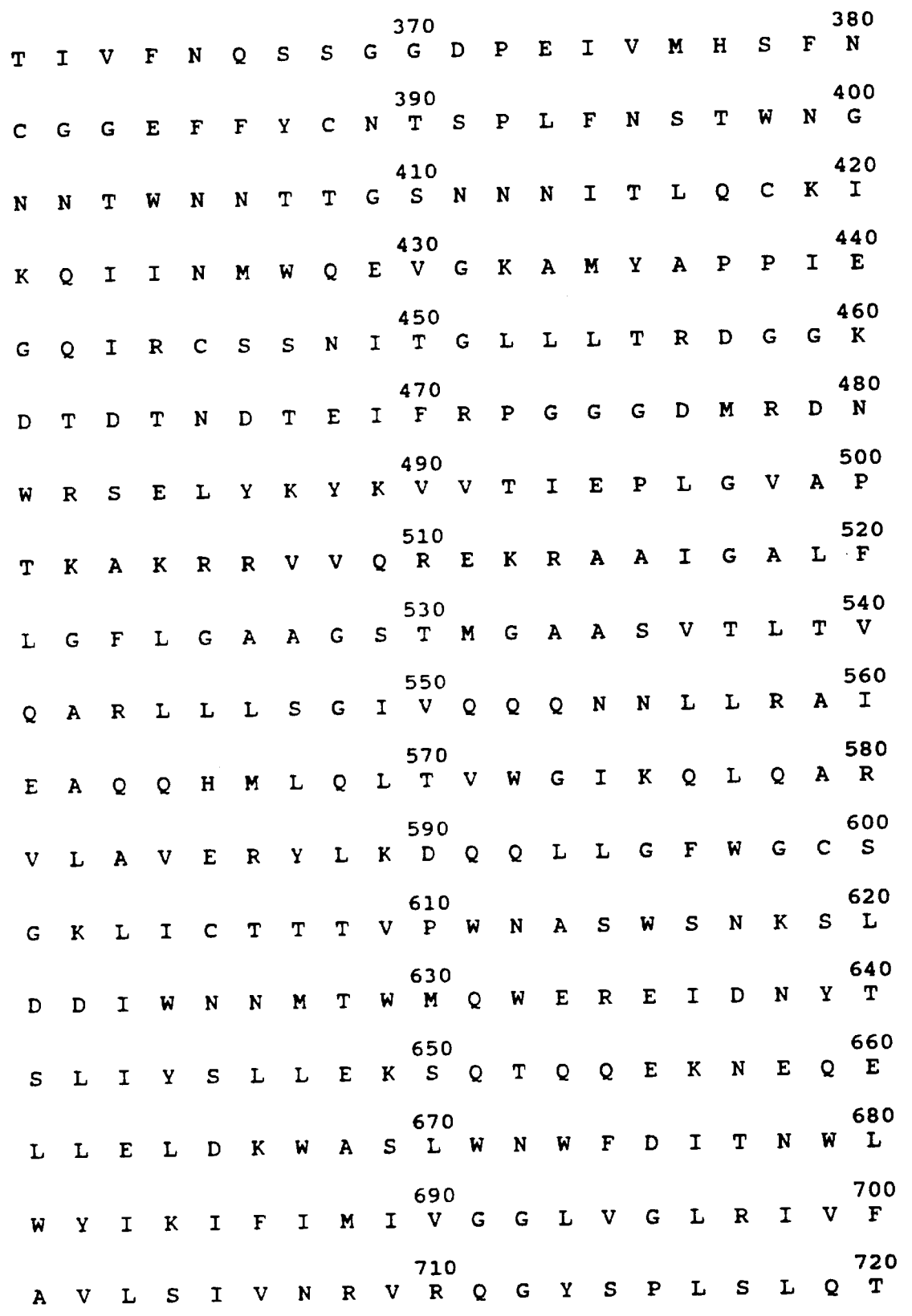
Figure 3C:
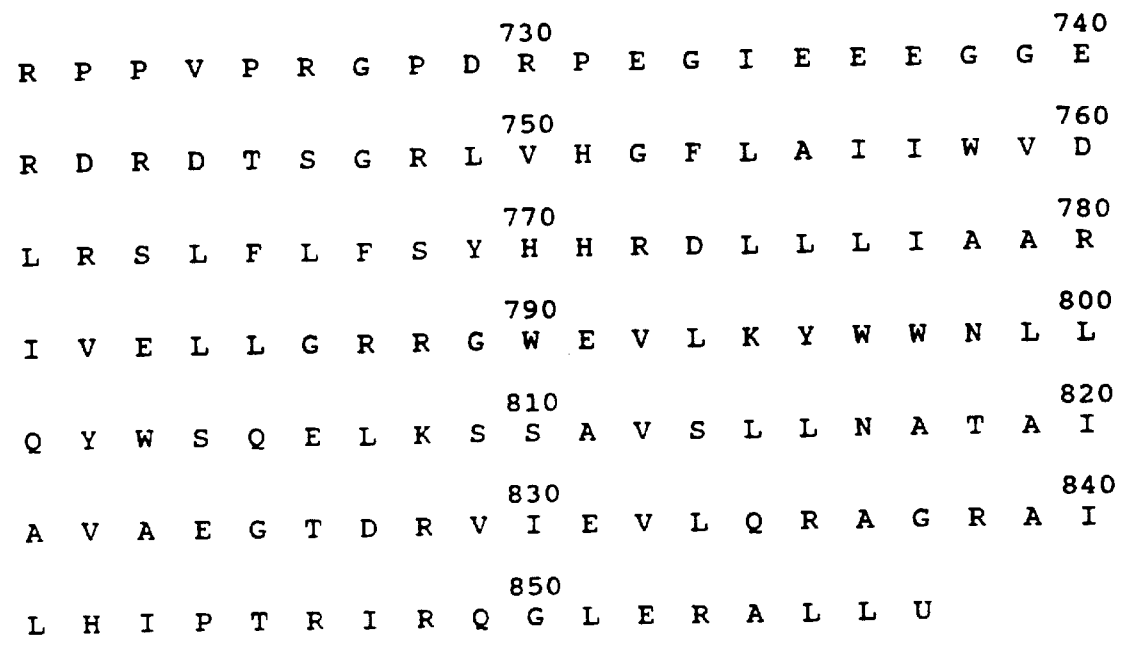
Figure 4:
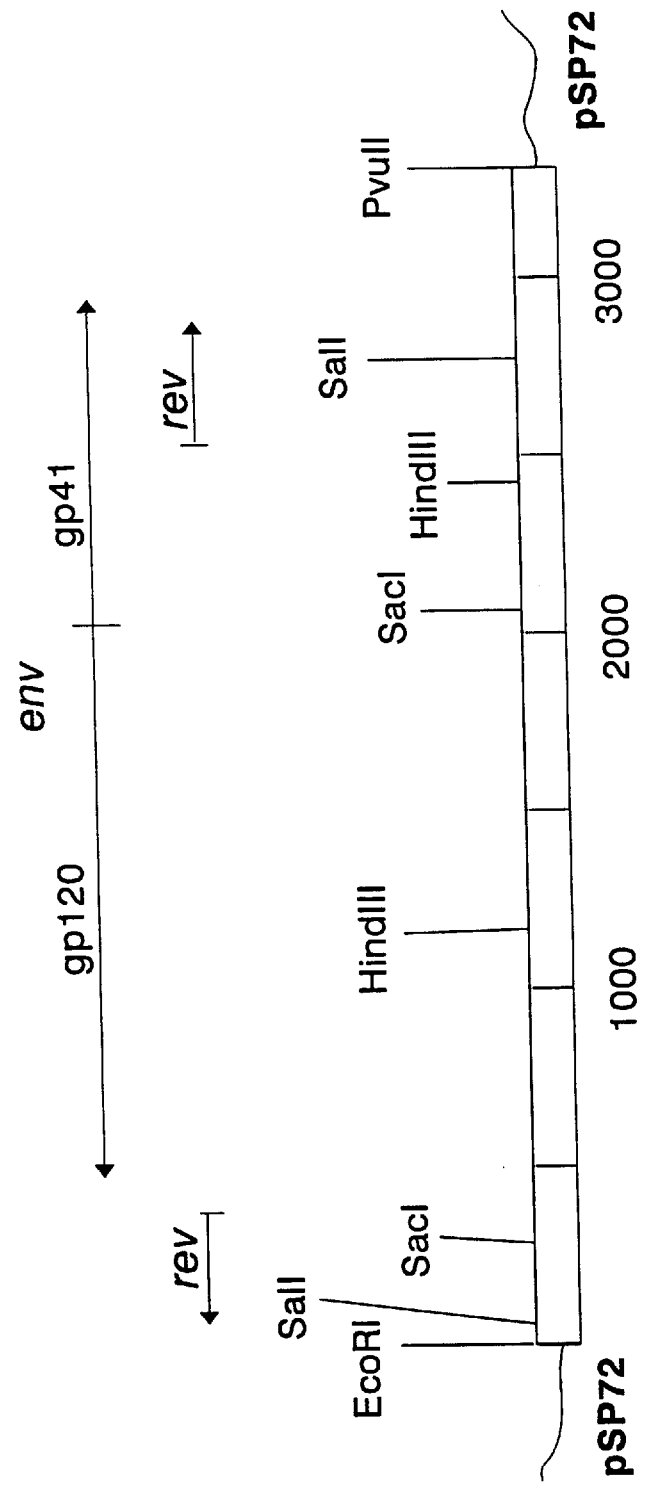
FIG. 4 shows the restriction map of the MN-PH1 envelope plasmid clone.

The permuted circular unintegrated viral DNA representing the complete HIV-1 (MN) genome was cloned by standard techniques (Sambrook et al., 1989, Molecular Cloning. Cold Spring Harbor, New York: Cold Spring Harbor Laboratory Press) into the Eco RI site of lambda gtWES.lambda B DNA from total DNA of H9 cells producing HIV-1 (MN). This clone is designated lambda MN-PH1, and its structure and restriction map are shown in FIG. 1. The clone was subcloned into M13mp18 and M13mp19, and the DNA sequence of the entire clone, given in FIGS. 2A–2H, and as shown in SEQ ID NO:1 was obtained by the dideoxy chain termination method (Sanger et al., Proc. Natl. Acad. Sci. U.S.A. 74, 5463–5467, 1977). The amino acid sequence of the envelope protein (see FIGS. 3A–3C, and as shown in SEQ ID NO:2) was inferred from the DNA sequence. A restriction map of the cloned unintegrated viral DNA (see FIG. 1) was also obtained from the DNA sequence of lambda PH1 and used in conjunction with the inferred amino acid sequence of the viral proteins to subclone the envelope (env) gene into the commercially available plasmid pSP72 (Promega Biological Research Products, Madison, Wis.), as shown in FIG. 4. This plasmid (pMN-PH1env) contains, in addition to the coding regions for the envelope proteins, the coding region for the rev protein (Feinberg et al., Cell 46, 807–817, 1986) and the portion of the env gene which contains the rev-responsive region (Dayton et al., J. Acquir. Immune. Defic. Syndr. 1, 441–452, 1988), since both are necessary for efficient expression of the envelope protein in eucaryotic cells. This plasmid thus contains all the elements required for production of envelope protein following placement into appropriate expression vectors and introduction into recipient cells, all by standard techniques known to molecular biologists.

MN-ST1 Clone

Figure 5:
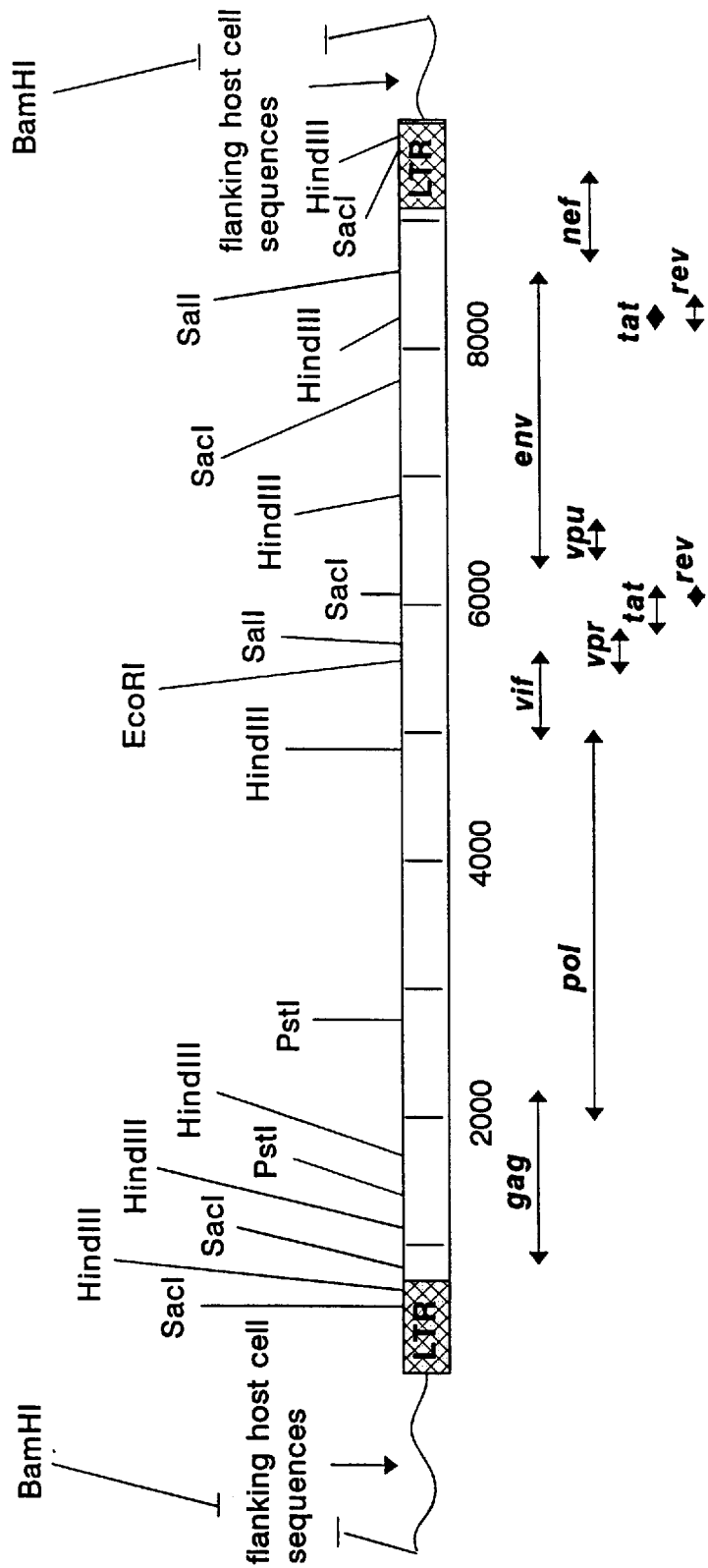
FIG. 5 shows the restriction map and structure of the lambda MN-ST1 clone.

The infectious molecular clone, lambda MN-ST1, was obtained by cloning integrated provirus from DNA purified from peripheral blood lymphocytes infected with HIV-1 (MN) and maintained in culture for a short time (one month). The integrated proviral DNA was partially digested with the restriction enzyme Sau3A under conditions which gave a maximum yield of DNA fragments of from 15–20 kilobases (kb). This was cloned into the compatible BamHI site of lambda EMBL3, as shown in FIG. 5. FIG. 5 also shows the restriction map of clone lambda MN-ST1. The DNA sequence of the entire clone, given in FIGS. 6A–6S, and shown in SEQ ID NO:3, was obtained by the dideoxy chain termination method (Sanger et al., Proc. Natl. Acad. Sci. U.S.A. 74, 5463–5467, 1977). The amino acid sequence was predicted from the DNA sequence (see FIGS. 6A–6S, and SEQ ID NO:4). This clone can be transfected into recipient cells by standard techniques. After transfection, the cloned proviral DNA is expressed into biologically active virus particles, which can be used as a source for virus stocks. The proviral DNA whose restriction map is shown in FIG. 4, was removed from the lambda phage vector by digestion with BamHI and inserted into a plasmid, SP65gpt (Feinberg et al., Cell 46, 807–817, 1986). This plasmid, pMN-ST1, contains an SV40 origin of replication. Consequently, transfection into COS-1 cells (Gluzman, Y. Cell 23, 175–182, 1981), which produce a SV40 gene product which interacts with the cognate origin of replication, results in a transient high plasmid copy number with a concomitant production of a large amount of replication competent, infectious virus (Feinberg et al., Cell 46, 807–817, 1986). This provides a convenient source of genetically homogeneous virus, as well as a way to introduce desired mutations using standard methods.

The envelope gene was excised from the lambda phage clone and cloned into plasmid as described above for lambda MN-PH1. This clone (pMN-ST1env), is similar to pMN-PH1env, described above, except that it derives from a biologically active cloned provirus. Like pMN-PH1env, it can be placed in a suitable vector and host to produce the envelope protein of HIV-1(MN) by well known techniques.

BA-L Clone

Figure 7:
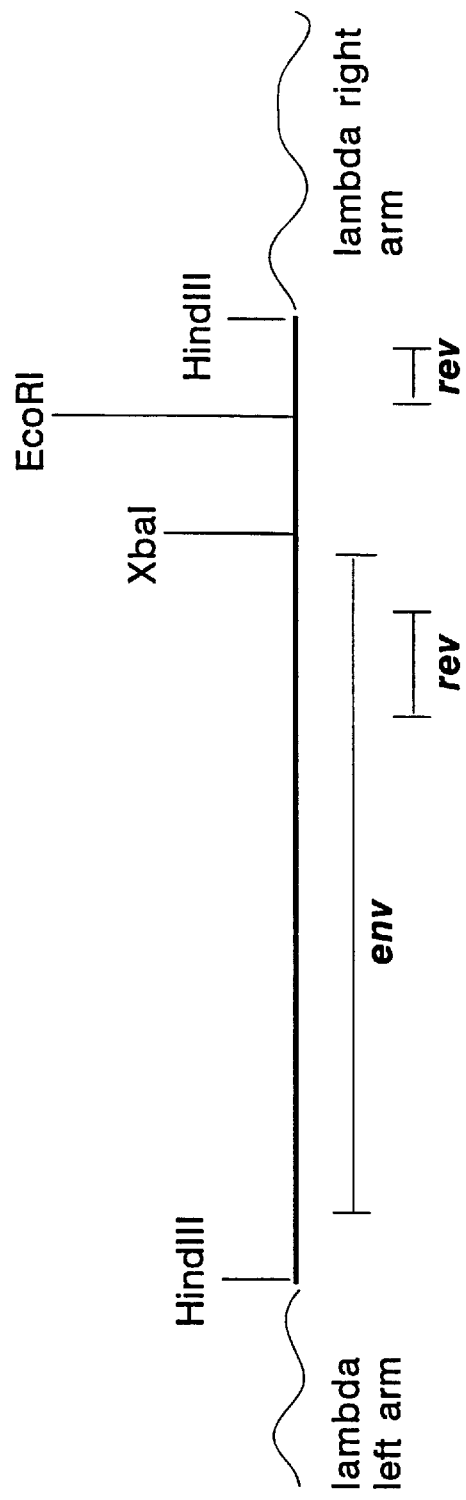
FIG. 7 shows the structure of the lambda BA-L clone.
Figure 10A:
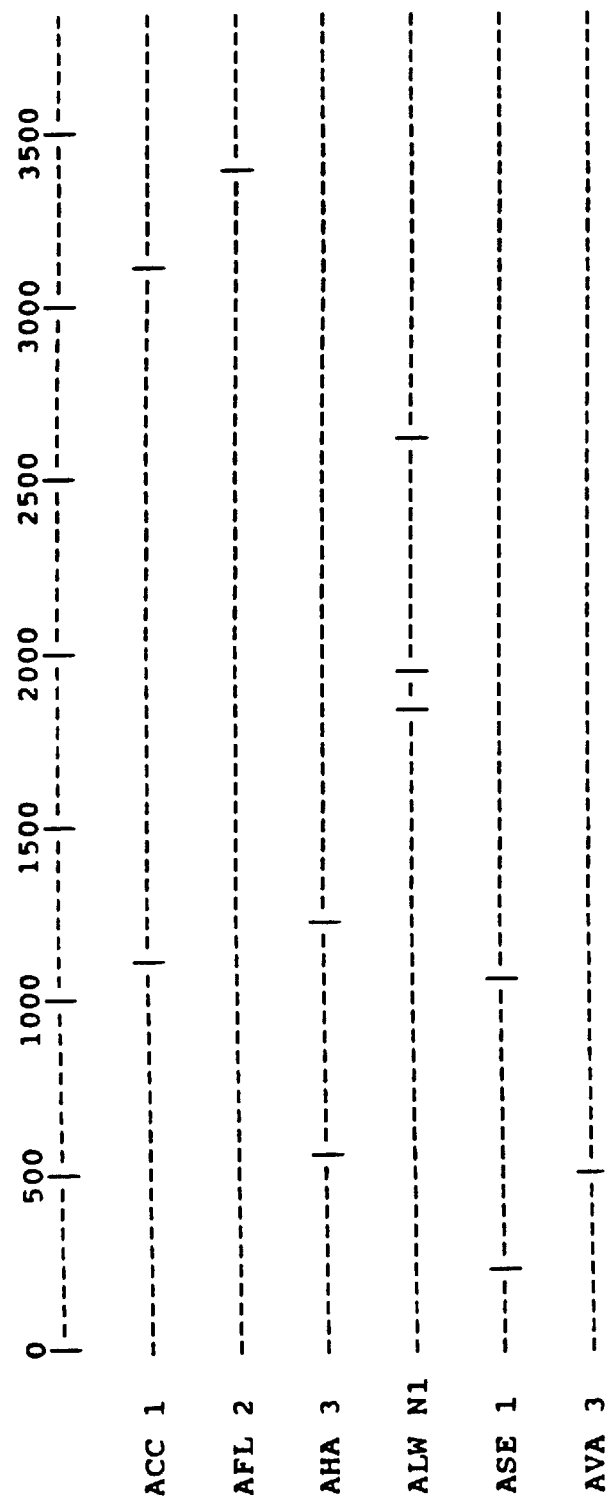
FIGS. 10A–10I shows the restriction map of the clone BA-L1.
Figure 10B:
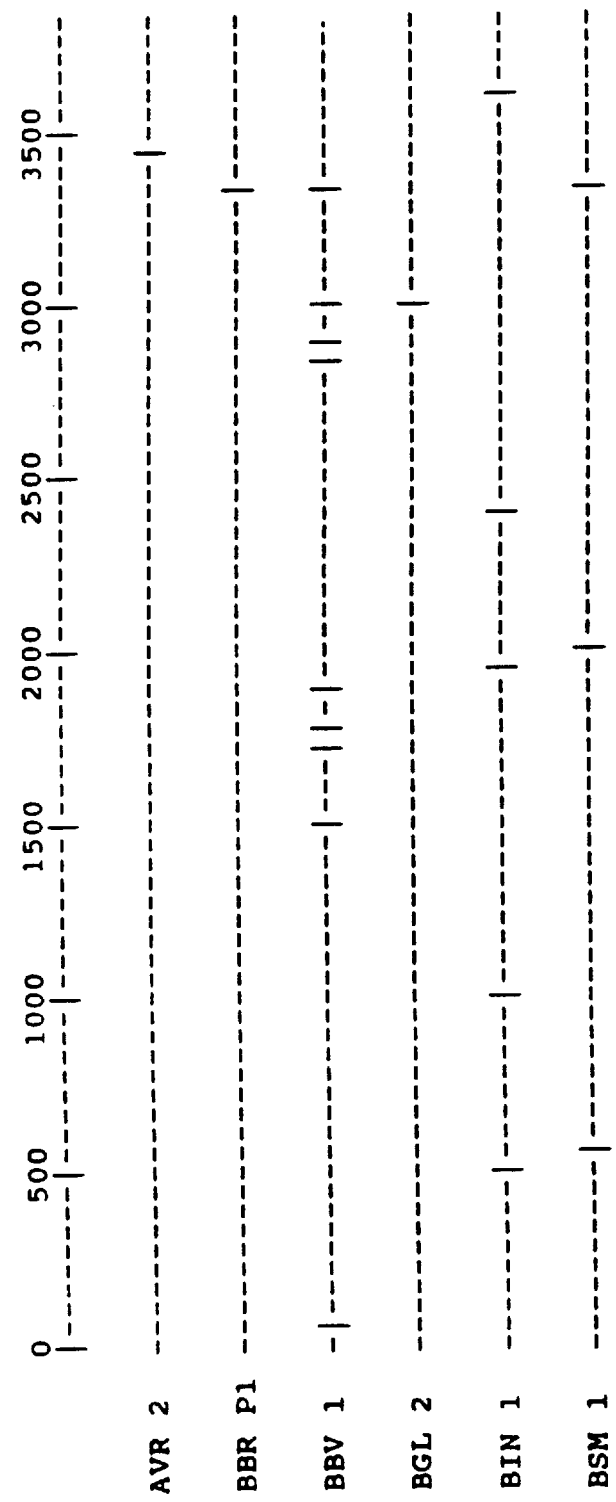
Figure 10C:
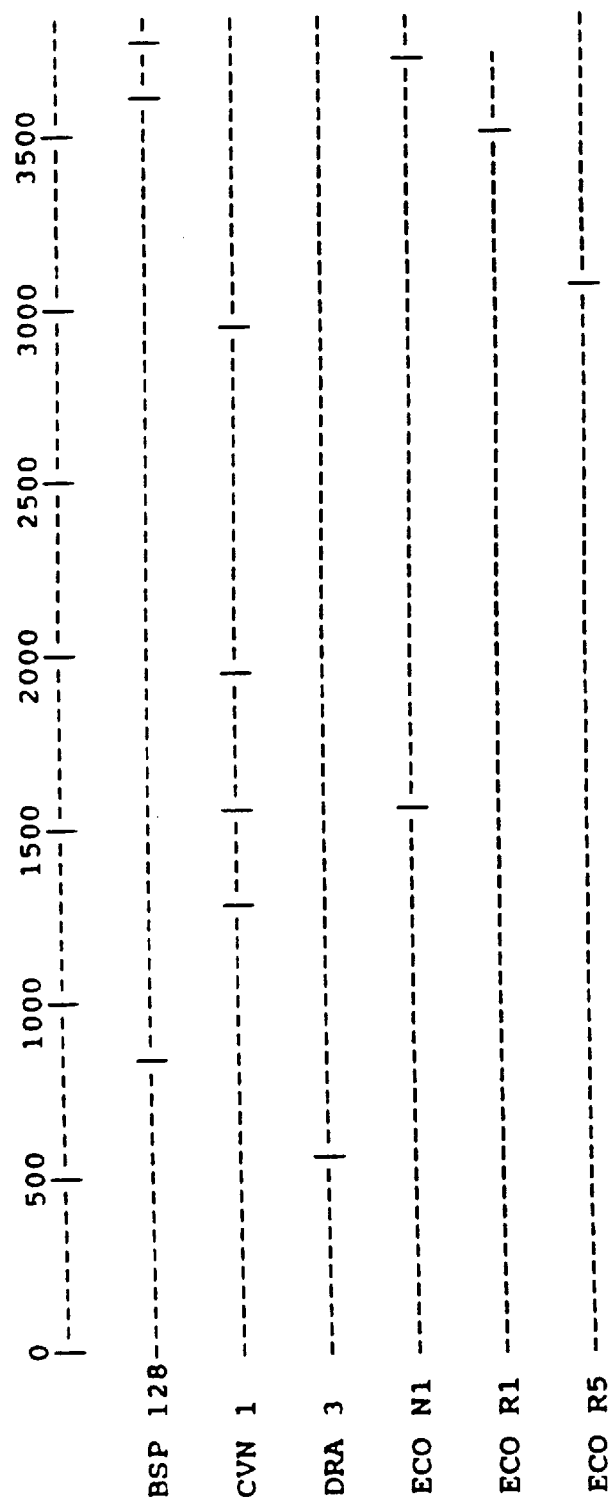
Figure 10D:
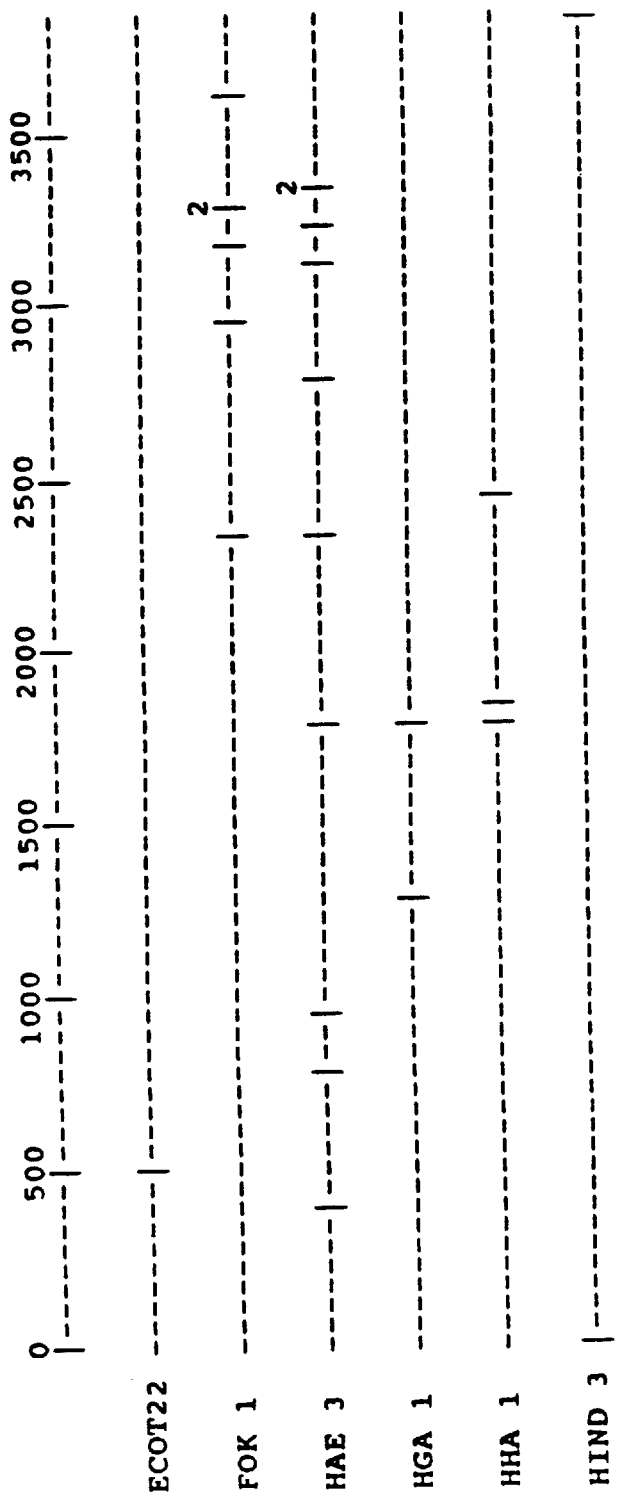
Figure 10E:
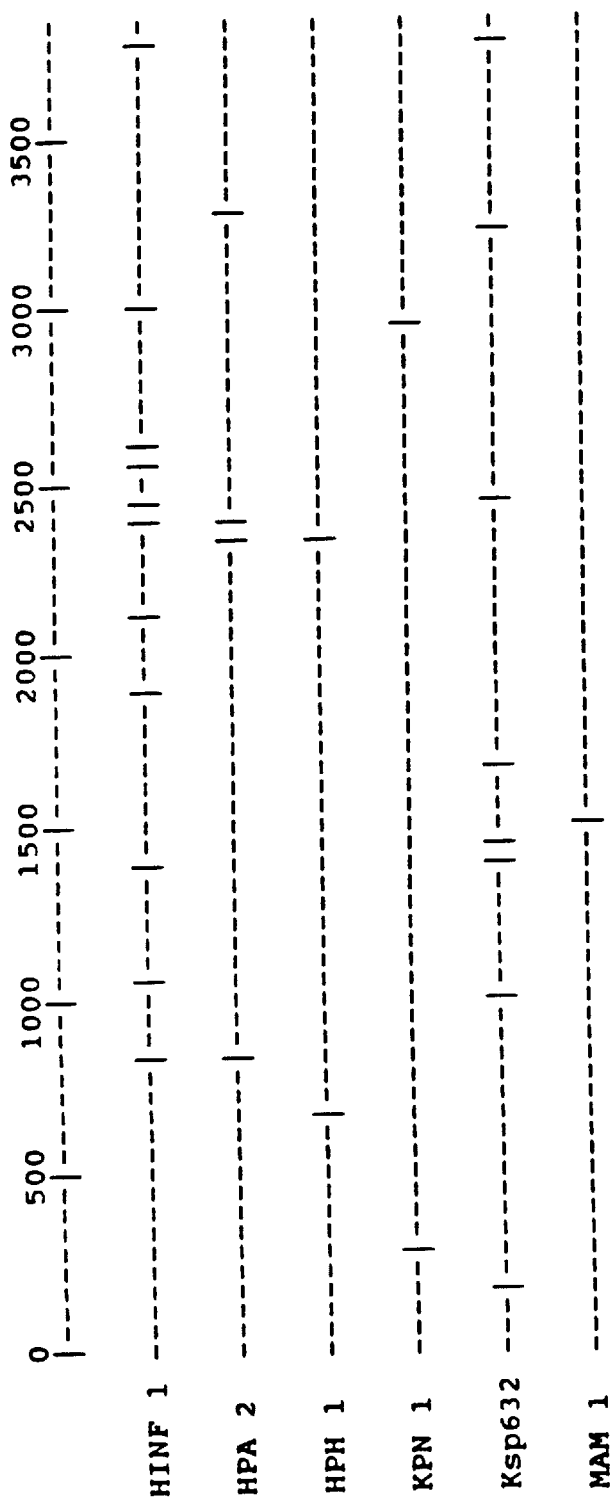
Figure 10F:
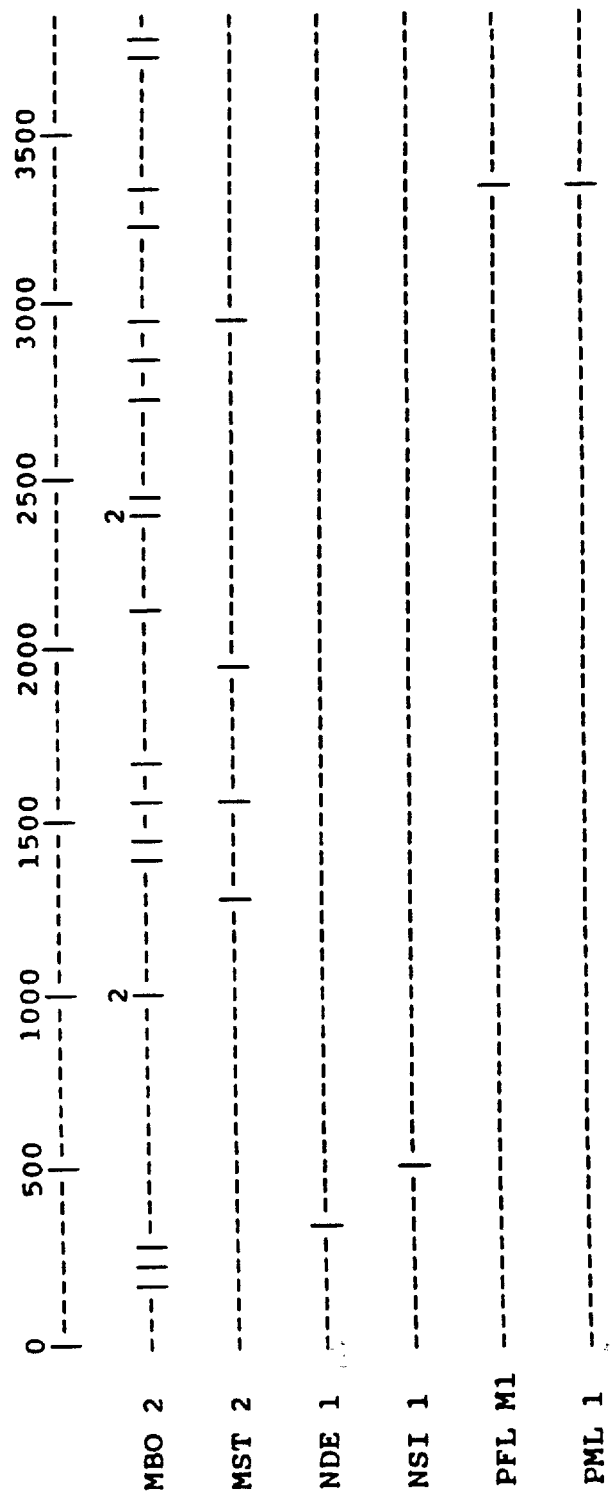
Figure 10G:
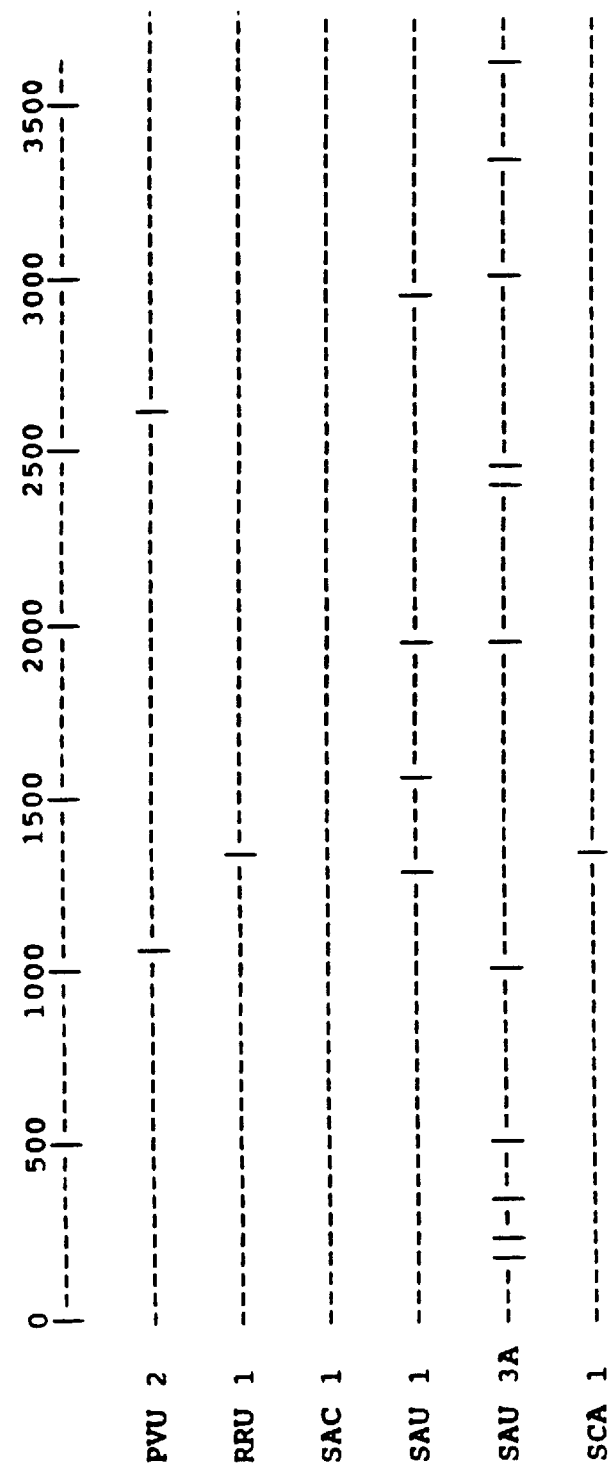
Figure 10H:
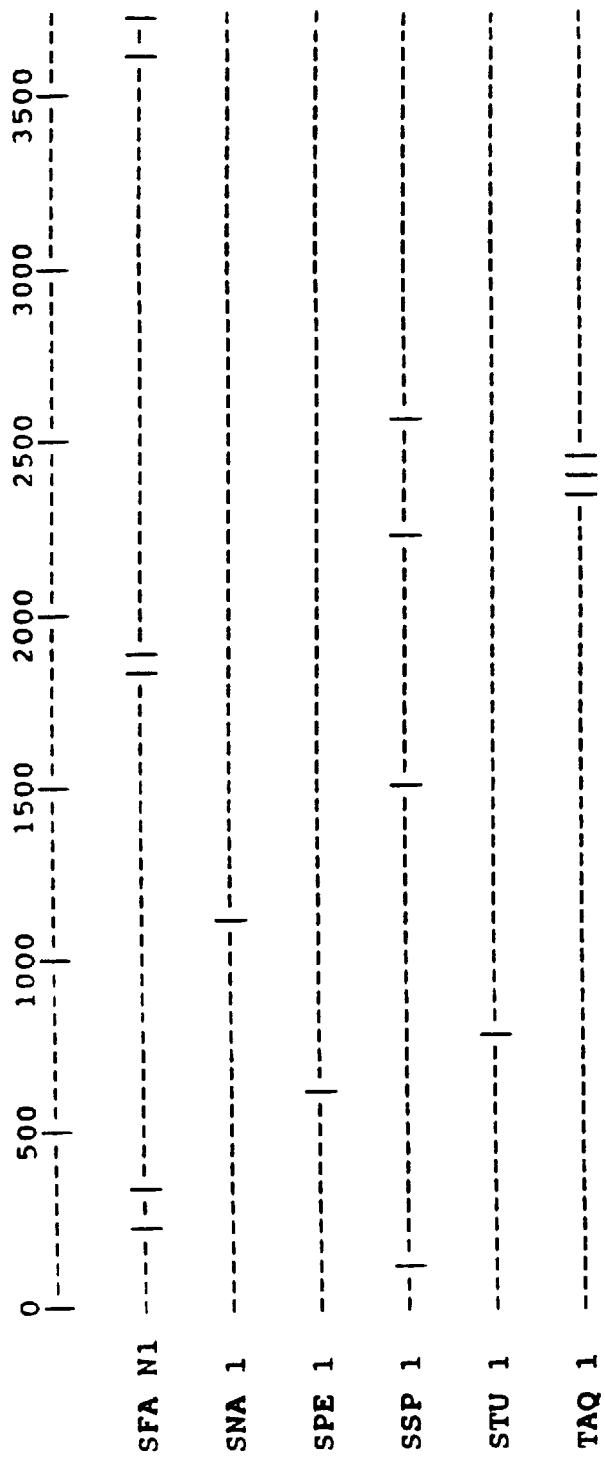
Figure 10I:
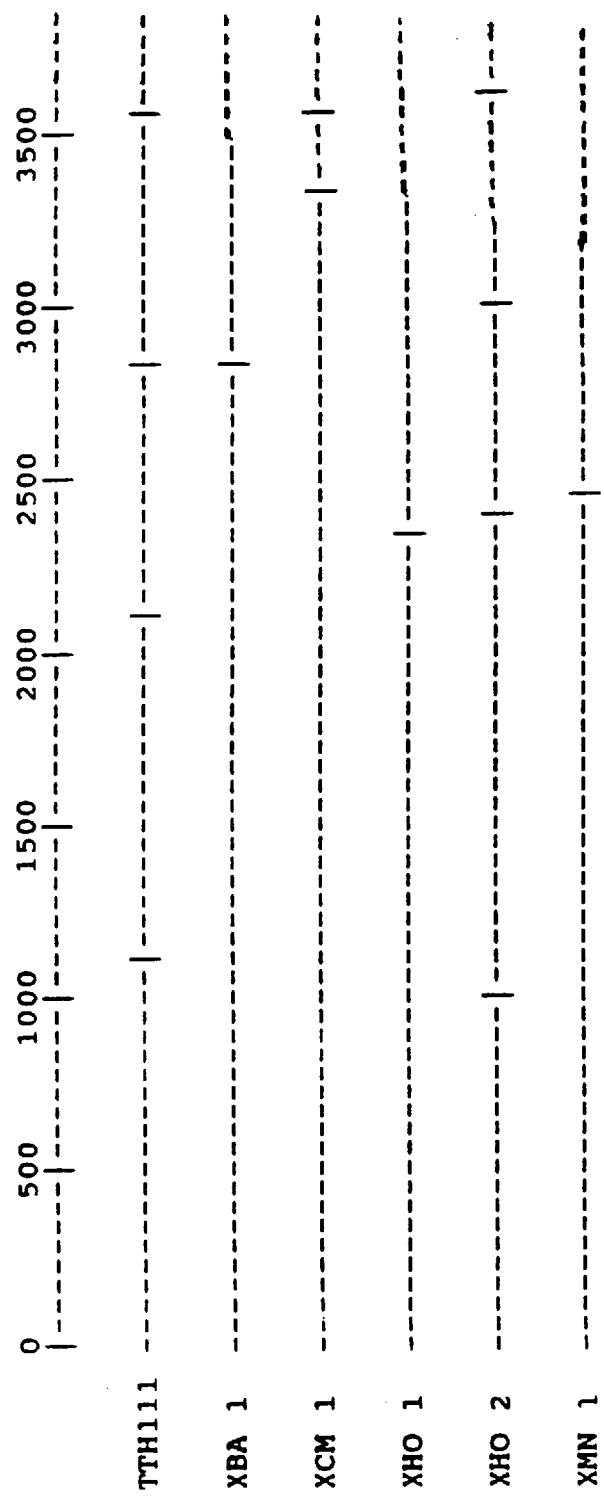

A Hind III fragment of unintegrated viral DNA representing the HIV-1(BA-L) genome was cloned by standard techniques into lambda phage Charon 28 DNA from total DNA of peripheral blood macrophages infected with and producing HIV-1(BA-L). A positive clone was selected by hybridization using a radiolabelled probe for the HIV-1 envelope. This clone, designated lambda BA-L1, was found to contain the entire gene for the envelope protein. Its structure is given in FIG. 7. The insert was transferred into a plasmid (pBluescript, Stratagene, LaJolle, Calif.) and the DNA sequence of the env gene was determined (see FIGS. 8A–8H). This clone is designated pBA-L1.

Figure 9A:
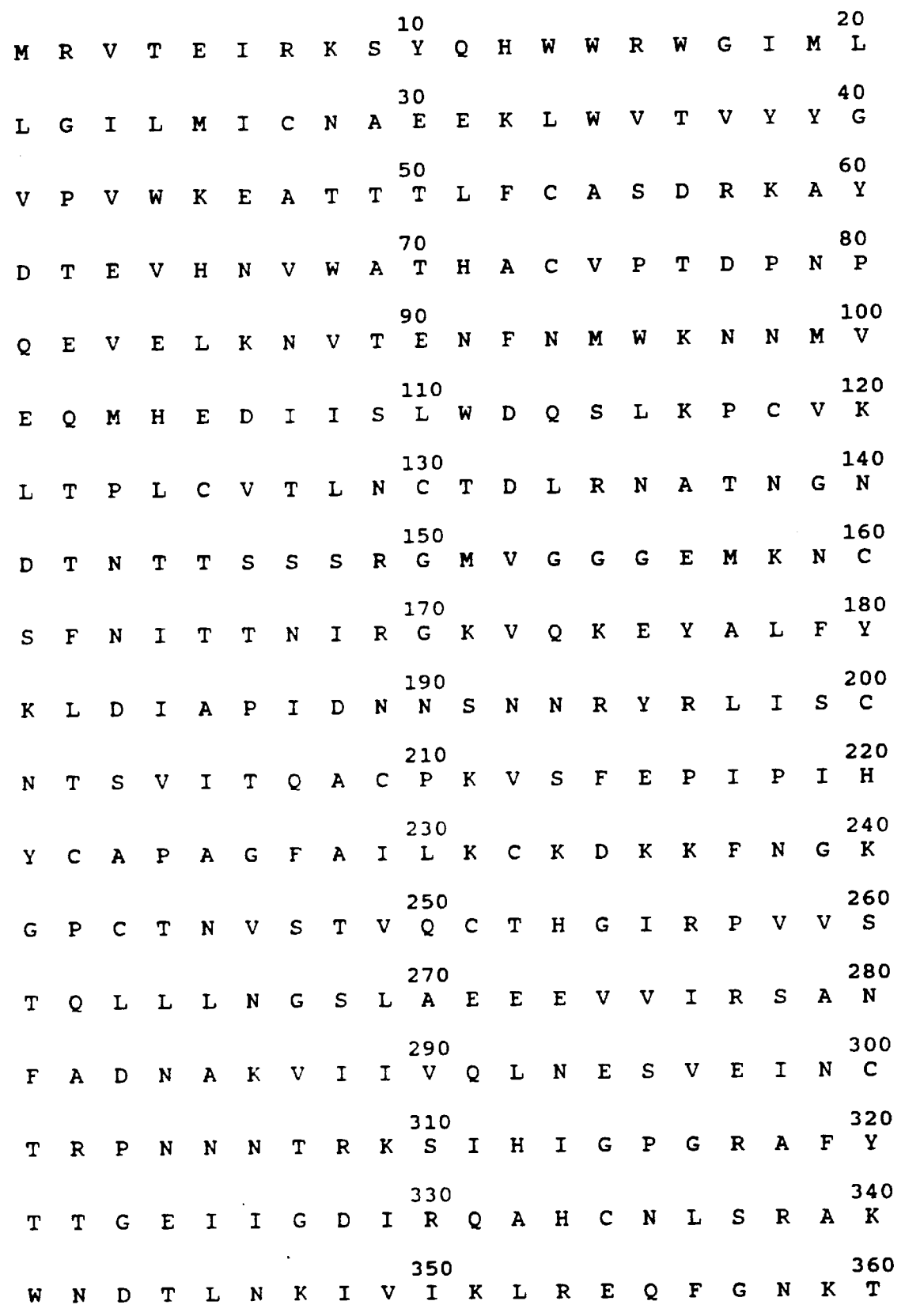
Figure 9B:
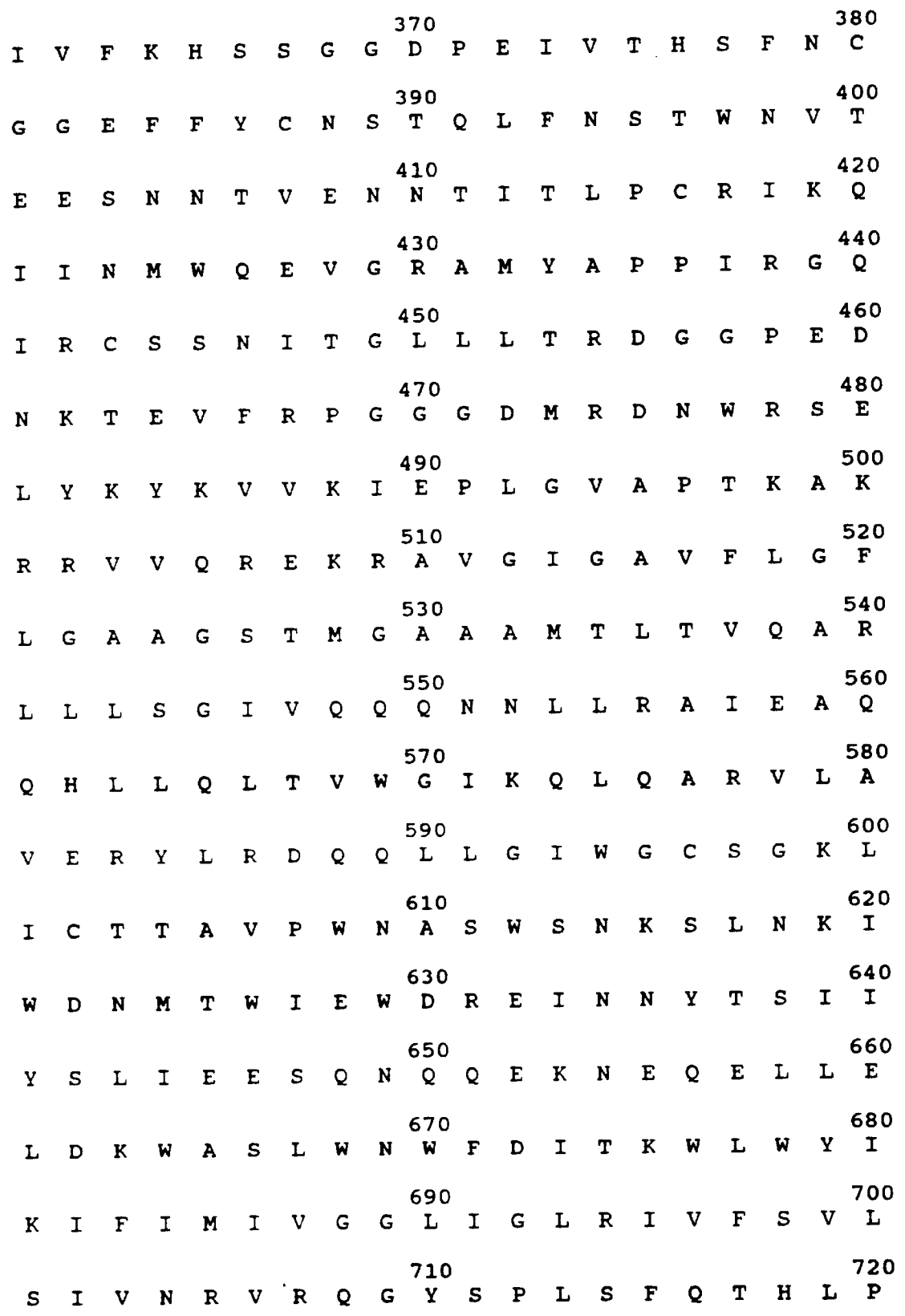
Figure 9C:
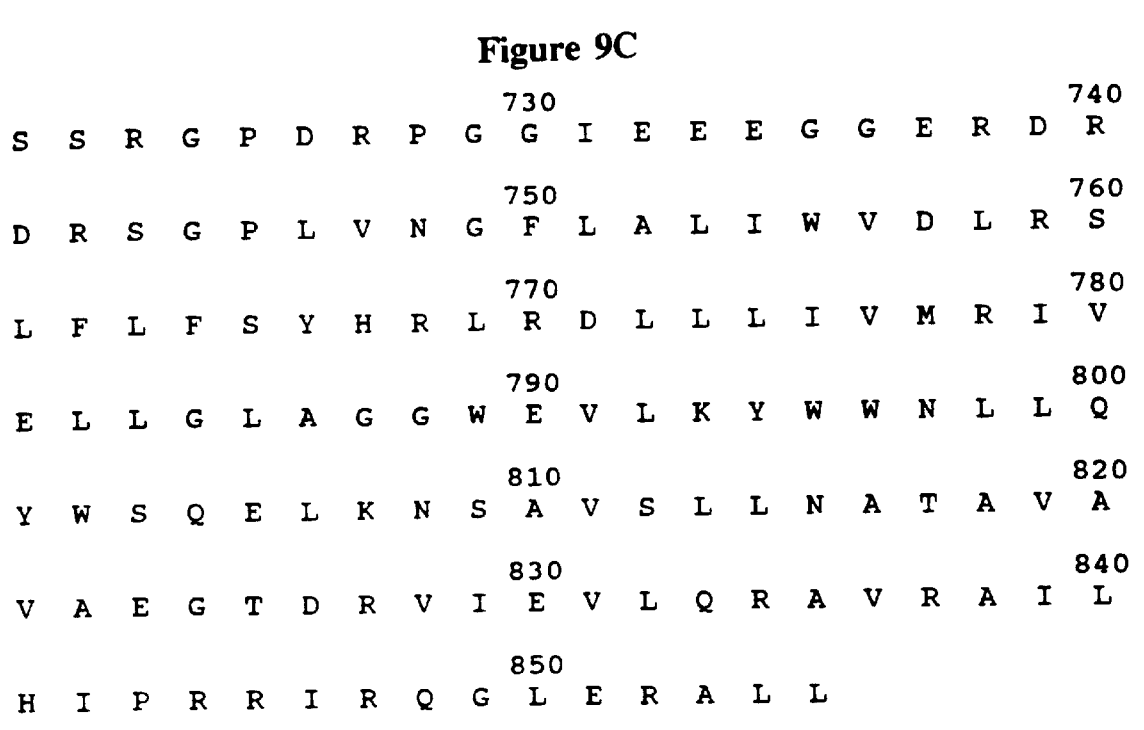

The amino acid sequence of the envelope protein, shown in FIGS. 9A–9C, and in SEQ ID NO:6, was inferred from the DNA sequence. A restriction map was also obtained from the DNA sequence of BA-L1 (shown in FIGS. 10A–10I) in order to determine the appropriate restriction enzyme sites for cloning the env gene into suitable expression vectors. An Eco RI-HindIII fragment of 0.4 Kb and a 2.8 Kb HindIII-XbaI fragment when cloned together constitute the entire env gene. This plasmid contains, in addition to the coding regions for the envelope proteins, the coding region for the rev protein and the portion of the env protein which contains the rev-responsive region. Both are necessary for efficient expression of the envelope protein in eucaryotic cells (Feinberg et al., Cell 46, 807–817, 1986; Dayton et al., J. Acquir. Immune. Defic. Syndr. 1, 441–452). This plasmid thus contains all the HIV-1 genetic elements required for production of envelope protein following placement into appropriate expression vectors and introduction into recipient cells, all by standard techniques well known in the art.

Statement of Deposit

The lambda MN-ST1 clone and the BA-L plasmid clone were deposited at the American Type Culture Collection (Rockville, Md.) under the terms of the Budapest Treaty. The lambda MN-ST1 clone has been assigned the ATCC accession number ATCC 40889 and the BA-L plasmid clone has been assigned the ATCC accession number ATCC 40890.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. Isolated and purified DNA having the envelope and rev coding sequences of HIV-1 strain BA-L having ATCC Accession No. 40890.

2. An isolated and purified DNA molecule of HIV-1 strain BA-L having the envelope gene sequence of SEQ ID NO:5.

3. Lambda BA-L molecular clone having the envelope and rev gene coding sequences of HIV-1 strain BA-L deposited under ATCC Accession No. 40890.

4. Isolated, cloned envelope DNA of HIV-1 strain BA-L consisting essentially of a HindIII to XbaI DNA fragment and an EcoRI to HindIII DNA fragment comprising the entire envelope gene of HIV-1 strain BA-L.

5. The DNA according to claim 4, wherein said HindIII to XbaI fragment is 2.8 kilobases and said EcoRI to HindIII fragment is 0.4 kilobases.

6. A vector comprising the HIV-1 BA-L DNA according to claim 1.

7. A vector comprising the HIV-1 BA-L DNA according to claim 2.

8. A vector comprising the HIV-1 BA-L DNA according to claim 4.

9. A host cell transfected or transformed with the vector according to claim 6.

10. A host cell transfected or transformed with the vector according to claim 7.

11. A host cell transfected or transformed with the vector according to claim 8.

12. A method of producing a recombinant entire envelope protein encoded by the complete envelope gene of HIV-1 strain BA-L DNA, comprising:

(a) culturing said host cells according to claim 9 under conditions allowing for expression of said viral envelope protein; and (b) isolating said expressed viral protein.

13. A method of producing a recombinant entire envelope protein encoded by the complete envelope gene of HIV-1 strain BA-L DNA, comprising:

(a) culturing said host cells according to claim 10 under conditions allowing for expression of Mid viral envelope protein; and (b) isolating said expressed viral protein.

14. A method of producing a recombinant entire envelope protein encoded by the complete envelope gene of HIV-1 strain BA-L DNA, comprising:

(a) culturing said host cells according to claim 11 under conditions allowing for expression of said viral envelope protein; and (b) isolating said expressed viral protein.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 9739 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 6240..8810

( x i ) SEQUENCE DESCRIPTION: SEQ ID NO:1:

```
TGGAAGGGCT   AATTCACTCC   CAACGAAGAC   AAGATATCCT              40
TGATCTGTGG   ATCTACCACA   CACAAGGCTA   CTTCCCTGAT              80
TAGCAGAACT   ACACACCAGG   GCCAGGGATC   AGATATCCAC             120
TGACCTTTGG   ATGGTGCTAC   AAGCTAGTAC   CAGTTGAGCC             160
AGAGAAGTTA   GAAGAAGCCA   ACAAAGGAGA   GAACACCAGC             200
TTGTTACACC   CTGTGAGCCT   GCATGGAATG   GATGACCCGG             240
AGAGAGAAGT   GTTAGAGTGG   AGGTTTGACA   GCCGCCTAGC             280
ATTTCATCAC   ATGGCCCGAG   AGCTGCATCC   GGAGTACTTC             320
AAGAACTGCT   GACATCGAGC   TTGCTACAAG   GGACTTTCCG             360
CTGGGGACTT   TCCAGGGAGG   CGTGGCCTGG   GCGGGACTGG             400
GGAGTGGCGA   GCCCTCAGAT   CCTGCATATA   AGCAGCTGCT             440
TTTTGCCTGT   ACTGGGTCTC   TCTGGTTAGA   CCAGATCTGA             480
GCCTGGGAGC   TCTCTGGCTA   ACTAGGGAAC   CCACTGCTTA             520
AGCCTCAATA   AAGCTTGCCT   TGAGTGCTTC   AAGTAGTGTG             560
TGCCCGTCTG   TTATGTGACT   CTGGTAGCTA   GAGATCCCTC             600
AGATCCTTTT   AGGCAGTGTG   GAAAATCTCT   AGCAGTGGCG             640
CCCGAACAGG   GACTTGAAAG   CGAAAGAAAA   ACCAGAGCTC             680
TCTCGACGCA   GGACTCGGCT   TGCTGAAGCG   CGCACGGCAA             720
GAGGCGAGGG   GCGGCGACTG   GTGAGTACGC   CAAAAATTCT             760
TGACTAGCGG   AGGCTAGAAG   GAGAGAGATG   GGTGCGAGAG             800
CGTCGGTATT   AAGCGGGGGA   GAATTAGATC   GATGGGAAAA             840
CATTCGGTTA   AGGCCAGGGG   GAAAGAAAAA   ATATAAATTA             880
AAACATGTAG   TATGGGCAAG   CAGGGAGCTA   GAACGATTCG             920
CAGTCAATCC   TGGCCTGTTA   GAAACATCAG   AAGGCTGTAG             960
ACAAATACTG   GGACAGCTAC   AACCATCCCT   TCAGACAGGA            1000
TCAGAAGAAC   TTAAATCATT   ATATAATACA   GTAGCAACCC            1040
TCTATTGTGT   GCATCAAAAG   ATAGAGATAA   AGACACCAA             1080
GGAAGCTTTA   GAGAAAATAG   AGGAAGAGCA   AAACAAAAGT            1120
AAGAAAAAAG   CACAGCAAGC   AGCAGCTGAC   ACAGGAAACA            1160
```

| | | | | |
|---|---|---|---|---|
| GAGGAAACAG | CAGCCAAGTC | AGCCAAAATT | ACCCCATAGT | 1200 |
| GCAGAACATC | GAGGGGCAAA | TGGTACATCA | GGCCATATCA | 1240 |
| CCTAGAACTT | TAAATGCATG | GGTAAAAGTA | GTAGAAGAGA | 1280 |
| AGGCTTTCAG | CCCAGAAGTA | ATACCCATGT | TTTCAGCATT | 1320 |
| ATCAGAAGGA | GCCACCCCAC | AAGATTTAAA | CACCATGCTA | 1360 |
| AACACAGTGG | GGGGACATCA | AGCAGCCATG | CAAATGTTAA | 1400 |
| AAGAGACCAT | CAATGAGGAA | GCTGCAGAAT | GGGATAGATT | 1440 |
| GCATCCAGTG | CATGCAGGGC | CTATTACACC | AGGCCAGATG | 1480 |
| AGAGAACCAA | GGGGAAGTGA | CATAGCAGGA | ACTACTAGTA | 1520 |
| CCCTTCAGGA | ACAAATAGGA | TGGATGACAA | ATAATCCACC | 1560 |
| TATCCCAGTA | GGAGAAATCT | ATAAAAGATG | GATAATCCTG | 1600 |
| GGATTAAATA | AAATAGTAAG | GATGTATAGC | CCTTCCAGCA | 1640 |
| TTCTGGACAT | AAGACAAGGA | CCAAAGGAAC | CCTTTAGAGA | 1680 |
| CTATGTAGAC | CGGTTCTATA | AAACTCTAAG | AGCCGAGCAA | 1720 |
| GCTTCACAGG | AGGTAAAAAA | CCGGACGACA | GAAACCTTGT | 1760 |
| TGGTCCAAAA | TGCGAACCCA | GATTGTAAGA | CTATTTTAAA | 1800 |
| AGCATTGGGA | CCAGCAGCTA | CACTAGAAGA | AATGATGACA | 1840 |
| GCATGTCAGG | GAGTGGGAGG | ACCTGGTCAT | AAAGCAAGAG | 1880 |
| TTTTGGCGGA | AGCGATGAGC | CAAGTAACAA | ATTCAGCTAC | 1920 |
| CATAATGATG | CAGAGAGGCA | ATTTTAGGAA | TCAAAGAAAG | 1960 |
| ATTATCAAGT | GCTTCAATTG | TGGCAAAGAA | GGGCACATAG | 2000 |
| CCAAAAATTG | CAGGGCCCCT | AGGAAAAGGG | CTGTTGGAA | 2040 |
| ATGTGGAAAG | GAAGGACACC | AAATGAAAGA | TTGTACTGAG | 2080 |
| AGACAGGCTA | ATTTTTTAGG | GAAGATCTGG | CCTTCCTGCA | 2120 |
| AGGGAAGGCG | GAATTTTCCT | CAGAGCAGAA | CAGAGCCAAC | 2160 |
| AGCCCCACCA | GAAGAGAGCT | TCAGGTTTGG | GGAAGAGACA | 2200 |
| ACAACTCCCT | ATCAGAAGCA | GGAGAAGAAG | CAGGAGACGA | 2240 |
| TAGACAAGGA | CCTGTATCCT | TTAGCTTCCC | TCAAATCACT | 2280 |
| CTTTGGCAAC | GACCCATTGT | CACAATAAAG | ATAGGGGGGC | 2320 |
| AACTAAAGGA | AGCTCTATTA | GATACAGGAG | CAGATGATAC | 2360 |
| AGTATTAGGA | GAAATGAATT | TGCCAAGAAG | ATGGAAACCA | 2400 |
| AAAATGATAG | GGGGAATTGG | AGGTTTTATC | AAAGTAAGAC | 2440 |
| AGTATGATCA | GATAACCATA | GGAATCTGTG | GACATAAAGC | 2480 |
| TATAGGTACA | GTATTAGTAG | GACCTACACC | TGTCAACATA | 2520 |
| ATTGGAAGAA | ATCTGTTGAC | TCAGCTTGGG | TGCACTTTAA | 2560 |
| ATTTTCCCAT | TAGTCCTATT | GAAACTGTAC | CAGTAAAATT | 2600 |
| AAAGCCAGGA | ATGGATGGCC | CAAAAGTTAA | ACAATGGCCA | 2640 |
| TTGACAGAAG | AAAAAATAAA | AGCATTAATA | GAAATTTGTA | 2680 |
| CAGAAATGGA | AAAGGAAGGG | AAAATTTCAA | AAATTGGGCC | 2720 |
| TGAAAATCCA | TACAATACTC | CAGTATTTGC | CATAAAGAAA | 2760 |

| | | | | |
|---|---|---|---|---|
| AAAGACAGTA | CTAAATGGAG | AAAATTAGTA | GATTTCAGAG | 2800 |
| AACTTAATAA | GAAAACTCAA | GACTTCTGGG | AAGTTCAATT | 2840 |
| AGGAATACCA | CATCCTGCAG | GGTTAAAAAA | GAAAAAATCA | 2880 |
| GTAACAGTAC | TGGATGTGGG | TGATGCATAT | TTTTCAGTTC | 2920 |
| CCTTAGATAA | AGACTTCAGG | AAGTATACTG | CATTTACCAT | 2960 |
| ACCTAGTATA | AACAATGAAA | CACCAGGGAT | TAGATATCAG | 3000 |
| TACAATGTGC | TTCCACAGGG | ATGGAAAGGA | TCACCAGCAA | 3040 |
| TATTCCAAAG | TAGCATGACA | AAAATCTTAG | AGCCTTTTAG | 3080 |
| AAAACAAAAT | CCAGACATAG | TTATCTATCA | ATACATGGAT | 3120 |
| GATTTGTATG | TAGGATCTGA | CTTAGAAATA | GGGCAGCATA | 3160 |
| GAGCAAAAAT | AGAGGAACTG | AGACGACATC | TGTTGAGGTG | 3200 |
| GGGATTTACC | ACACCAGACA | AAAACATCA | GAAAGAACCT | 3240 |
| CCATTCCTTT | GGATGGGTTA | TGAACTCCAT | CCTGATAAAT | 3280 |
| GGACAGTACA | GCCTATAGTG | CTACCAGAAA | AAGACAGCTG | 3320 |
| GACTGTCAAT | GACATACAGA | AGTTAGTGGG | AAAATTGAAT | 3360 |
| TGGGCAAGTC | AGATTTACGC | AGGGATTAAA | GTAAAGCAAT | 3400 |
| TATGTAAACT | CCTTAGAGGA | ACCAAAGCAC | TAACAGAAGT | 3440 |
| AATACCACTA | ACAGAAGAAG | CAGAGCTAGA | ACTGGCAGAA | 3480 |
| AACAGGGAAA | TTCTAAAAGA | ACCAGTACAT | GGAGTGTATT | 3520 |
| ATGACCCATC | AAAAGACTTA | ATAGCAGAAG | TACAGAAGCA | 3560 |
| GGGGCAAGGC | CAATGGACAT | ATCAAATTTA | TCAAGAGCCA | 3600 |
| TTTAAAAATC | TGAAAACAGG | CAAATATGCA | AGAATGAGGG | 3640 |
| GTGCCCACAC | TAATGATGTA | AAACAATTAA | CAGAGGCAGT | 3680 |
| GCAAAAAATA | GCCACAGAAA | GCATAGTAAT | ATGGGGAAAG | 3720 |
| ACTCCTAAAT | TTAGACTACC | CATACAAAAA | GAAACATGGG | 3760 |
| AAACATGGTG | GACAGAGTAT | ACGTAAGCCA | CCTGGATTCC | 3800 |
| TGAGTGGGAG | GTTGTCAATA | CCCCTCCCTT | AGTGAAATTA | 3840 |
| TGGTACCAGT | TAGAGAAAGA | ACCCATAGTA | GGTGCAGAAA | 3880 |
| CTTTCTATGT | AGATGGGGCA | GCTAACAGGG | AGACTAAAAA | 3920 |
| AGGAAAAGCA | GGATATGTTA | CTAACAGAGG | AAGACAAAAG | 3960 |
| GTTGTCTCCC | TAACTGACAC | AACAAATCAG | AAGACTGAGT | 4000 |
| TACAAGCAAT | TCATCTAGCT | TTGCAAGATT | CAGGGTTAGA | 4040 |
| AGTAAACATA | GTAACAGACT | CACAATATGC | ATTAGGAATC | 4080 |
| ATTCAAGCAC | AACCAGATAA | AAGTGAATCA | GAGTTAGTCA | 4120 |
| GTCAAATAAT | AGAGCAGTTA | ATAAAAAAGG | AAAAGGTCTA | 4160 |
| TCTGGCATGG | GTACCAGCAC | ACAAAGGAAT | TGGAGGAAAT | 4200 |
| GAACAAGTAG | ATAAATTAGT | CAGTGCTGGA | ATCAGGAAAG | 4240 |
| TACTATTTTT | AGATGGAATA | GATAAGGCCC | AAGAAGACCA | 4280 |
| TGAGAAATAT | CACAGTAATT | GGAGAGCAAT | GGCTAGTGAC | 4320 |
| TTTAACCTAC | CACCTATAGT | AGCAAAAGAA | ATAGTAGCCA | 4360 |

| | | | | |
|---|---|---|---|---|
| GCTGTGATAA | ATGTCAGCTA | AAAGGAGAAG | CCATGCATGG | 4400 |
| ACAAGTAGAC | TGTAGTCCAG | GAATATGGCA | ACTAGATTGT | 4440 |
| ACACATTTAG | AAGGAAAAGT | TATCCTGGTA | GCAGTTCATG | 4480 |
| TAGCCAGTGG | ATACATAGAA | GCAGAAGTTA | TTCCAGCAGA | 4520 |
| GACAGGGCAG | GAGACAGCAT | ACTTTCTCTT | AAAATTAGCA | 4560 |
| GGAAGATGGC | CAGTAAAAAC | AATACATACA | GACAATGGCC | 4600 |
| CCAATTTCAC | CAGTACTACG | GTTAAGGCCG | CCTGTTGGTG | 4640 |
| GACGGGAATC | AAGCAGGAAT | TTGGCATTCC | CTACAATCCC | 4680 |
| CAAAGTCAAG | GAGTAATAGA | ATCTATGAAT | AAAGAATTAA | 4720 |
| AGAAAATTAT | AGGACAGGTA | AGAGATCAGG | CTGAACATCT | 4760 |
| TAAGAGAGCA | GTACAAATGG | CAGTATTCAT | CCACAATTTT | 4800 |
| AAAAGAAAAG | GGGGGATTGG | GGGGTACAGT | GCAGGGGAAA | 4840 |
| GAATAGTAGG | CATAATAGCA | ACAGACATAC | AAACTAAAGA | 4880 |
| ACTACAAAAA | CAAATTACAA | AAATTCAAAA | TTTTCGGGTT | 4920 |
| TATTACAGGG | ACAGCAGAGA | TCCACTTTGG | AAAGGACCAG | 4960 |
| CAAAGCTTCT | CTGGAAAGGT | GAAGGGGCAG | TAGTAATACA | 5000 |
| AGATAATAAT | GACATAAAAG | TAGTGCCAAG | AAGAAAAGCA | 5040 |
| AAGGTCATTA | GGGATTATGG | AAAACAGACG | GCAGGTGATG | 5080 |
| ATTGTGTGGC | AAGCAGACAG | GATGAGGATT | AGAACATGGA | 5120 |
| AAAGTTTAGT | AAAACACCAT | ATGTATATTT | CAAAGAAAGC | 5160 |
| TAAAGGACGG | TTTTATAGAC | ATCACTATGA | AAGCACTCAT | 5200 |
| CCAAGAATAA | GTTCAGAAGT | ACACATCCCA | CTAGGGGATG | 5240 |
| CTAGATTGGT | AATAACAACA | TATTGGGGTC | TGCATACAGG | 5280 |
| AGAAAGAGAC | TGGCATTTAG | GTCAGGGAGT | CTCCATAGAA | 5320 |
| TGGAGGAAAA | AGAGATATAG | CACACAAGTA | GACCCTGACC | 5360 |
| TAGCAGACCA | CCTAATTCAT | CTGCATTACT | TTGATTGTTT | 5400 |
| TTCAGACTCT | GCCATAAGAA | AGGCCATATT | AGGACATAGA | 5440 |
| GTTAGTCCTA | TTTGTGAATT | TCAAGCAGGA | CATAACAAGG | 5480 |
| TAGGACCTCT | ACAGTACTTG | GCACTAACAG | CATTAATAAC | 5520 |
| ACCAAAAAAG | ATAAAGCCAC | CTTTGCCTAG | TGTTAAGAAA | 5560 |
| CTGACAGAGG | ATAGATGGAA | CAAGCCCCAG | AAGACCAAGG | 5600 |
| GCCACAGAGG | GAGCCATACA | ATCAATGGGC | ACTAGAGCTT | 5640 |
| TTAGAGGAGC | TTAAGAATGA | AGCTGTTAGA | CATTTTCCTA | 5680 |
| GGATATGGCT | CCATGGCTTA | GGGCAACATA | TCTATGAAAC | 5720 |
| TTATGGGGAT | ACTTGGGCAG | GAGTGGAAGC | CATAATAAGA | 5760 |
| ATTCTACAAC | AACTGCTGTT | TATTCATTTC | AGAATTGGGT | 5800 |
| GTCGACATAG | CAGAATAGGC | ATTATTCGAC | AGAGGAGAGC | 5840 |
| AAGAAATGGA | GCCAGTAGAT | CCTAGACTAG | AGCCCTGGAA | 5880 |
| GCATCCAGGA | AGTCAGCCTA | AGACTGCTTG | TACCACTTGC | 5920 |
| TATTGTAAAA | AGTGTTGCTT | TCATTGCCAA | GTTTGTTTCA | 5960 |

-continued

| | | | | |
|---|---|---|---|---|
| CAAAAAAAGC | CTTAGGCATC | TCCTATGGCA | GGAAGAAGCG | 6000 |
| GAGACAGCGA | CGAAGAGCTC | CTGAAGACAG | TCAGACTCAT | 6040 |
| CAAGTTTCTC | TACCAAAGCA | GTAAGTAGTA | CATGTAATGC | 6080 |
| AACCTTTAGT | AATAGCAGCA | ATAGTAGCAT | TAGTAGTAGC | 6120 |
| AGGAATAATA | GCAATAGTTG | TGTGATCCAT | AGTATTCATA | 6160 |
| GAATATAGGA | AAATAAGAAG | ACAAGAAAA | ATAGACAGGT | 6200 |
| TAATTGATAG | AATAAGCGAA | AGAGCAGAAG | ACAGTGGCAA | 6240 |
| TGAGAGTGAA | GGGGATCAGG | AGGAATTATC | AGCACTGGTG | 6280 |
| GGGATGGGGC | ACGATGCTCC | TTGGGTTATT | AATGATCTGT | 6320 |
| AGTGCTACAG | AAAAATTGTG | GGTCACAGTC | TATTATGGGG | 6360 |
| TACCTGTGTG | GAAAGAAGCA | ACCACCACTC | TATTTTGTGC | 6400 |
| ATCAGATGCT | AAAGCATATG | ATACAGAGGT | ACATAATGTT | 6440 |
| TGGGCCACAC | AAGCCTGTGT | ACCCACAGAC | CCCAACCCAC | 6480 |
| AAGAAGTAGA | ATTGGTAAAT | GTGACAGAAA | ATTTTAACAT | 6520 |
| GTGGAAAAAT | AACATGGTAG | AACAGATGCA | TGAGGATATA | 6560 |
| ATCAGTTTAT | GGGATCAAAG | CCTAAAGCCA | TGTGTAAAAT | 6600 |
| TAACCCCACT | CTGTGTTACT | TTAAATTGCA | CTGATTTGAG | 6640 |
| GAATACTACT | AATACCAATA | ATAGTACTGC | TAATAACAAT | 6680 |
| AGTAATAGCG | AGGGAACAAT | AAAGGGAGGA | GAAATGAAAA | 6720 |
| ACTGCTCTTT | CAATATCACC | ACAAGCATAA | GAGATAAGAT | 6760 |
| GCAGAAAGAA | TATGCACTTC | TTTATAAACT | TGATATAGTA | 6800 |
| TCAATAGATA | ATGATAGTAC | CAGCTATAGG | TTGATAAGTT | 6840 |
| GTAATACCTC | AGTCATTACA | CAAGCTTGTC | CAAAGATATC | 6880 |
| CTTTGAGCCA | ATTCCCATAC | ACTATTGTGC | CCCGGCTGGT | 6920 |
| TTTGCGATTC | TAAAATGTAA | CGATAAAAAG | TTCAGTGGAA | 6960 |
| AAGGATCATG | TAAAAATGTC | AGCACAGTAC | AATGTACACA | 7000 |
| TGGAATTAGG | CCAGTAGTAT | CAACTCAACT | GCTGTTAAAT | 7040 |
| GGCAGTCTAG | CAGAAGAAGA | GGTAGTAATT | AGATCTGAGA | 7080 |
| ATTTCACTGA | TAATGCTAAA | ACCATCATAG | TACATCTGAA | 7120 |
| TGAATCTGTA | CAAATTAATT | GTACAAGACC | CAACTACAAT | 7160 |
| AAAAGAAAAA | GGATACATAT | AGGACCAGGG | AGAGCATTTT | 7200 |
| ATACAACAAA | AAATATAATA | GGAACTATAA | GACAAGCACA | 7240 |
| TTGTAACATT | AGTAGAGCAA | AATGGAATGA | CACTTTAAGA | 7280 |
| CAGATAGTTA | GCAAATTAAA | AGAACAATTT | AAGAATAAAA | 7320 |
| CAATAGTCTT | TAATCAATCC | TCAGGAGGGG | ACCCAGAAAT | 7360 |
| TGTAATGCAC | AGTTTTAATT | GTGGAGGGGA | ATTTTTCTAC | 7400 |
| TGTAATACAT | CACCACTGTT | TAATAGTACT | TGGAATGGTA | 7440 |
| ATAATACTTG | GAATAATACT | ACAGGGTCAA | ATAACAATAT | 7480 |
| CACACTTCAA | TGCAAAATAA | AACAAATTAT | AAACATGTGG | 7520 |
| CAGGAAGTAG | GAAAAGCAAT | GTATGCCCCT | CCCATTGAAG | 7560 |

-continued

| | | | | |
|---|---|---|---|---|
| GACAAATTAG | ATGTTCATCA | AATATTACAG | GGCTACTATT | 7600 |
| AACAAGAGAT | GGTGGTAAGG | ACACGGACAC | GAACGACACC | 7640 |
| GAGATCTTCA | GACCTGGAGG | AGGAGATATG | AGGGACAATT | 7680 |
| GGAGAAGTGA | ATTATATAAA | TATAAGTAG | TAACAATTGA | 7720 |
| ACCATTAGGA | GTAGCACCCA | CCAAGGCAAA | GAGAAGAGTG | 7760 |
| GTGCAGAGAG | AAAAAAGAGC | AGCGATAGGA | GCTCTGTTCC | 7800 |
| TTGGGTTCTT | AGGAGCAGCA | GGAAGCACTA | TGGGCGCAGC | 7840 |
| GTCAGTGACG | CTGACGGTAC | AGGCCAGACT | ATTATTGTCT | 7880 |
| GGTATAGTGC | AACAGCAGAA | CAATTTGCTG | AGGGCCATTG | 7920 |
| AGGCGCAACA | GCATATGTTG | CAACTCACAG | TCTGGGGCAT | 7960 |
| CAAGCAGCTC | CAGGCAAGAG | TCCTGGCTGT | GGAAAGATAC | 8000 |
| CTAAAGGATC | AACAGCTCCT | GGGGTTTTGG | GGTTGCTCTG | 8040 |
| GAAAACTCAT | TTGCACCACT | ACTGTGCCTT | GGAATGCTAG | 8080 |
| TTGGAGTAAT | AAATCTCTGG | ATGATATTTG | GAATAACATG | 8120 |
| ACCTGGATGC | AGTGGGAAAG | AGAAATTGAC | AATTACACAA | 8160 |
| GCTTAATATA | CTCATTACTA | GAAAAATCGC | AAACCCAACA | 8200 |
| AGAAAAGAAT | GAACAAGAAT | TATTGGAATT | GGATAAATG | 8240 |
| GCAAGTTTGT | GGAATTGGTT | TGACATAACA | AATTGGCTGT | 8280 |
| GGTATATAAA | AATATTCATA | ATGATAGTAG | GAGGCTTGGT | 8320 |
| AGGTTTAAGA | ATAGTTTTTG | CTGTACTTTC | TATAGTGAAT | 8360 |
| AGAGTTAGGC | AGGGATACTC | ACCATTGTCG | TTGCAGACCC | 8400 |
| GCCCCCCAGT | TCCGAGGGGA | CCCGACAGGC | CCGAAGGAAT | 8440 |
| CGAAGAAGAA | GGTGGAGAGA | GAGACAGAGA | CACATCCGGT | 8480 |
| CGATTAGTGC | ATGGATTCTT | AGCAATTATC | TGGGTCGACC | 8520 |
| TGCGGAGCCT | GTTCCTCTTC | AGCTACCACC | ACAGAGACTT | 8560 |
| ACTCTTGATT | GCAGCGAGGA | TTGTGGAACT | TCTGGGACGC | 8600 |
| AGGGGGTGGG | AAGTCCTCAA | ATATTGGTGG | AATCTCCTAC | 8640 |
| AGTATTGGAG | TCAGGAACTA | AAGAGTAGTG | CTGTTAGCTT | 8680 |
| GCTTAATGCC | ACAGCTATAG | CAGTAGCTGA | GGGGACAGAT | 8720 |
| AGGGTTATAG | AAGTACTGCA | AAGAGCTGGT | AGAGCTATTC | 8760 |
| TCCACATACC | TACAAGAATA | AGACAGGGCT | TGGAAAGGGC | 8800 |
| TTTGCTATAA | GATGGGTGGC | AAATGGTCAA | AACGTGTGAC | 8840 |
| TGGATGGCCT | ACTGTAAGGG | AAAGAATGAG | ACGAGCTGAA | 8880 |
| CCAGCTGAGC | TAGCAGCAGA | TGGGGTGGGA | GCAGCATCCC | 8920 |
| GAGACCTGGA | AAAACATGGA | GCACTCACAA | GTAGCAATAC | 8960 |
| AGCAGCTACC | AATGCTGATT | GTGCCTGGCT | AGAAGCACAA | 9000 |
| GAGGAGGAGG | AAGTGGGTTT | TCCAGTCAAA | CCTCAGGTAC | 9040 |
| CTTTAAGACC | AATGACTTAC | AAAGCAGCTT | TAGATCTTAG | 9080 |
| CCACTTTTTA | AAAGAAAAGG | GGGGACTGGA | TGGGTTAATT | 9120 |
| TACTCCCAAA | AGAGACAAGA | CATCCTTGAT | CTGTGGGTCT | 9160 |

| | | | | |
|---|---|---|---|---|
| ACCACACACA | AGGCTACTTC | CCTGATTGGC | AGAACTACAC | 9200 |
| ACCAGGGCCA | GGGATCAGAT | ATCCACTGAC | CTTTGGATGG | 9240 |
| TGCTTCAAGC | TAGTACCAGT | TGAGCCAGAG | AAGATAGAAG | 9280 |
| AGGCCAATAA | AGGAGAGAAC | AACTGCTTGT | TACACCCTAT | 9320 |
| GAGCCAGCAT | GGATGGATGA | CCCGGAGAGA | GAAGTGTTAG | 9360 |
| TGTGGAAGTC | TGACAGCCAC | CTAGCATTTC | AGCATTATGC | 9400 |
| CCGAGAGCTG | CATCCGGAGT | ACTACAAGAA | CTGCTGACAT | 9440 |
| CGAGCTATCT | ACAAGGGACT | TTCCGCTGGG | GACTTTCCAG | 9480 |
| GGAGGTGTGG | CCTGGGCGGG | ACCGGGGAGT | GGCGAGCCCT | 9520 |
| CAGATCGTGC | ATATAAGCAG | CTGCTTTCTG | CCTGTACTGG | 9560 |
| GTCTCTCTGG | TTAGACCAGA | TCTGAGCCTG | GGAGCTCTCT | 9600 |
| GGCTAACTAG | GGAACCCACT | GCTTAAGCCT | CAATAAAGCT | 9640 |
| TGCCTTGAGT | GCTTCAAGTA | GTGTGTGCCC | GTCTGTTATG | 9680 |
| TGACTCTGGT | AGCTAGAGAT | CCCTCAGATC | CTTTTAGGCA | 9720 |
| GTGTGGAAAA | TCTCTAGCA | | | 9739 |

( 2 ) INFORMATION FOR SEQ ID NO:2:

( i ) SEQUENCE CHARACTERISTICS:
        ( A ) LENGTH: 856 amino acids
        ( B ) TYPE: amino acid
        ( D ) TOPOLOGY: linear ( i i ) MOLECULE TYPE: protein ( i x ) SEQUENCE DESCRIPTION: SEQ ID NO:2:

```
Met  Arg  Val  Lys  Gly  Ile  Arg  Arg  Asn  Tyr  Gln  His
 1              5                    10

Trp  Trp  Gly  Trp  Gly  Thr  Met  Leu  Leu  Gly  Leu  Leu
15                   20

Met  Ile  Cys  Ser  Ala  Thr  Glu  Lys  Leu  Trp  Val  Thr
25                   30                             35

Val  Tyr  Tyr  Gly  Val  Pro  Val  Trp  Lys  Glu  Ala  Thr
40                   45

Thr  Thr  Leu  Phe  Cys  Ala  Ser  Asp  Ala  Lys  Ala  Tyr
50                   55                             60

Asp  Thr  Glu  Val  His  Asn  Val  Trp  Ala  Thr  Gln  Ala
65                   70

Cys  Val  Pro  Thr  Asp  Pro  Asn  Pro  Gln  Glu  Val  Glu
75                   80

Leu  Val  Asn  Val  Thr  Glu  Asn  Phe  Asn  Met  Trp  Lys
85                   90                             95

Asn  Asn  Met  Val  Glu  Gln  Met  His  Glu  Asp  Ile  Ile
100                  105

Ser  Leu  Trp  Asp  Gln  Ser  Leu  Lys  Pro  Cys  Val  Lys
110                  115                            120

Leu  Thr  Pro  Leu  Cys  Val  Thr  Leu  Asn  Cys  Thr  Asp
125                  130

Leu  Arg  Asn  Thr  Thr  Asn  Thr  Asn  Asn  Ser  Thr  Ala
135                  140

Asn  Asn  Asn  Ser  Asn  Ser  Glu  Gly  Thr  Ile  Lys  Gly
145                  150                            155
```

```
Gly  Glu  Met  Lys  Asn  Cys  Ser  Phe  Asn  Ile  Thr  Thr
160                 165

Ser  Ile  Arg  Asp  Lys  Met  Gln  Lys  Glu  Tyr  Ala  Leu
170                 175                           180

Leu  Tyr  Lys  Leu  Asp  Ile  Val  Ser  Ile  Asp  Asn  Asp
185                 190

Ser  Thr  Ser  Tyr  Arg  Leu  Ile  Ser  Cys  Asn  Thr  Ser
195                 200

Val  Ile  Thr  Gln  Ala  Cys  Pro  Lys  Ile  Ser  Phe  Glu
205                 210                           215

Pro  Ile  Pro  Ile  His  Tyr  Cys  Ala  Pro  Ala  Gly  Phe
220                 225

Ala  Ile  Leu  Lys  Cys  Asn  Asp  Lys  Lys  Phe  Ser  Gly
230                 235                           240

Lys  Gly  Ser  Cys  Lys  Asn  Val  Ser  Thr  Val  Gln  Cys
245                 250

Thr  His  Gly  Ile  Arg  Pro  Val  Val  Ser  Thr  Gln  Leu
255                 260

Leu  Leu  Asn  Gly  Ser  Leu  Ala  Glu  Glu  Glu  Val  Val
265                 270                           275

Ile  Arg  Ser  Glu  Asn  Phe  Thr  Asp  Asn  Ala  Lys  Thr
280                 285

Ile  Ile  Val  His  Leu  Asn  Glu  Ser  Val  Gln  Ile  Asn
290                 295                           300

Cys  Thr  Arg  Pro  Asn  Tyr  Asn  Lys  Arg  Lys  Arg  Ile
305                 310

His  Ile  Gly  Pro  Gly  Arg  Ala  Phe  Tyr  Thr  Thr  Lys
315                 320

Asn  Ile  Ile  Gly  Thr  Ile  Arg  Gln  Ala  His  Cys  Asn
325                 330                           335

Ile  Ser  Arg  Ala  Lys  Trp  Asn  Asp  Thr  Leu  Arg  Gln
340                 345

Ile  Val  Ser  Lys  Leu  Lys  Glu  Gln  Phe  Lys  Asn  Lys
350                 355                           360

Thr  Ile  Val  Phe  Asn  Gln  Ser  Ser  Gly  Gly  Asp  Pro
365                 370

Glu  Ile  Val  Met  His  Ser  Phe  Asn  Cys  Gly  Gly  Glu
375                 380

Phe  Phe  Tyr  Cys  Asn  Thr  Ser  Pro  Leu  Phe  Asn  Ser
385                 390                           395

Thr  Trp  Asn  Gly  Asn  Asn  Thr  Trp  Asn  Asn  Thr  Thr
400                 405

Gly  Ser  Asn  Asn  Asn  Ile  Thr  Leu  Gln  Cys  Lys  Ile
410                 415                           420

Lys  Gln  Ile  Ile  Asn  Met  Trp  Gln  Glu  Val  Gly  Lys
425                 430

Ala  Met  Tyr  Ala  Pro  Pro  Ile  Glu  Gly  Gln  Ile  Arg
435                 440

Cys  Ser  Ser  Asn  Ile  Thr  Gly  Leu  Leu  Leu  Thr  Arg
445                 450                           455

Asp  Gly  Gly  Lys  Asp  Thr  Asp  Thr  Asn  Asp  Thr  Glu
460                 465

Ile  Phe  Arg  Pro  Gly  Gly  Gly  Asp  Met  Arg  Asp  Asn
```

|       |       |       |       | 470   |       |       |       | 475   |       |       |       | 480   |       |
|-------|-------|-------|-------|-------|-------|-------|-------|-------|-------|-------|-------|-------|-------|
| Trp   | Arg   | Ser   | Glu   | Leu   | Tyr   | Lys   | Tyr   | Lys   | Val   | Val   | Thr   |       |       |
| 485   |       |       |       |       | 490   |       |       |       |       |       |       |       |       |
| Ile   | Glu   | Pro   | Leu   | Gly   | Val   | Ala   | Pro   | Thr   | Lys   | Ala   | Lys   |       |       |
| 495   |       |       |       |       | 500   |       |       |       |       |       |       |       |       |
| Arg   | Arg   | Val   | Val   | Gln   | Arg   | Glu   | Lys   | Arg   | Ala   | Ala   | Ile   |       |       |
| 505   |       |       |       |       | 510   |       |       |       |       |       | 515   |       |       |
| Gly   | Ala   | Leu   | Phe   | Leu   | Gly   | Phe   | Leu   | Gly   | Ala   | Ala   | Gly   |       |       |
| 520   |       |       |       |       | 525   |       |       |       |       |       |       |       |       |
| Ser   | Thr   | Met   | Gly   | Ala   | Ala   | Ser   | Val   | Thr   | Leu   | Thr   | Val   |       |       |
| 530   |       |       |       |       | 535   |       |       |       |       |       | 540   |       |       |
| Gln   | Ala   | Arg   | Leu   | Leu   | Leu   | Ser   | Gly   | Ile   | Val   | Gln   | Gln   |       |       |
| 545   |       |       |       |       | 550   |       |       |       |       |       |       |       |       |
| Gln   | Asn   | Asn   | Leu   | Leu   | Arg   | Ala   | Ile   | Glu   | Ala   | Gln   | Gln   |       |       |
| 555   |       |       |       |       | 560   |       |       |       |       |       |       |       |       |
| His   | Met   | Leu   | Gln   | Leu   | Thr   | Val   | Trp   | Gly   | Ile   | Lys   | Gln   |       |       |
| 565   |       |       |       |       | 570   |       |       |       |       | 575   |       |       |       |
| Leu   | Gln   | Ala   | Arg   | Val   | Leu   | Ala   | Val   | Glu   | Arg   | Tyr   | Leu   |       |       |
| 580   |       |       |       |       | 585   |       |       |       |       |       |       |       |       |
| Lys   | Asp   | Gln   | Gln   | Leu   | Leu   | Gly   | Phe   | Trp   | Gly   | Cys   | Ser   |       |       |
| 590   |       |       |       |       | 595   |       |       |       |       | 600   |       |       |       |
| Gly   | Lys   | Leu   | Ile   | Cys   | Thr   | Thr   | Thr   | Val   | Pro   | Trp   | Asn   |       |       |
| Ala   | Ser   | Trp   | Ser   | Asn   | Lys   | Ser   | Leu   | Asp   | Asp   | Ile   | Trp   |       |       |
| 615   |       |       |       |       | 620   |       |       |       |       |       |       |       |       |
| Asn   | Asn   | Met   | Thr   | Trp   | Met   | Gln   | Trp   | Glu   | Arg   | Glu   | Ile   |       |       |
| 625   |       |       |       |       | 630   |       |       |       |       | 635   |       |       |       |
| Asp   | Asn   | Tyr   | Thr   | Ser   | Leu   | Ile   | Tyr   | Ser   | Leu   | Leu   | Glu   |       |       |
| 640   |       |       |       |       | 645   |       |       |       |       |       |       |       |       |
| Lys   | Ser   | Gln   | Thr   | Gln   | Gln   | Glu   | Lys   | Asn   | Glu   | Gln   | Glu   |       |       |
| 650   |       |       |       |       | 655   |       |       |       |       | 660   |       |       |       |
| Leu   | Leu   | Glu   | Leu   | Asp   | Lys   | Trp   | Ala   | Ser   | Leu   | Trp   | Asn   |       |       |
| 665   |       |       |       |       | 670   |       |       |       |       |       |       |       |       |
| Trp   | Phe   | Asp   | Ile   | Thr   | Asn   | Trp   | Leu   | Trp   | Tyr   | Ile   | Lys   |       |       |
| 675   |       |       |       |       | 680   |       |       |       |       |       |       |       |       |
| Ile   | Phe   | Ile   | Met   | Ile   | Val   | Gly   | Gly   | Leu   | Val   | Gly   | Leu   |       |       |
| 685   |       |       |       |       | 690   |       |       |       |       | 695   |       |       |       |
| Arg   | Ile   | Val   | Phe   | Ala   | Val   | Leu   | Ser   | Ile   | Val   | Asn   | Arg   |       |       |
| 700   |       |       |       |       | 705   |       |       |       |       |       |       |       |       |
| Val   | Arg   | Gln   | Gly   | Tyr   | Ser   | Pro   | Leu   | Ser   | Leu   | Gln   | Thr   |       |       |
| 710   |       |       |       |       | 715   |       |       |       |       | 720   |       |       |       |
| Arg   | Pro   | Pro   | Val   | Pro   | Arg   | Gly   | Pro   | Asp   | Arg   | Pro   | Glu   |       |       |
| 725   |       |       |       |       | 730   |       |       |       |       |       |       |       |       |
| Gly   | Ile   | Glu   | Glu   | Glu   | Gly   | Gly   | Glu   | Arg   | Asp   | Arg   | Asp   |       |       |
| 735   |       |       |       |       | 740   |       |       |       |       |       |       |       |       |
| Thr   | Ser   | Gly   | Arg   | Leu   | Val   | His   | Gly   | Phe   | Leu   | Ala   | Ile   |       |       |
| 745   |       |       |       |       | 750   |       |       |       |       | 755   |       |       |       |
| Ile   | Trp   | Val   | Asp   | Leu   | Arg   | Ser   | Leu   | Phe   | Leu   | Phe   | Ser   |       |       |
| 760   |       |       |       |       | 765   |       |       |       |       |       |       |       |       |
| Tyr   | His   | His   | Arg   | Asp   | Leu   | Leu   | Leu   | Ile   | Ala   | Ala   | Arg   |       |       |
| 770   |       |       |       |       | 775   |       |       |       |       | 780   |       |       |       |
| Ile   | Val   | Glu   | Leu   | Leu   | Gly   | Arg   | Arg   | Gly   | Trp   | Glu   | Val   |       |       |
| 785   |       |       |       |       | 790   |       |       |       |       |       |       |       |       |
| Leu   | Lys   | Tyr   | Trp   | Trp   | Asn   | Leu   | Leu   | Gln   | Tyr   | Trp   | Ser   |       |       |

```
795                     800

Gln  Glu  Leu  Lys  Ser  Ser  Ala  Val  Ser  Leu  Leu  Asn
805                     810                    815

Ala  Thr  Ala  Ile  Ala  Val  Ala  Glu  Gly  Thr  Asp  Arg
820                     825

Val  Ile  Glu  Val  Leu  Gln  Arg  Ala  Gly  Arg  Ala  Ile
830                     835                    840

Leu  His  Ile  Pro  Thr  Arg  Ile  Arg  Gln  Gly  Leu  Glu
845                     850

Arg  Ala  Leu  Leu
855
```

( 2 ) INFORMATION FOR SEQ ID NO:3:

( i ) SEQUENCE CHARACTERISTICS:
        ( A ) LENGTH: 9746 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 6243..8816

( x i ) SEQUENCE DESCRIPTION: SEQ ID NO:3:

```
TGGATGGGTT  AATTTACTCC  CAAAGAGACA  AGACATCCTT              40
GATCTGTGGG  TCTACCACAC  ACAAGGCTAC  TTCCCTGATT              80
GGCAGAACTA  CACACCAGGG  CCAGGGATCA  GATATCCACT             120
GACCTTTGGA  TGGTGCTTCA  AGCTAGTACC  AGTTGAGCCA             160
GAGAAGATAG  AAGAGGCCAA  TAAAGGAGAG  AACAACTGCT             200
TGTTACACCC  TATGAGCCAG  CATGGGATGG  ATGACCCGGA             240
GAGAGAAGTG  TTAGTGTGGA  AGTCTGACAG  CCACCTAGCA             280
TTTCAGCATT  ATGCCCGAGA  GCTGCATCCG  GAGTACTACA             320
AGAACTGCTG  ACATCGAGCT  ATCTACAAGG  GACTTTCCGC             360
TGGGGACTTT  CCAGGGAGGT  GTGGCCTGGG  CGGGACCGGG             400
GAGTGGCGAG  CCCTCAGATG  CTGCATATAA  GCAGCTGCTT             440
TCTGCCTGTA  CTGGGTCTCT  CTGGTTAGAC  CAGATCTGAG             480
CCTGGGAGCT  CTCTGGCTAA  CTAGGGAACC  CACTGCTTAA             520
GCCTCAATAA  AGCTTGCCTT  GAGTGCTTCA  AGTAGTGTGT             560
GCCCGTCTGT  TATGTGACTC  TGGTAGCTAG  AGATCCCTCA             600
GATCCTTTTA  GGCAGTGTGG  AAAATCTCTA  GCAGTGGCGC             640
CCGAACAGGG  ACTTGAAAGC  GAAAGAGAAA  CCAGAGGAGC             680
TCTCTCGACG  CAGGACTCGG  CTTGCTGAAG  CGCGCACGGC             720
AAGAGGCGAG  GGGCGGCGAC  TGGTGAGTAC  GCCAAAATTC             760
TTGACTAGCG  GAGGCTAGAA  GGAGAGAGAT  GGGTGCGAGA             800
GCGTCGGTAT  TAAGCGGGGG  AGAATTAGAT  CGATGGGAAA             840
AAATTCGGTT  AAGGCCAGGG  GGAAAGAAAA  AATATAAATT             880
AAAACATGTA  GTATGGGCAA  GCAGGGAGCT  AGAACGATTC             920
GCAGTCAATC  CTGGCCTGTT  AGAAACATCA  GAAGGCTGTA             960
```

-continued

| | | | | |
|---|---|---|---|---|
| GACAAATACT | GGGACAGCTA | CAACCATCCC | TTCAGACAGG | 1000 |
| ATCAGAAGAA | CTTAAATCAT | TATATAATAC | AGTAGCAACC | 1040 |
| CTCTATTGTG | TGCATCAAAA | GATAGAGATA | AAAGACACCA | 1080 |
| AGGAAGCTTT | AGAGAAAATA | GAGGAAGAGC | AAAACAAAAG | 1120 |
| TAAGAAAAAA | GCACAGCAAG | CAGTAGCTGA | CACAGGAAAC | 1160 |
| AGAGGAAACA | GCAGCCAAGT | CAGCCAAAAT | TACCCCATAG | 1200 |
| TGCAGAACAT | CCAGGGGCAA | ATGGTACATC | AGGCCATATC | 1240 |
| ACCTAGAACT | TTAAATGCAT | GGGTAAAAGT | AGTAGAAGAG | 1280 |
| AAGGCTTTCA | GCCCAGAAGT | AATACCCATG | TTTTCAGCAT | 1320 |
| TATCAGAAGG | AGCCACCCCA | CAAGATTTAA | ACACCATGCT | 1360 |
| AAACACAGTG | GGGGGACATC | AAGCAGCCAT | GCAAATGTTA | 1400 |
| AAAGAGACCA | TCAATGAGGA | AGCTGCAGAA | TGGGATAGAT | 1440 |
| TGCATCCAGT | GCATGCAGGG | CCTATTGCAC | CAGGCCAGAT | 1480 |
| GAGAGAACCA | AGGGGAAGTG | ACATAGCAGG | AACTACTAGT | 1520 |
| ACCCTTCAGG | AACAAATAGG | ATGGATGACA | AATAATCCAC | 1560 |
| CTATCCCAGT | AGGAGAAATC | TATAAAAGAT | GGATAATCCT | 1600 |
| GGGATTAAAT | AAAATAGTAA | GGATGTATAG | CCCTTCCAGC | 1640 |
| ATTCTGGACA | TAAGACAAGG | ACCAAAGGAA | CCCTTTAGAG | 1680 |
| ACTATGTAGA | CCGGTTCTAT | AAAACTCTAA | GAGCCGAGCA | 1720 |
| AGCTTCACAG | GAGGTAAAAA | ATTGGATGAC | AGAAACCTTG | 1760 |
| TTGGTCCAAA | ATGCGAACCC | AGATTGTAAG | ACTATTTTAA | 1800 |
| AAGCATTGGG | ACCAGCAGCT | ACACTAGAAG | AAATGATGAC | 1840 |
| AGCATGTCAG | GGAGTGGGAG | GACCTGGTCA | TAAAGCAAGA | 1880 |
| GTTTTGGCGG | AAGCGATGAG | CCAAGTAACA | AATTCAGCTA | 1920 |
| CCATAATGAT | GCAGAGAGGC | AATTTTAGGA | ATCAAAGAAA | 1960 |
| GATTATCAAG | TGCTTCAATT | GTGGCAAAGA | AGGGCACATA | 2000 |
| GCCAAAAATT | GCAGGGCCCC | TAGGAAAAGG | GGCTGTTGGA | 2040 |
| AATGTGGAAA | GGAAGGACAC | CAAATGAAAG | ATTGTACTGA | 2080 |
| GAGACAGGCT | AATTTTTTAG | GGAAGATCTG | GCCTTCCTGC | 2120 |
| AAGGGAAGGC | AGGGAATTTT | CCTCAGAGCA | GAACAGAGCC | 2160 |
| AACAGCCCCA | CCAGAAGAGA | GCTTCAGGTT | TGGGGAAGAG | 2200 |
| ACAACAACTC | CCTATCAGAA | GCAGGAGAAG | AAGCAGGAGA | 2240 |
| CGATAGACAA | GGACCTGTAT | CCTTTAGCTT | CCCTCAAATC | 2280 |
| ACTCTTTGGC | AACGACCCAT | TGTCACAATA | AAGATAGGGG | 2320 |
| GGCAACTAAA | GGAAGCTCTA | TTAGATACAG | GAGCAGATGA | 2360 |
| TACAGTATTA | GAAGAAATGA | ATTTGCCAGG | AAGATGGAAA | 2400 |
| CCAAAAATGA | TAGGGGAAT | TGGAGGTTTT | ATCAAAGTAA | 2440 |
| GACAGTATGA | TCAGATAACC | ATAGAAATCT | GTGGACATAA | 2480 |
| AGCTATAGGT | ACAGTATTAG | TAGGACCTAC | ACCTGTCAAC | 2520 |
| ATAATTGGAA | GAAATCTGTT | GACTCAGCTT | GGGTGCACTT | 2560 |

| | | | | |
|---|---|---|---|---|
| TAAATTTTCC | CATTAGTCCT | ATTGAAACTG | TACCAGTAAA | 2600 |
| ATTAAAGCCA | GGAATGGATG | GCCCAAAAGT | TAAACAATGG | 2640 |
| CCATTGACAG | AAGAAAAAAT | AAAAGCATTA | ATAGAAATTT | 2680 |
| GTACAGAAAT | GGAAAAGGAA | GGGAAAATTT | CAAAAATTGG | 2720 |
| GCCTGAAAAT | CCATACAATA | CTCCAGTATT | TGCCATAAAG | 2760 |
| AAAAAGACA | GTACTAAATG | GAGAAAATTA | GTAGATTTCA | 2800 |
| GAGAACTTAA | TAAGAAAACT | CAAGACTTCT | GGAAGTTCA | 2840 |
| ATTAGGAATA | CCACATCCTG | CAGGGTTAAA | AAAGAAAAAA | 2880 |
| TCAGTAACAG | TACTGGATGT | GGGTGATGCA | TATTTTTCAG | 2920 |
| TTCCCTTAGA | TAAAGACTTC | AGGAAGTATA | CTGCATTTAC | 2960 |
| CATACCTAGT | ATAAACAATG | AAACACCAGG | GATTAGATAT | 3000 |
| CAGTACAATG | TGCTTCCACA | GGGATGGAAA | GGATCACCAG | 3040 |
| CAATATTCCA | AAGTAGCATG | ACAAAAATCT | TAGAGCCTTT | 3080 |
| TAGAAAACAA | AATCCAGACA | TAGTTATCTA | TCAATACATG | 3120 |
| GATGATTTGT | ATGTAGGATC | TGACTTAGAA | ATAGGGCAGC | 3160 |
| ATAGAGCAAA | AATAGAGGAA | CTGAGACGAC | ATCTGTTGAG | 3200 |
| GTGGGGATTT | ACCACACCAG | ACAAAAAACA | TCAGAAAGAA | 3240 |
| CCTCCATTCC | TTTGGATGGG | TTATGAACTC | CATCCTGATA | 3280 |
| AATGGACAGT | ACAGCCTATA | GTGCTGCCAG | AAAAAGACAG | 3320 |
| CTGGACTGTC | AATGACATAC | AGAAGTTAGT | GGGAAAATTG | 3360 |
| AATTGGGCAA | GTCAAATTTA | CGCAGGGATT | AAAGTAAAGC | 3400 |
| AATTATGTAA | ACTCCTTAGA | GGAACCAAAG | CACTAACAGA | 3440 |
| AGTAATACCA | CTAACAGAAG | AAGCAGAGCT | AGAACTGGCA | 3480 |
| GAAAACAGGG | AAATTCTAAA | AGAACCAGTA | CATGGAGTGT | 3520 |
| ATTATGACCC | ATCAAAAGAC | TTAATAGCAG | AAGTACAGAA | 3560 |
| GCAGGGGCAA | GGCCAATGGA | CATATCAAAT | TTATCAAGAG | 3600 |
| CCATTTAAAA | ATCTGAAAAC | AGGCAAATAT | GCAAGAATGA | 3640 |
| GGGGTGCCCA | CACTAATGAT | GTAAAACAAT | TAACAGAGGC | 3680 |
| AGTGCAAAAA | ATAGCCACAG | AAAGCATAGT | AATATGGGGA | 3720 |
| AAGACTCCTA | AATTTAGACT | ACCCATACAA | AAAGAAACAT | 3760 |
| GGGAAACATG | GTGGACAGAG | TATTGGCAAG | CCACCTGGAT | 3800 |
| TCCTGAGTGG | GAGTTTGTCA | ATACCCCTCC | CTTAGTGAAA | 3840 |
| TTATGGTACC | AGTTAGAGAA | AGAACCCATA | GTAGGAGCAG | 3880 |
| AAACTTTCTA | TGTAGATGGG | GCAGCTAACA | GGGAGACTAA | 3920 |
| AAAAGGAAAA | GCAGGATATG | TTACTAACAG | AGGAAGACAA | 3960 |
| AAGGTTGTCT | CCCTAACTGA | CACAACAAAT | CAGAAGACTG | 4000 |
| AGTTACAAGC | AATTCATCTA | GCTTTGCAAG | ATTCAGGGTT | 4040 |
| AGAAGTAAAC | ATAGTAACAG | ACTCACAATA | TGCATTAGGA | 4080 |
| ATCATTCAAG | CACAACCAGA | TAAAAGTGAA | TCAGAGTTAG | 4120 |
| TCAGTCAAAT | AATAGAGCAG | TTAATAAAAA | AGGAAAAGGT | 4160 |

| | | | | |
|---|---|---|---|---|
| CTATCTGGCA | TGGGTACCAG | CACACAAAGG | AATTGGAGGA | 4200 |
| AATGAACAAG | TAGATAAATT | AGTCAGTGCT | GGAATCAGGA | 4240 |
| AAGTACTATT | TTTAGATGGA | ATAGATAAGG | CCCAAGAAGA | 4280 |
| CCATGAGAAA | TATCACAGTA | ATTGGAGAGC | AATGGCTAGT | 4320 |
| GACTTTAACC | TACCACCTAT | AGTAGCAAAA | GAAATAGTAG | 4360 |
| CCAGCTGTGA | TAAATGTCAG | CTAAAAGGAG | AAGCCATGCA | 4400 |
| TGGACAAGTA | GACTGTAGTC | CAGGAATATG | GCAACTAGAT | 4440 |
| TGTACACATT | TAGAAGGAAA | AGTTATCCTG | GTAGCAGTTC | 4480 |
| ATGTAGCCAG | TGGATACATA | GAAGCAGAAG | TTATTCCAGC | 4520 |
| AGAGACAGGG | CAGGAGACAG | CATACTTTCT | CTTAAAATTA | 4560 |
| GCAGGAAGAT | GGCCAGTAAA | AACAATACAT | ACAGACAATG | 4600 |
| GCCCCAATTT | CACCAGTACT | ACGGTTAAGG | CCGCCTGTTG | 4640 |
| GTGGGCGGGG | ATCAAGCAGG | AATTTGGCAT | TCCCTACAAT | 4680 |
| CCCCAAAGTC | AAGGAGTAAT | AGAATCTATG | AATAAAGAAT | 4720 |
| TAAAGAAAAT | TATAGGACAG | GTAAGAGATC | AGGCTGAACA | 4760 |
| TCTTAAGACA | GCAGTACAAA | TGGCAGTATT | CATCCACAAT | 4800 |
| TTTAAAAGAA | AAGGGGGGAT | TGGGGGGTAC | AGTGCAGGGG | 4840 |
| AAAGAATAGT | AGACATAATA | GCAACAGACA | TACAAACTAA | 4880 |
| AGAACTACAA | AAACAAATTA | CAAAAATTCA | AAATTTTCGG | 4920 |
| GTTTATTACA | GGGACAGCAG | AGATCCACTT | TGGAAAGGAC | 4960 |
| CAGCAAAGCT | TCTCTGGAAA | GGTGAAGGGG | CAGTAGTAAT | 5000 |
| ACAAGATAAT | AGTGACATAA | AAGTAGTGCC | AAGAAGAAAA | 5040 |
| GCAAAGATCA | TTAGGGATTA | TGGAAAACAG | ATGGCAGGTG | 5080 |
| ATGATTGTGT | GGCAAGTAGA | CAGGATGAGG | ATTAGAACAT | 5120 |
| GGAAAAGTTT | AGTAAAACAC | CATATGTATA | TTTCAAAGAA | 5160 |
| AGCTAAAGGA | TGGTTTTATA | GACATCACTA | TGAAAGCACT | 5200 |
| CATCCAAGAA | TAAGTTCAGA | AGTACACATC | CCACTAGGGG | 5240 |
| ATGCTAGATT | GGTAATAACA | ACATATTGGG | GTCTGCATAC | 5280 |
| AGGAGAAAGA | GACTGGCATT | TAGGTCAGGG | AGTCTCCATA | 5320 |
| GAATGGAGGA | AAAAGAGATA | TAGCACACAA | GTAGACCCTG | 5360 |
| ACCTAGCAGA | CCACCTAATT | CATCTGCATT | ACTTTGATTG | 5400 |
| TTTTTCAGAC | TCTGCCATAA | GAAAGGCCAT | ATTAGGACAT | 5440 |
| AGAGTTAGTC | CTATTTGTGA | ATTTCAAGCA | GGACATAACA | 5480 |
| AGGTAGGATC | TCTACAGTAC | TTGGCACTAA | CAGCATTAAT | 5520 |
| AACACCAAAA | AAGATAAAGC | CACCTTTGCC | TAGTGTTAAG | 5560 |
| AAACTGACAG | AGGATAGATG | GAACAAGCCC | CAGAAGACCA | 5600 |
| AGGGCCACAG | AGGGAGCCAT | ACAATCAATG | GCATTAGAG | 5640 |
| CTTTTAGAGG | AGCTTAAGAA | TGAAGCTGTT | AGACATTTTC | 5680 |
| CTAGGATATG | GCTCCATGGC | TTAGGGCAAC | ATATCTATGA | 5720 |
| AACTTATGGG | GATACTTGGG | CAGGAGTGGA | AGCCATAATA | 5760 |

```
AGAATTCTAC AACAACTGCT GTTTATTCAT TTCAGAATTG              5800

GGTGTCGACA TAGCAGAATA GGCATTATTC GACAGAGGAG              5840

AGCAAGAAAT GGAGCCAGTA GATCCTAGAC TAGAGCCCTG              5880

GAAGCATCCA GGAAGTCAGC CTAAGACTGC TTGTACCACT              5920

TGCTATTGTA AAAAGTGTTG CTTTCATTGC CAAGTTTGTT              5960

TCACAAAAAA AGCCTTAGGC ATCTCCTATG GCAGGAAGAA              6000

GCGGAGACAG CGACGAAGAG CTCCTGAAGA CAGTCAGACT              6040

CATCAAGTTT CTCTACCAAA GCAGTAAGTA GTACATGTAA              6080

TGCAACCTTT AGTAATAGCA GCAATAGTAG CATTAGTAGT              6120

AGCAGGAATA ATAGCAATAG TTGTGTGATC CATAGTATTC              6160

ATAGAATATA GGAAAATAAG AAGACAAAGA AAAATAGACA              6200

GGGTAATTGA CAGAATAAGC GAAAGAGCAG AAGACAGTGG              6240
```

| | | | | | | | | | | | |
|---|---|---|---|---|---|---|---|---|---|---|---|
| CA ATG | AGA | GTG | AAG | GGG | ATC | AGG | AGG | AAT | TAT | CAG CC | 6278 |
| Met | Arg | Val | Lys | Gly | Ile | Arg | Arg | Asn | Tyr | Gln His | |
| 1 | | | 5 | | | | | 10 | | | |

| | | | | | | | | | | |
|---|---|---|---|---|---|---|---|---|---|---|
| TGG | TGG | GGA | TGG | GGC | ACG | ATG | CTC | CTT | GGG TTA TTA | 6314 |
| Trp | Trp | Gly | Trp | Gly | Thr | Met | Leu | Leu | Gly Leu Leu | |
| 15 | | | | 20 | | | | | | |

| | | | | | | | | | | |
|---|---|---|---|---|---|---|---|---|---|---|
| ATG | ATC | TGT | AGT | GCT | ACA | GAA | AAA | TTG | TGG GTC ACA | 6350 |
| Met | Ile | Cys | Ser | Ala | Thr | Glu | Lys | Leu | Trp Val Thr | |
| 25 | | | | 30 | | | | | 35 | |

| | | | | | | | | | | |
|---|---|---|---|---|---|---|---|---|---|---|
| GTC | TAT | TAT | GGG | GTA | CCT | GTG | TGG | AAA | GAA GCA ACC | 6386 |
| Val | Tyr | Tyr | Gly | Val | Pro | Val | Trp | Lys | Glu Ala Thr | |
| 40 | | | | 45 | | | | | | |

| | | | | | | | | | | |
|---|---|---|---|---|---|---|---|---|---|---|
| ACC | ACT | CTA | TTT | TGT | GCA | TCA | GAT | GCT | AAA GCA TAT | 6422 |
| Thr | Thr | Leu | Phe | Cys | Ala | Ser | Asp | Ala | Lys Ala Tyr | |
| 50 | | | | 55 | | | | | 60 | |

| | | | | | | | | | | |
|---|---|---|---|---|---|---|---|---|---|---|
| GAT | ACA | GAG | GTA | CAT | AAT | GTT | TGG | GCC | ACA CAT GCC | 6458 |
| Asp | Thr | Glu | Val | His | Asn | Val | Trp | Ala | Thr His Ala | |
| 65 | | | | 70 | | | | | | |

| | | | | | | | | | | |
|---|---|---|---|---|---|---|---|---|---|---|
| TGT | GTA | CCC | ACA | GAC | CCC | AAC | CCA | CAA | GAA GTA GAA | 6494 |
| Cys | Val | Pro | Thr | Asp | Pro | Asn | Pro | Gln | Glu Val Glu | |
| 75 | | | | 80 | | | | | | |

| | | | | | | | | | | |
|---|---|---|---|---|---|---|---|---|---|---|
| TTG | GTA | AAT | GTG | ACA | GAA | AAT | TTT | AAC | ATG TGG AAA | 6530 |
| Leu | Val | Asn | Val | Thr | Glu | Asn | Phe | Asn | Met Trp Lys | |
| 85 | | | | 90 | | | | | 95 | |

| | | | | | | | | | | |
|---|---|---|---|---|---|---|---|---|---|---|
| AAT | AAC | ATG | GTA | GAA | CAG | ATG | CAT | GAG | GAT ATA ATC | 6566 |
| Asn | Asn | Met | Val | Glu | Gln | Met | His | Glu | Asp Ile Ile | |
| 100 | | | | 105 | | | | | | |

| | | | | | | | | | | |
|---|---|---|---|---|---|---|---|---|---|---|
| AGT | TTA | TGG | GAT | CAA | AGC | CTA | AAG | CCA | TGT GTA AAA | 6602 |
| Ser | Leu | Trp | Asp | Gln | Ser | Leu | Lys | Pro | Cys Val Lys | |
| 110 | | | | 115 | | | | | 120 | |

| | | | | | | | | | | |
|---|---|---|---|---|---|---|---|---|---|---|
| TTA | ACC | CCA | CTC | TGT | GTT | ACT | TTA | AAT | TGC ACT GAT | 6638 |
| Leu | Thr | Pro | Leu | Cys | Val | Thr | Leu | Asn | Cys Thr Asp | |
| 125 | | | | 130 | | | | | | |

| | | | | | | | | | | |
|---|---|---|---|---|---|---|---|---|---|---|
| TTG | AGG | AAT | ACT | ACT | AAT | ACC | AAT | AAT | AGT ACT GCT | 6674 |
| Leu | Arg | Asn | Thr | Thr | Asn | Thr | Asn | Asn | Ser Thr Ala | |
| 135 | | | | 140 | | | | | | |

| | | | | | | | | | | |
|---|---|---|---|---|---|---|---|---|---|---|
| AAT | AAC | AAT | AGT | AAT | AGC | GAG | GGA | ACA | ATA AAG GGA | 6710 |
| Asn | Asn | Asn | Ser | Asn | Ser | Glu | Gly | Thr | Ile Lys Gly | |
| 145 | | | | 150 | | | | | 155 | |

| | | | | | | | | | | |
|---|---|---|---|---|---|---|---|---|---|---|
| GGA | GAA | ATG | AAA | AAC | TGC | TCT | TTC | AAT | ATC ACC ACA | 6746 |
| Gly | Glu | Met | Lys | Asn | Cys | Ser | Phe | Asn | Ile Thr Thr | |
| 160 | | | | 165 | | | | | | |

| | | | | | | | | | | | |
|---|---|---|---|---|---|---|---|---|---|---|---|
| AGC | ATA | AGA | GAT | AAG | ATG | CAG | AAA | GAA | TAT | GCA | CTT | 6782
| Ser | Ile | Arg | Asp | Lys | Met | Gln | Lys | Glu | Tyr | Ala | Leu |
| 170 | | | | 175 | | | | | | 180 | |
| CTT | TAT | AAA | CTT | GAT | ATA | GTA | TCA | ATA | AAT | AAT | GAT | 6818
| Leu | Tyr | Lys | Leu | Asp | Ile | Val | Ser | Ile | Asn | Asn | Asp |
| 185 | | | | | 190 | | | | | | |
| AGT | ACC | AGC | TAT | AGG | TTG | ATA | AGT | TGT | AAT | ACC | TCA | 6854
| Ser | Thr | Ser | Tyr | Arg | Leu | Ile | Ser | Cys | Asn | Thr | Ser |
| 195 | | | | | 200 | | | | | | |
| GTC | ATT | ACA | CAA | GCT | TGT | CCA | AAG | ATA | TCC | TTT | GAG | 6890
| Val | Ile | Thr | Gln | Ala | Cys | Pro | Lys | Ile | Ser | Phe | Glu |
| 205 | | | | | 210 | | | | 215 | | |
| CCA | ATT | CCC | ATA | CAC | TAT | TGT | GCC | CCG | GCT | GGT | TTT | 6926
| Pro | Ile | Pro | Ile | His | Tyr | Cys | Ala | Pro | Ala | Gly | Phe |
| 220 | | | | | 225 | | | | | | |
| GCG | ATT | CTA | AAG | TGT | AAC | GAT | AAA | AAG | TTC | AGT | GGA | 6962
| Ala | Ile | Leu | Lys | Cys | Asn | Asp | Lys | Lys | Phe | Ser | Gly |
| 230 | | | | | 235 | | | | | 240 | |
| AAA | GGA | TCA | TGT | AAA | AAT | GTC | AGC | ACA | GTA | CAA | TGT | 6998
| Lys | Gly | Ser | Cys | Lys | Asn | Val | Ser | Thr | Val | Gln | Cys |
| 245 | | | | | 250 | | | | | | |
| ACA | CAT | GGA | ATT | AGG | CCA | GTA | GTA | TCA | ACT | CAA | CTG | 7034
| Thr | His | Gly | Ile | Arg | Pro | Val | Val | Ser | Thr | Gln | Leu |
| 255 | | | | | 260 | | | | | | |
| CTG | TTA | AAT | GGC | AGT | CTA | GCA | GAA | GAA | GAG | GTA | GTA | 7070
| Leu | Leu | Asn | Gly | Ser | Leu | Ala | Glu | Glu | Glu | Val | Val |
| 265 | | | | | 270 | | | | | 275 | |
| ATT | AGA | TCT | GAG | AAT | TTC | AAT | GAT | AAT | GCT | AAA | ACC | 7106
| Ile | Arg | Ser | Glu | Asn | Phe | Asn | Asp | Asn | Ala | Lys | Thr |
| 280 | | | | | 285 | | | | | | |
| ATC | ATA | GTA | CAT | CTG | AAT | GAA | TCT | GTA | CAA | ATT | AAT | 7142
| Ile | Ile | Val | His | Leu | Asn | Glu | Ser | Val | Gln | Ile | Asn |
| 290 | | | | | 295 | | | | 300 | | |
| TGT | ACA | AGA | CCC | AAC | TAC | AAT | AAA | AGA | AAA | AGG | ATA | 7178
| Cys | Thr | Arg | Pro | Asn | Tyr | Asn | Lys | Arg | Lys | Arg | Ile |
| 305 | | | | | 310 | | | | | | |
| CAT | ATA | GGA | CCA | GGG | AGA | GCA | TTT | TAT | ACA | ACA | AAA | 7214
| His | Ile | Gly | Pro | Gly | Arg | Ala | Phe | Tyr | Thr | Thr | Lys |
| 315 | | | | | 320 | | | | | | |
| AAT | ATA | ATA | GGA | ACT | ATA | AGA | CAA | GCA | CAT | TGT | AAC | 7250
| Asn | Ile | Ile | Gly | Thr | Ile | Arg | Gln | Ala | His | Cys | Asn |
| 325 | | | | | 330 | | | | | 335 | |
| ATT | AGT | AGA | GCA | AAA | TGG | AAT | GAC | ACT | TTA | AGA | CAG | 7286
| Ile | Ser | Arg | Ala | Lys | Trp | Asn | Asp | Thr | Leu | Arg | Gln |
| 340 | | | | | 345 | | | | | | |
| ATA | GTT | AGC | AAA | TTA | AAA | GAA | CAA | TTT | AAG | AAT | AAA | 7322
| Ile | Val | Ser | Lys | Leu | Lys | Glu | Gln | Phe | Lys | Asn | Lys |
| 350 | | | | | 355 | | | | | 360 | |
| ACA | ATA | GTC | TTT | AAT | CAA | TCC | TCA | GGA | GGG | GAC | CCA | 7358
| Thr | Ile | Val | Phe | Asn | Gln | Ser | Ser | Gly | Gly | Asp | Pro |
| 365 | | | | | 370 | | | | | | |
| GAA | ATT | GTA | ATG | CAC | AGT | TTT | AAT | TGT | GGA | GGG | GAA | 7394
| Glu | Ile | Val | Met | His | Ser | Phe | Asn | Cys | Gly | Gly | Glu |
| 375 | | | | | 380 | | | | | | |
| TTT | TTC | TAC | TGT | AAT | ACA | TCA | CCA | CTG | TTT | AAT | AGT | 7430
| Phe | Phe | Tyr | Cys | Asn | Thr | Ser | Pro | Leu | Phe | Asn | Ser |
| 385 | | | | | 390 | | | | | 395 | |
| ACT | TGG | AAT | GGT | AAT | AAT | ACT | TGG | AAT | AAT | ACT | ACA | 7466
| Thr | Trp | Asn | Gly | Asn | Asn | Thr | Trp | Asn | Asn | Thr | Thr |
| 400 | | | | | 405 | | | | | | |

| | | | | | | | | | | | |
|---|---|---|---|---|---|---|---|---|---|---|---|
| GGG | TCA | AAT | AAC | AAT | ATC | ACA | CTT | CAA | TGC | AAA | ATA | 7502 |
| Gly | Ser | Asn | Asn | Asn | Ile | Thr | Leu | Gln | Cys | Lys | Ile |
| 410 | | | | 415 | | | | | 420 | | |
| AAA | CAA | ATT | ATA | AAC | ATG | TGG | CAG | GAA | GTA | GGA | AAA | 7538 |
| Lys | Gln | Ile | Ile | Asn | Met | Trp | Gln | Glu | Val | Gly | Lys |
| 425 | | | | | 430 | | | | | | |
| GCA | ATA | TAT | GCC | CCT | CCC | ATT | GAA | GGA | CAA | ATT | AGA | 7574 |
| Ala | Ile | Tyr | Ala | Pro | Pro | Ile | Glu | Gly | Gln | Ile | Arg |
| 435 | | | | 440 | | | | | | | |
| TGT | TCA | TCA | AAT | ATT | ACA | GGG | CTA | CTA | TTA | ACA | AGA | 7610 |
| Cys | Ser | Ser | Asn | Ile | Thr | Gly | Leu | Leu | Leu | Thr | Arg |
| 445 | | | | 450 | | | | | 455 | | |
| GAT | GGT | GGT | AAG | GAC | ACG | GAC | ACG | AAC | GAC | ACC | GAG | 7646 |
| Asp | Gly | Gly | Lys | Asp | Thr | Asp | Thr | Asn | Asp | Thr | Glu |
| 460 | | | | 465 | | | | | | | |
| ATC | TTC | AGA | CCT | GGA | GGA | GGA | GAT | ATG | AGG | GAC | AAT | 7682 |
| Ile | Phe | Arg | Pro | Gly | Gly | Gly | Asp | Met | Arg | Asp | Asn |
| 470 | | | | 475 | | | | | 480 | | |
| TGG | AGA | AGT | GAA | TTA | TAT | AAA | TAT | AAA | GTA | GTA | ACA | 7718 |
| Trp | Arg | Ser | Glu | Leu | Tyr | Lys | Tyr | Lys | Val | Val | Thr |
| 485 | | | | 490 | | | | | | | |
| ATT | GAA | CCA | TTA | GGA | GTA | GCA | CCC | ACC | AAG | GCA | AAG | 7754 |
| Ile | Glu | Pro | Leu | Gly | Val | Ala | Pro | Thr | Lys | Ala | Lys |
| 495 | | | | 500 | | | | | | | |
| AGA | AGA | GTG | GTG | CAG | AGA | GAA | AAA | AGA | GCA | GCG | ATA | 7790 |
| Arg | Arg | Val | Val | Gln | Arg | Glu | Lys | Arg | Ala | Ala | Ile |
| 505 | | | | 510 | | | | | 515 | | |
| GGA | GCT | CTG | TTC | CTT | GGG | TTC | TTA | GGA | GCA | GCA | GGA | 7826 |
| Gly | Ala | Leu | Phe | Leu | Gly | Phe | Leu | Gly | Ala | Ala | Gly |
| 520 | | | | 525 | | | | | | | |
| AGC | ACT | ATG | GGC | GCA | GCG | TCA | GTG | ACG | CTG | ACG | GTA | 7862 |
| Ser | Thr | Met | Gly | Ala | Ala | Ser | Val | Thr | Leu | Thr | Val |
| 530 | | | | 535 | | | | | 540 | | |
| CAG | GCC | AGA | CTA | TTA | TTG | TCT | GGT | ATA | GTG | CAA | CAG | 7898 |
| Gln | Ala | Arg | Leu | Leu | Leu | Ser | Gly | Ile | Val | Gln | Gln |
| 545 | | | | 550 | | | | | | | |
| CAG | AAC | AAT | TTG | CTG | AGG | GCC | ATT | GAG | GCG | CAA | CAG | 7934 |
| Gln | Asn | Asn | Leu | Leu | Arg | Ala | Ile | Glu | Ala | Gln | Gln |
| 555 | | | | 560 | | | | | | | |
| CAT | ATG | TTG | CAA | CTC | ACA | GTC | TGG | GGC | ATC | AAG | CAG | 7970 |
| His | Met | Leu | Gln | Leu | Thr | Val | Trp | Gly | Ile | Lys | Gln |
| 565 | | | | 570 | | | | | 575 | | |
| CTC | CAG | GCA | AGA | ATC | CTG | GCT | GTG | GAA | AGA | TAC | CTA | 8006 |
| Leu | Gln | Ala | Arg | Ile | Leu | Ala | Val | Glu | Arg | Tyr | Leu |
| 580 | | | | 585 | | | | | | | |
| AAG | GAT | CAA | CAG | CTC | CTG | GGG | ATT | TGG | GGT | TGC | TCT | 8042 |
| Lys | Asp | Gln | Gln | Leu | Leu | Gly | Ile | Trp | Gly | Cys | Ser |
| 590 | | | | 595 | | | | | 600 | | |
| GGA | AAA | CTC | ATT | TGC | ACC | ACT | ACT | GTG | CCT | TGG | AAT | 8078 |
| Gly | Lys | Leu | Ile | Cys | Thr | Thr | Thr | Val | Pro | Trp | Asn |
| 605 | | | | 610 | | | | | | | |
| GCT | AGT | TGG | AGT | AAT | AAA | TCT | CTG | GAT | GAT | ATT | TGG | 8114 |
| Ala | Ser | Trp | Ser | Asn | Lys | Ser | Leu | Asp | Asp | Ile | Trp |
| 615 | | | | 620 | | | | | | | |
| AAT | AAC | ATG | ACC | TGG | ATG | CAG | TGG | GAA | AGA | GAA | ATT | 8150 |
| Asn | Asn | Met | Thr | Trp | Met | Gln | Trp | Glu | Arg | Glu | Ile |
| 625 | | | | 630 | | | | | 635 | | |
| GAC | AAT | TAC | ACA | AGC | TTA | ATA | TAC | TCA | TTA | CTA | GAA | 8186 |
| Asp | Asn | Tyr | Thr | Ser | Leu | Ile | Tyr | Ser | Leu | Leu | Glu |
| 640 | | | | 645 | | | | | | | |

| | | | | | | | | | | | |
|---|---|---|---|---|---|---|---|---|---|---|---|
| AAA | TCG | CAA | ACC | CAA | CAA | GAA | ATG | AAT | GAA | CAA | GAA |
| Lys | Ser | Gln | Thr | Gln | Gln | Glu | Met | Asn | Glu | Gln | Glu |
| 650 | | | | 655 | | | | | 660 | | |

8222

| | | | | | | | | | | | |
|---|---|---|---|---|---|---|---|---|---|---|---|
| TTA | TTG | GAA | TTG | GAT | AAA | TGG | GCA | AGT | TTG | TGG | AAT |
| Leu | Leu | Glu | Leu | Asp | Lys | Trp | Ala | Ser | Leu | Trp | Asn |
| 665 | | | | | 670 | | | | | | |

8258

| | | | | | | | | | | | |
|---|---|---|---|---|---|---|---|---|---|---|---|
| TGG | TTT | GAC | ATA | ACA | AAT | TGG | CTG | TGG | TAT | ATA | AAA |
| Trp | Phe | Asp | Ile | Thr | Asn | Trp | Leu | Trp | Tyr | Ile | Lys |
| 675 | | | | | 680 | | | | | | |

8294

| | | | | | | | | | | | |
|---|---|---|---|---|---|---|---|---|---|---|---|
| ATA | TTC | ATA | ATG | ATA | GTA | GGA | GGC | TTG | GTA | GGT | TTA |
| Ile | Phe | Ile | Met | Ile | Val | Gly | Gly | Leu | Val | Gly | Leu |
| 685 | | | | | 690 | | | | | 695 | |

8330

| | | | | | | | | | | | |
|---|---|---|---|---|---|---|---|---|---|---|---|
| AGA | ATA | GTT | TTT | GCT | GTA | CTT | TCT | ATA | GTG | AAT | AGA |
| Arg | Ile | Val | Phe | Ala | Val | Leu | Ser | Ile | Val | Asn | Arg |
| 700 | | | | | 705 | | | | | | |

8366

| | | | | | | | | | | | |
|---|---|---|---|---|---|---|---|---|---|---|---|
| GTT | AGG | CAG | GGA | TAC | TCA | CCA | TTG | TCG | TTG | CAG | ACC |
| Val | Arg | Gln | Gly | Tyr | Ser | Pro | Leu | Ser | Leu | Gln | Thr |
| 710 | | | | | 715 | | | | | 720 | |

8402

| | | | | | | | | | | | |
|---|---|---|---|---|---|---|---|---|---|---|---|
| CGC | CCC | CCA | GTT | CCG | AGG | GGA | CCC | GAC | AGG | CCC | GAA |
| Arg | Pro | Pro | Val | Pro | Arg | Gly | Pro | Asp | Arg | Pro | Glu |
| 725 | | | | | 730 | | | | | | |

8438

| | | | | | | | | | | | |
|---|---|---|---|---|---|---|---|---|---|---|---|
| GGA | ATC | GAA | GAA | GAA | GGT | GGA | GAG | AGA | GAC | AGA | GAC |
| Gly | Ile | Glu | Glu | Glu | Gly | Gly | Glu | Arg | Asp | Arg | Asp |
| 735 | | | | | 740 | | | | | | |

8474

| | | | | | | | | | | | |
|---|---|---|---|---|---|---|---|---|---|---|---|
| ACA | TCC | GGT | CGA | TTA | GTG | CAT | GGA | TTC | TTA | GCA | ATT |
| Thr | Ser | Gly | Arg | Leu | Val | His | Gly | Phe | Leu | Ala | Ile |
| 745 | | | | | 750 | | | | | 755 | |

8510

| | | | | | | | | | | | |
|---|---|---|---|---|---|---|---|---|---|---|---|
| ATC | TGG | GTC | GAC | CTG | CGG | AGC | CTG | TTC | CTC | TTC | AGC |
| Ile | Trp | Val | Asp | Leu | Arg | Ser | Leu | Phe | Leu | Phe | Ser |
| 760 | | | | | 765 | | | | | | |

8546

| | | | | | | | | | | | |
|---|---|---|---|---|---|---|---|---|---|---|---|
| TAC | CAC | CAC | TTG | AGA | GAC | TTA | CTC | TTG | ATT | GCA | GCG |
| Tyr | His | His | Leu | Arg | Asp | Leu | Leu | Leu | Ile | Ala | Ala |
| 770 | | | | | 775 | | | | | 780 | |

8582

| | | | | | | | | | | | |
|---|---|---|---|---|---|---|---|---|---|---|---|
| AGG | ATT | GTG | GAA | CTT | CTG | GGA | CGC | AGG | GGG | TGG | GAA |
| Arg | Ile | Val | Glu | Leu | Leu | Gly | Arg | Arg | Gly | Trp | Glu |
| 785 | | | | | 790 | | | | | | |

8618

| | | | | | | | | | | | |
|---|---|---|---|---|---|---|---|---|---|---|---|
| GTC | CTC | AAA | TAT | TGG | TGG | AAT | CTC | CTA | CAG | TAT | TGG |
| Val | Leu | Lys | Tyr | Trp | Trp | Asn | Leu | Leu | Gln | Tyr | Trp |
| 795 | | | | | 800 | | | | | | |

8654

| | | | | | | | | | | | |
|---|---|---|---|---|---|---|---|---|---|---|---|
| AGT | CAG | GAA | CTA | AAG | AGT | AGT | GCT | GTT | AGC | TTG | CTT |
| Ser | Gln | Glu | Leu | Lys | Ser | Ser | Ala | Val | Ser | Leu | Leu |
| 805 | | | | | 810 | | | | | 815 | |

8690

| | | | | | | | | | | | |
|---|---|---|---|---|---|---|---|---|---|---|---|
| AAT | GCC | ACA | GAT | ATA | GCA | GTA | GCT | GAG | GGG | ACA | GAT |
| Asn | Ala | Thr | Asp | Ile | Ala | Val | Ala | Glu | Gly | Thr | Asp |
| 820 | | | | | 825 | | | | | | |

8726

| | | | | | | | | | | | |
|---|---|---|---|---|---|---|---|---|---|---|---|
| AGG | GTT | ATA | GAA | GTA | CTG | CAA | AGA | GCT | GGT | AGA | GCT |
| Arg | Val | Ile | Glu | Val | Leu | Gln | Arg | Ala | Gly | Arg | Ala |
| 830 | | | | | 835 | | | | | 840 | |

8762

| | | | | | | | | | | | |
|---|---|---|---|---|---|---|---|---|---|---|---|
| ATT | CTC | CAC | ATA | CCT | ACA | AGA | ATA | AGA | CAG | GGC | TTG |
| Ile | Leu | His | Ile | Pro | Thr | Arg | Ile | Arg | Gln | Gly | Leu |
| 845 | | | | | 850 | | | | | | |

8798

| | | | |
|---|---|---|---|
| GAA | AGG | GCT | TTG | CTA |
| Glu | Arg | Ala | Leu | Leu |
| 855 | | | | |

8813

| | | | |
|---|---|---|---|
| TAAGATGGGT | GGCAAATGGT | CAAAACGTGT | GACTGGATGG | 8853 |
| CCTACTGTAA | GGGAAAAAAT | GAGACGAGCT | GAACCAGCTG | 8893 |
| AGCCAGCAGC | AGATGGGGTG | GGAGCAGCAT | CCCGAGACCT | 8933 |
| GGAAAAACAT | GGAGCACTCA | CAAGTAGCAA | TACAGCAGCT | 8973 |

| | | | |
|---|---|---|---|
| ACCAATGCTG | ATTGTGCCTG | GCTAGAAGCA | CAAGAGGAGG | 9013 |
| AGGAAGTGGG | TTTTCCAGTC | AGACCTCAGG | TACCTTTAAG | 9053 |
| ACCAATGACT | TACAAAGCAG | CTTTAGATCT | TAGCCACTTT | 9093 |
| TTAAAAGAAA | AGGGGGGACT | GGATGGGTTA | ATTTACTCCC | 9133 |
| AAAAGAGACA | AGACATCCTT | GATCTGTGGG | TCTACCACAC | 9173 |
| ACAAGGCTAC | TTCCCTGATT | GGCAGAACTA | CACACCAGGG | 9213 |
| CCAGGGATCA | GATATCCACT | GACCTTTGGA | TGGTGCTTCA | 9253 |
| AGCTAGTACC | AGTTGAGCCA | GAGAAGATAG | AAGAGGCCAA | 9293 |
| TAAAGGAGAG | AACAACTGCT | TGTTACACCC | TATGAGCCAG | 9333 |
| CATGGGATGG | ATGACCCGGA | GAGAGAAGTG | TTAGTGTGGA | 9373 |
| AGTCTGACAG | CCACCTAGCA | TTTCAGCATT | ATGCCCGAGA | 9413 |
| GCTGCATCCG | GAGTACTACA | AGAACTGCTG | ACATCGAGCT | 9453 |
| ATCTACAAGG | GACTTTCCGC | TGGGGACTTT | CCAGGGAGGT | 9493 |
| GTGGCCTGGG | CGGGACCGGG | GAGTGGCGAG | CCCTCAGATG | 9533 |
| CTGCATATAA | GCAGCTGCTT | TCTGCCTGTA | CTGGGTCTCT | 9573 |
| CTGGTTAGAC | CAGATCTGAG | CCTGGGAGCT | CTCTGGCTAA | 9613 |
| CTAGGGAACC | CACTGCTTAA | GCCTCAATAA | AGCTTGCCTT | 9653 |
| GAGTGCTTCA | AGTAGTGTGT | GCCCGTCTGT | TATGTGACTC | 9693 |
| TGGTAGCTAG | AGATCCCTCA | GATCCTTTTA | GGCAGTGTGG | 9733 |
| AAAATCTCTA | GCA | | | 9746 |

( 2 ) INFORMATION FOR SEQ ID NO:4:

( i ) SEQUENCE CHARACTERISTICS:
        ( A ) LENGTH: 857 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Arg  Val  Lys  Gly  Ile  Arg  Arg  Asn  Tyr  Gln  His
 1              5                        10

Trp  Trp  Gly  Trp  Gly  Thr  Met  Leu  Leu  Gly  Leu  Leu
15                       20

Met  Ile  Cys  Ser  Ala  Thr  Glu  Lys  Leu  Trp  Val  Thr
25                       30                       35

Val  Tyr  Tyr  Gly  Val  Pro  Val  Trp  Lys  Glu  Ala  Thr
40                       45

Thr  Thr  Leu  Phe  Cys  Ala  Ser  Asp  Ala  Lys  Ala  Tyr
50                       55                       60

Asp  Thr  Glu  Val  His  Asn  Val  Trp  Ala  Thr  His  Ala
65                       70

Cys  Val  Pro  Thr  Asp  Pro  Asn  Pro  Gln  Glu  Val  Glu
75                       80

Leu  Val  Asn  Val  Thr  Glu  Asn  Phe  Asn  Met  Trp  Lys
85                       90                       95

Asn  Asn  Met  Val  Glu  Gln  Met  His  Glu  Asp  Ile  Ile
100                      105

Ser  Leu  Trp  Asp  Gln  Ser  Leu  Lys  Pro  Cys  Val  Lys
```

|     |     |     |     |     |     |     |     |     |     |
|-----|-----|-----|-----|-----|-----|-----|-----|-----|-----|
| 110 |     |     |     | 115 |     |     |     | 120 |     |
| Leu 125 | Thr | Pro | Leu | Cys | Val 130 | Thr | Leu | Asn | Cys | Thr | Asp |
| Leu 135 | Arg | Asn | Thr | Thr | Asn 140 | Thr | Asn | Asn | Ser | Thr | Ala |
| Asn 145 | Asn | Asn | Ser | Asn | Ser 150 | Glu | Gly | Thr | Ile | Lys 155 | Gly |
| Gly 160 | Glu | Met | Lys | Asn | Cys 165 | Ser | Phe | Asn | Ile | Thr | Thr |
| Ser 170 | Ile | Arg | Asp | Lys | Met 175 | Gln | Lys | Glu | Tyr | Ala 180 | Leu |
| Leu 185 | Tyr | Lys | Leu | Asp | Ile 190 | Val | Ser | Ile | Asn | Asn | Asp |
| Ser 195 | Thr | Ser | Tyr | Arg | Leu 200 | Ile | Ser | Cys | Asn | Thr | Ser |
| Val 205 | Ile | Thr | Gln | Ala | Cys 210 | Pro | Lys | Ile | Ser | Phe 215 | Glu |
| Pro 220 | Ile | Pro | Ile | His | Tyr 225 | Cys | Ala | Pro | Ala | Gly | Phe |
| Ala 230 | Ile | Leu | Lys | Cys | Asn 235 | Asp | Lys | Lys | Phe | Ser 240 | Gly |
| Lys 245 | Gly | Ser | Cys | Lys | Asn 250 | Val | Ser | Thr | Val | Gln | Cys |
| Thr 255 | His | Gly | Ile | Arg | Pro 260 | Val | Val | Ser | Thr | Gln | Leu |
| Leu 265 | Leu | Asn | Gly | Ser | Leu 270 | Ala | Glu | Glu | Val 275 | Val |
| Ile 280 | Arg | Ser | Glu | Asn | Phe 285 | Asn | Asp | Asn | Ala | Lys | Thr |
| Ile 290 | Ile | Val | His | Leu | Asn 295 | Glu | Ser | Val | Gln | Ile 300 | Asn |
| Cys 305 | Thr | Arg | Pro | Asn | Tyr 310 | Asn | Lys | Arg | Lys | Arg | Ile |
| His 315 | Ile | Gly | Pro | Gly | Arg 320 | Ala | Phe | Tyr | Thr | Thr | Lys |
| Asn 325 | Ile | Ile | Gly | Thr | Ile 330 | Arg | Gln | Ala | His | Cys 335 | Asn |
| Ile 340 | Ser | Arg | Ala | Lys | Trp 345 | Asn | Asp | Thr | Leu | Arg | Gln |
| Ile 350 | Val | Ser | Lys | Leu | Lys 355 | Glu | Gln | Phe | Lys | Asn 360 | Lys |
| Thr 365 | Ile | Val | Phe | Asn | Gln 370 | Ser | Ser | Gly | Gly | Asp | Pro |
| Glu 375 | Ile | Val | Met | His | Ser 380 | Phe | Asn | Cys | Gly | Gly | Glu |
| Phe 385 | Phe | Tyr | Cys | Asn | Thr 390 | Ser | Pro | Leu | Phe | Asn 395 | Ser |
| Thr 400 | Trp | Asn | Gly | Asn | Asn 405 | Thr | Trp | Asn | Asn | Thr | Thr |
| Gly 410 | Ser | Asn | Asn | Asn | Ile 415 | Thr | Leu | Gln | Cys | Lys 420 | Ile |
| Lys 425 | Gln | Ile | Ile | Asn | Met 430 | Trp | Gln | Glu | Val | Gly | Lys |
| Ala | Ile | Tyr | Ala | Pro | Pro | Ile | Glu | Gly | Gln | Ile | Arg |

```
                    4 3 5                                      4 4 0

Cys  Ser  Ser  Asn  Ile  Thr  Gly  Leu  Leu  Leu  Thr  Arg
     4 4 5                4 5 0                          4 5 5

Asp  Gly  Gly  Lys  Asp  Thr  Asp  Thr  Asn  Asp  Thr  Glu
     4 6 0                4 6 5

Ile  Phe  Arg  Pro  Gly  Gly  Gly  Asp  Met  Arg  Asp  Asn
     4 7 0                4 7 5                          4 8 0

Trp  Arg  Ser  Glu  Leu  Tyr  Lys  Tyr  Lys  Val  Val  Thr
     4 8 5                4 9 0

Ile  Glu  Pro  Leu  Gly  Val  Ala  Pro  Thr  Lys  Ala  Lys
     4 9 5                5 0 0

Arg  Arg  Val  Val  Gln  Arg  Glu  Lys  Arg  Ala  Ala  Ile
     5 0 5                5 1 0                          5 1 5

Gly  Ala  Leu  Phe  Leu  Gly  Phe  Leu  Gly  Ala  Ala  Gly
     5 2 0                5 2 5

Ser  Thr  Met  Gly  Ala  Ala  Ser  Val  Thr  Leu  Thr  Val
     5 3 0                5 3 5                          5 4 0

Gln  Ala  Arg  Leu  Leu  Leu  Ser  Gly  Ile  Val  Gln  Gln
     5 4 5                5 5 0

Gln  Asn  Asn  Leu  Leu  Arg  Ala  Ile  Glu  Ala  Gln  Gln
     5 5 5                5 6 0

His  Met  Leu  Gln  Leu  Thr  Val  Trp  Gly  Ile  Lys  Gln
     5 6 5                5 7 0                          5 7 5

Leu  Gln  Ala  Arg  Ile  Leu  Ala  Val  Glu  Arg  Tyr  Leu
     5 8 0                5 8 5

Lys  Asp  Gln  Gln  Leu  Leu  Gly  Ile  Trp  Gly  Cys  Ser
     5 9 0                5 9 5                          6 0 0

Gly  Lys  Leu  Ile  Cys  Thr  Thr  Thr  Val  Pro  Trp  Asn
     6 0 5                6 1 0

Ala  Ser  Trp  Ser  Asn  Lys  Ser  Leu  Asp  Asp  Ile  Trp
     6 1 5                6 2 0

Asn  Asn  Met  Thr  Trp  Met  Gln  Trp  Glu  Arg  Glu  Ile
     6 2 5                6 3 0                          6 3 5

Asp  Asn  Tyr  Thr  Ser  Leu  Ile  Tyr  Ser  Leu  Leu  Glu
     6 4 0                6 4 5

Lys  Ser  Gln  Thr  Gln  Gln  Glu  Met  Asn  Glu  Gln  Glu
     6 5 0                6 5 5                          6 6 0

Leu  Leu  Glu  Leu  Asp  Lys  Trp  Ala  Ser  Leu  Trp  Asn
     6 6 5                6 7 0

Trp  Phe  Asp  Ile  Thr  Asn  Trp  Leu  Trp  Tyr  Ile  Lys
     6 7 5                6 8 0

Ile  Phe  Ile  Met  Ile  Val  Gly  Gly  Leu  Val  Gly  Leu
     6 8 5                6 9 0                          6 9 5

Arg  Ile  Val  Phe  Ala  Val  Leu  Ser  Ile  Val  Asn  Arg
     7 0 0                7 0 5

Val  Arg  Gln  Gly  Tyr  Ser  Pro  Leu  Ser  Leu  Gln  Thr
     7 1 0                7 1 5                          7 2 0

Arg  Pro  Pro  Val  Pro  Arg  Gly  Pro  Asp  Arg  Pro  Glu
     7 2 5                7 3 0

Gly  Ile  Glu  Glu  Glu  Gly  Gly  Glu  Arg  Asp  Arg  Asp
     7 3 5                7 4 0

Thr  Ser  Gly  Arg  Leu  Val  His  Gly  Phe  Leu  Ala  Ile
     7 4 5                7 5 0                          7 5 5
```

| Ile | Trp | Val | Asp | Leu | Arg | Ser | Leu | Phe | Leu | Phe | Ser |
| 760 | | | | | 765 | | | | | | |

| Tyr | His | His | Leu | Arg | Asp | Leu | Leu | Leu | Ile | Ala | Ala |
| 770 | | | | | 775 | | | | 780 | | |

| Arg | Ile | Val | Glu | Leu | Leu | Gly | Arg | Arg | Gly | Trp | Glu |
| 785 | | | | | 790 | | | | | | |

| Val | Leu | Lys | Tyr | Trp | Trp | Asn | Leu | Leu | Gln | Tyr | Trp |
| 795 | | | | | 800 | | | | | | |

| Ser | Gln | Glu | Leu | Lys | Ser | Ser | Ala | Val | Ser | Leu | Leu |
| 805 | | | | | 810 | | | | 815 | | |

| Asn | Ala | Thr | Asp | Ile | Ala | Val | Ala | Glu | Gly | Thr | Asp |
| 820 | | | | | 825 | | | | | | |

| Arg | Val | Ile | Glu | Val | Leu | Gln | Arg | Ala | Gly | Arg | Ala |
| 830 | | | | | 835 | | | | 840 | | |

| Ile | Leu | His | Ile | Pro | Thr | Arg | Ile | Arg | Gln | Gly | Leu |
| 845 | | | | | 850 | | | | | | |

| Glu | Arg | Ala | Leu | Leu |
| 855 | | | | |

( 2 ) INFORMATION FOR SEQ ID NO:5:

( i ) SEQUENCE CHARACTERISTICS:
        ( A ) LENGTH: 3807 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 648..3215

( x i ) SEQUENCE DESCRIPTION: SEQ ID NO:5:

| GATCAAGGGC | CACAGAGGGA | GCCACACAAT | GAATGGACAC | 40 |
| TAGAGCTTTT | AGAGGAGCTT | AAGAGTGAAG | CTGTTAGACA | 80 |
| CTTTCCTAGG | ATATGGCTTC | ATGGCTTAGG | GCAACATATC | 120 |
| TATGAAACTT | ATGGGGATAC | TTGGGCAGGA | GTGGAAGCCA | 160 |
| TAATAAGAAT | TCTGCAACAA | CTGCTGTTTA | TCCATTTCAG | 200 |
| GATTGGGTGC | CAACATAGCA | GAATAGGTAT | TATTCAACAG | 240 |
| AGGAGAGCAA | GAAATGGAGC | CAGTAGATCC | TAAACTAGAG | 280 |
| CCCTGGAAGC | ATCCAGGAAG | TCAGCCTAAG | ACTGCTTGTA | 320 |
| CCACTTGCTA | TTGTAAAAAG | TGTTGCTTTC | ATTGCCAAGT | 360 |
| TTGCTTCATA | ACAAAAGGCT | TAGGCATCTC | CTATGGCAGG | 400 |
| AAGAAGCGGA | GACAGCGACG | AAGAGCTCCT | CAAGACAGTG | 440 |
| AGACTCATCA | AGTTTCTCTA | TCAAAGCAGT | AAGTAGTACA | 480 |
| TGTAATGCAA | GCTTTACAAA | TATCAGCTAT | AGTAGGATTA | 520 |
| GTAGTAGCAG | CAATAATAGC | AATAGTTGTG | TGGACCATAG | 560 |
| TATTCATAGA | ATATAGGAAA | ATATTAAGGC | AAAGAAAAAT | 600 |
| AGACAGGTTA | ATTGATAGAA | TAACAGAAAG | AGCAGAAGAC | 640 |

| AGTGGCA | ATG | AGA | GTG | ACG | GAG | ATC | AGG | AAG | AGT | TAT | CAG | CAC | 683 |
| | Met | Arg | Val | Thr | Glu | Ile | Arg | Lys | Ser | Tyr | Gln | His | |
| | 1 | | | | 5 | | | | | 10 | | | |

| TGG | TGG | AGA | TGG | GGC | ATC | ATG | CTC | CTT | GGG | ATA | TTA | | 719 |

| | | | | | | | | | | | |
|---|---|---|---|---|---|---|---|---|---|---|---|
|Trp|Trp|Arg|Trp|Gly|Ile|Met|Leu|Leu|Gly|Ile|Leu|
|15| | | |20| | | | | | | |

ATG ATC TGT AAT GCT GAA GAA AAA TTG TGG GTC ACA 755
Met Ile Cys Asn Ala Glu Glu Lys Leu Trp Val Thr
25 30 35

GTC TAT TAT GGG GTA CCT GTG TGG AAA GAA GCA ACC 791
Val Tyr Tyr Gly Val Pro Val Trp Lys Glu Ala Thr
40 45

ACC ACT CTA TTT TGT GCA TCA GAT CGT AAA GCA TAT 827
Thr Thr Leu Phe Cys Ala Ser Asp Arg Lys Ala Tyr
50 55 60

GAT ACA GAG GTA CAT AAT GTT TGG GCC ACA CAT GCC 863
Asp Thr Glu Val His Asn Val Trp Ala Thr His Ala
65 70

TGT GTA CCC ACA GAC CCC AAC CCA CAA GAA GTA GAA 899
Cys Val Pro Thr Asp Pro Asn Pro Gln Glu Val Glu
75 80

TTG AAA AAT GTG ACA GAA AAT TTT AAC ATG TGG AAA 935
Leu Lys Asn Val Thr Glu Asn Phe Asn Met Trp Lys
85 90 95

AAT AAC ATG GTA GAA CAA ATG CAT GAG GAT ATA ATC 971
Asn Asn Met Val Glu Gln Met His Glu Asp Ile Ile
100 105

AGT TTA TGG GAT CAA AGC CTA AAG CCA TGT GTA AAA 1007
Ser Leu Trp Asp Gln Ser Leu Lys Pro Cys Val Lys
110 115 120

TTA ACC CCA CTC TGT GTT ACT TTA AAT TGC ACT GAT 1043
Leu Thr Pro Leu Cys Val Thr Leu Asn Cys Thr Asp
125 130

TTG AGG AAT GCT ACT AAT GGG AAT GAC ACT AAT ACC 1079
Leu Arg Asn Ala Thr Asn Gly Asn Asp Thr Asn Thr
135 140

ACT AGT AGT AGC AGG GGA ATG GTG GGG GGA GGA GAA 1115
Thr Ser Ser Ser Arg Gly Met Val Gly Gly Gly Glu
145 150 155

ATG AAA AAT TGC TCT TTC AAT ATC ACC ACA AAC ATA 1151
Met Lys Asn Cys Ser Phe Asn Ile Thr Thr Asn Ile
160 165

AGA GGT AAG GTG CAG AAA GAA TAT GCA CTT TTT TAT 1187
Arg Gly Lys Val Gln Lys Glu Tyr Ala Leu Phe Tyr
170 175 180

AAA CTT GAT ATA GCA CCA ATA GAT AAT AAT AGT AAT 1223
Lys Leu Asp Ile Ala Pro Ile Asp Asn Asn Ser Asn
185 190

AAT AGA TAT AGG TTG ATA AGT TGT AAC ACC TCA GTC 1259
Asn Arg Tyr Arg Leu Ile Ser Cys Asn Thr Ser Val
195 200

ATT ACA CAG GCC TGT CCA AAG GTA TCC TTT GAG CCA 1295
Ile Thr Gln Ala Cys Pro Lys Val Ser Phe Glu Pro
205 210 215

ATT CCC ATA CAT TAT TGT GCC CCG GCT GGT TTT GCG 1331
Ile Pro Ile His Tyr Cys Ala Pro Ala Gly Phe Ala
220 225

ATT CTA AAG TGT AAA GAT AAG AAG TTC AAT GGA AAA 1367
Ile Leu Lys Cys Lys Asp Lys Lys Phe Asn Gly Lys
230 235 240

GGA CCA TGT ACA AAT GTC AGC ACA GTA CAA TGT ACA 1403
Gly Pro Cys Thr Asn Val Ser Thr Val Gln Cys Thr
245 250

CAT GGA ATT AGG CCA GTA GTA TCA ACT CAA CTG CTG 1439

|  |  |  |  |  |  |  |  |  |  |  |
|---|---|---|---|---|---|---|---|---|---|---|
| His | Gly | Ile | Arg | Pro | Val | Val | Ser | Thr | Gln | Leu | Leu |
| 255 |  |  |  |  | 260 |  |  |  |  |  |  |

```
TTA  AAT  GGC  AGT  CTA  GCA  GAA  GAA  GAG  GTA  GTA  ATT       1475
Leu  Asn  Gly  Ser  Leu  Ala  Glu  Glu  Glu  Val  Val  Ile
265                 270                           275

AGA  TCC  GCC  AAT  TTC  GCG  GAC  AAT  GCT  AAA  GTC  ATA       1511
Arg  Ser  Ala  Asn  Phe  Ala  Asp  Asn  Ala  Lys  Val  Ile
280                 285

ATA  GTA  CAG  CTG  AAT  GAA  TCT  GTA  GAA  ATT  AAT  TGT       1547
Ile  Val  Gln  Leu  Asn  Glu  Ser  Val  Glu  Ile  Asn  Cys
290                 295                           300

ACA  AGA  CCC  AAC  AAC  AAT  ACA  AGA  AAA  AGT  ATA  CAT       1583
Thr  Arg  Pro  Asn  Asn  Asn  Thr  Arg  Lys  Ser  Ile  His
305                 310

ATA  GGA  CCA  GGC  AGA  GCA  TTT  TAT  ACA  ACA  GGA  GAA       1619
Ile  Gly  Pro  Gly  Arg  Ala  Phe  Tyr  Thr  Thr  Gly  Glu
315                 320

ATA  ATA  GGA  GAT  ATA  AGA  CAA  GCA  CAT  TGT  AAC  CTT       1655
Ile  Ile  Gly  Asp  Ile  Arg  Gln  Ala  His  Cys  Asn  Leu
325                 330                           335

AGT  AGA  GCA  AAA  TGG  AAT  GAC  ACT  TTA  AAT  AAG  ATA       1691
Ser  Arg  Ala  Lys  Trp  Asn  Asp  Thr  Leu  Asn  Lys  Ile
340                 345

GTT  ATA  AAA  TTA  AGA  GAA  CAA  TTT  GGG  AAT  AAA  ACA       1727
Val  Ile  Lys  Leu  Arg  Glu  Gln  Phe  Gly  Asn  Lys  Thr
350                 355                           360

ATA  GTC  TTT  AAG  CAC  TCC  TCA  GGA  GGG  GAC  CCA  GAA       1763
Ile  Val  Phe  Lys  His  Ser  Ser  Gly  Gly  Asp  Pro  Glu
365                 370

ATT  GTG  ACG  CAC  AGT  TTT  AAT  TGT  GGA  GGG  GAA  TTT       1799
Ile  Val  Thr  His  Ser  Phe  Asn  Cys  Gly  Gly  Glu  Phe
375                 380

TTC  TAC  TGT  AAT  TCA  ACA  CAA  CTG  TTT  AAT  AGT  ACT       1835
Phe  Tyr  Cys  Asn  Ser  Thr  Gln  Leu  Phe  Asn  Ser  Thr
385                 390                           395

TGG  AAT  GTT  ACT  GAA  GAG  TCA  AAT  AAC  ACT  GTA  GAA       1871
Trp  Asn  Val  Thr  Glu  Glu  Ser  Asn  Asn  Thr  Val  Glu
400                 405

AAT  AAC  ACA  ATC  ACA  CTC  CCA  TGC  AGA  ATA  AAA  CAA       1907
Asn  Asn  Thr  Ile  Thr  Leu  Pro  Cys  Arg  Ile  Lys  Gln
410                 415                           420

ATT  ATA  AAC  ATG  TGG  CAG  GAA  GTA  GGA  AGA  GCA  ATG       1943
Ile  Ile  Asn  Met  Trp  Gln  Glu  Val  Gly  Arg  Ala  Met
425                 430

TAT  GCC  CCT  CCC  ATC  AGA  GGA  CAA  ATT  AGA  TGT  TCA       1979
Tyr  Ala  Pro  Pro  Ile  Arg  Gly  Gln  Ile  Arg  Cys  Ser
435                 440

TCA  AAT  ATT  ACA  GGG  CTG  CTA  TTA  ACA  AGA  GAT  GGT       2015
Ser  Asn  Ile  Thr  Gly  Leu  Leu  Leu  Thr  Arg  Asp  Gly
445                 450                           455

GGT  CCT  GAG  GAC  AAC  AAG  ACC  GAG  GTC  TTC  AGA  CCT       2051
Gly  Pro  Glu  Asp  Asn  Lys  Thr  Glu  Val  Phe  Arg  Pro
460                 465

GGA  GGA  GGA  GAT  ATG  AGG  GAT  AAT  TGG  AGA  AGT  GAA       2087
Gly  Gly  Gly  Asp  Met  Arg  Asp  Asn  Trp  Arg  Ser  Glu
470                 475                           480

TTA  TAT  AAA  TAT  AAA  GTA  GTA  AAA  ATT  GAA  CCA  TTA       2123
Leu  Tyr  Lys  Tyr  Lys  Val  Val  Lys  Ile  Glu  Pro  Leu
485                 490

GGA  GTA  GCA  CCC  ACC  AAG  GCA  AAG  AGA  AGA  GTG  GTG       2159
```

```
      Gly  Val  Ala  Pro  Thr  Lys  Ala  Lys  Arg  Arg  Val  Val
      495                 500

CAG   AGA  GAA  AAA  AGA  GCA  GTG  GGA  ATA  GGA  GCT  GTG            2195
Gln   Arg  Glu  Lys  Arg  Ala  Val  Gly  Ile  Gly  Ala  Val
505                       510                      515

TTC   CTT  GGG  TTC  TTG  GGA  GCA  GCA  GGA  AGC  ACT  ATG            2231
Phe   Leu  Gly  Phe  Leu  Gly  Ala  Ala  Gly  Ser  Thr  Met
520                       525

GGC   GCA  GCG  GCA  ATG  ACG  CTG  ACG  GTA  CAG  GCC  AGA            2267
Gly   Ala  Ala  Ala  Met  Thr  Leu  Thr  Val  Gln  Ala  Arg
530                       535                      540

CTA   TTA  TTG  TCT  GGT  ATA  GTG  CAA  CAG  CAG  AAC  AAT            2303
Leu   Leu  Leu  Ser  Gly  Ile  Val  Gln  Gln  Gln  Asn  Asn
545                       550

CTG   CTG  AGG  GCT  ATT  GAG  GCG  CAA  CAG  CAT  CTG  TTG            2339
Leu   Leu  Arg  Ala  Ile  Glu  Ala  Gln  Gln  His  Leu  Leu
555                       560

CAA   CTC  ACA  GTC  TGG  GGC  ATC  AAG  CAG  CTC  CAG  GCA            2375
Gln   Leu  Thr  Val  Trp  Gly  Ile  Lys  Gln  Leu  Gln  Ala
565                       570                      575

AGA   GTC  CTG  GCT  GTG  GAA  AGA  TAC  CTA  AGG  GAT  CAA            2411
Arg   Val  Leu  Ala  Val  Glu  Arg  Tyr  Leu  Arg  Asp  Gln
580                       585

CAG   CTC  CTG  GGG  ATT  TGG  GGT  TGC  TCT  GGA  AAA  CTC            2447
Gln   Leu  Leu  Gly  Ile  Trp  Gly  Cys  Ser  Gly  Lys  Leu
590                       595                      600

ATC   TGC  ACC  ACT  GCT  GTG  CCT  TGG  AAT  GCT  AGT  TGG            2483
Ile   Cys  Thr  Thr  Ala  Val  Pro  Trp  Asn  Ala  Ser  Trp
605                       610

AGT   AAT  AAA  TCT  CTG  AAT  AAG  ATT  TGG  GAT  AAC  ATG            2519
Ser   Asn  Lys  Ser  Leu  Asn  Lys  Ile  Trp  Asp  Asn  Met
615                       620

ACC   TGG  ATA  GAG  TGG  GAC  AGA  GAA  ATT  AAC  AAT  TAC            2555
Thr   Trp  Ile  Glu  Trp  Asp  Arg  Glu  Ile  Asn  Asn  Tyr
625                       630                      635

ACA   AGC  ATA  ATA  TAC  AGC  TTA  ATT  GAA  GAA  TCG  CAG            2591
Thr   Ser  Ile  Ile  Tyr  Ser  Leu  Ile  Glu  Glu  Ser  Gln
640                       645

AAC   CAA  CAA  GAA  AAG  AAT  GAA  CAA  GAA  TTA  TTA  GAA            2627
Asn   Gln  Gln  Glu  Lys  Asn  Glu  Gln  Glu  Leu  Leu  Glu
650                       655                      660

TTA   GAT  AAA  TGG  GCA  AGT  TTG  TGG  AAT  TGG  TTT  GAC            2663
Leu   Asp  Lys  Trp  Ala  Ser  Leu  Trp  Asn  Trp  Phe  Asp
665                       670

ATA   ACA  AAA  TGG  CTG  TGG  TAT  ATA  AAA  ATA  TTC  ATA            2699
Ile   Thr  Lys  Trp  Leu  Trp  Tyr  Ile  Lys  Ile  Phe  Ile
675                       680

ATG   ATA  GTA  GGA  GGC  TTG  ATA  GGT  TTA  AGA  ATA  GTT            2735
Met   Ile  Val  Gly  Gly  Leu  Ile  Gly  Leu  Arg  Ile  Val
685                       690                      695

TTT   TCT  GTA  CTT  TCT  ATA  GTG  AAT  AGA  GTT  AGG  CAG            2771
Phe   Ser  Val  Leu  Ser  Ile  Val  Asn  Arg  Val  Arg  Gln
700                       705

GGA   TAC  TCA  CCA  TTA  TCG  TTT  CAG  ACC  CAC  CTC  CCA            2807
Gly   Tyr  Ser  Pro  Leu  Ser  Phe  Gln  Thr  His  Leu  Pro
710                       715                      720

TCC   TCG  AGG  GGA  CCC  GAC  AGG  CCC  GGA  GGA  ATC  GAA            2843
Ser   Ser  Arg  Gly  Pro  Asp  Arg  Pro  Gly  Gly  Ile  Glu
725                       730

GAA   GAA  GGT  GGA  GAG  AGA  GAC  AGA  GAC  AGA  TCC  GGT            2879
```

|  |  |  |  |  |  |  |  |  |  |  |
|---|---|---|---|---|---|---|---|---|---|---|
| Glu | Glu | Gly | Gly | Glu | Arg | Asp | Arg | Asp | Arg | Ser | Gly |
| 735 |  |  |  |  | 740 |  |  |  |  |  |

| CCA | TTA | GTG | AAC | GGA | TTC | TTG | GCG | CTT | ATC | TGG | GTC | 2915 |
| Pro | Leu | Val | Asn | Gly | Phe | Leu | Ala | Leu | Ile | Trp | Val |  |
| 745 |  |  |  | 750 |  |  |  |  | 755 |  |  |  |

| GAT | CTG | CGG | AGC | CTG | TTC | CTC | TTC | AGC | TAC | CAC | CGC | 2951 |
| Asp | Leu | Arg | Ser | Leu | Phe | Leu | Phe | Ser | Tyr | His | Arg |  |
| 760 |  |  |  |  | 765 |  |  |  |  |  |  |  |

| TTG | AGA | GAC | TTA | CTC | TTG | ATT | GTG | ATG | AGG | ATT | GTG | 2987 |
| Leu | Arg | Asp | Leu | Leu | Leu | Ile | Val | Met | Arg | Ile | Val |  |
| 770 |  |  |  |  | 775 |  |  |  |  | 780 |  |  |

| GAA | CTT | CTG | GGA | CTA | GCA | GGG | GGG | TGG | GAA | GTC | CTC | 3023 |
| Glu | Leu | Leu | Gly | Leu | Ala | Gly | Gly | Trp | Glu | Val | Leu |  |
| 785 |  |  |  |  | 790 |  |  |  |  |  |  |  |

| AAA | TAT | TGG | TGG | AAT | CTC | CTA | CAG | TAT | TGG | AGT | CAG | 3059 |
| Lys | Tyr | Trp | Trp | Asn | Leu | Leu | Gln | Tyr | Trp | Ser | Gln |  |
| 795 |  |  |  |  | 800 |  |  |  |  |  |  |  |

| GAA | CTA | AAG | AAT | AGT | GCT | GTT | AGC | TTG | CTC | AAT | GCC | 3095 |
| Glu | Leu | Lys | Asn | Ser | Ala | Val | Ser | Leu | Leu | Asn | Ala |  |
| 805 |  |  |  |  | 810 |  |  |  |  | 815 |  |  |

| ACA | GCT | GTA | GCA | GTA | GCT | GAA | GGG | ACA | GAT | AGG | GTT | 3131 |
| Thr | Ala | Val | Ala | Val | Ala | Glu | Gly | Thr | Asp | Arg | Val |  |
| 820 |  |  |  |  | 825 |  |  |  |  |  |  |  |

| ATA | GAA | GTA | TTA | CAG | AGA | GCT | GTT | AGA | GCT | ATT | CTC | 3167 |
| Ile | Glu | Val | Leu | Gln | Arg | Ala | Val | Arg | Ala | Ile | Leu |  |
| 830 |  |  |  |  | 835 |  |  |  |  | 840 |  |  |

| CAC | ATA | CCT | AGA | AGA | ATA | AGA | CAG | GGC | TTG | GAA | AGG | 3203 |
| His | Ile | Pro | Arg | Arg | Ile | Arg | Gln | Gly | Leu | Glu | Arg |  |
| 845 |  |  |  |  | 850 |  |  |  |  |  |  |  |

| GCT | TTG | CTA |  |  |  |  |  |  |  |  |  | 3212 |
| Ala | Leu | Leu |  |  |  |  |  |  |  |  |  |  |
| 855 |  |  |  |  |  |  |  |  |  |  |  |  |

| TAAGATGGGT | GGCAAGTGGT | CAAAAAGTAG | TATAGTCGTA | 3252 |
| TGGCCTGCTG | TAAGGAAAAG | AATGAGAAGA | ACTGAGCCAG | 3292 |
| CAGCAGATGG | AGTAGGAGCA | GTATCTAGAG | ACCTGGAAAA | 3332 |
| ACATGGAGCA | ATCACAAGTA | GCAATACAGC | AGCTAACAAT | 3372 |
| GCTGATTGTG | CCTGGCTAGA | AGCACAAGAG | GATGAAGAAG | 3412 |
| TGGGTTTTCC | AGTCAGACCT | CAGGTACCTT | TAAGACCAAT | 3452 |
| GACTCGCAGT | GCAGCTATAG | ATCTTAGCCA | CTTTTTTAAG | 3492 |
| AAAAAGGGGG | GACTGGAAGG | GCTAATTCAC | TCCCAAAAAA | 3532 |
| GACAAGATAT | CCTTGATTTG | TGGGTCTACC | ACACACAAGG | 3572 |
| CTACTTCCCT | GATTGGCAGA | ACTACACACC | AGGGCCAGGG | 3612 |
| ACCAGATTTC | CACTGACCTT | TGGATGGTGC | TTCAAGCTAG | 3652 |
| TACCAGTTGA | GCCAGAGAAG | GTAGAAGAGG | CCAATGAAGG | 3692 |
| AGAGAACAAC | TGCTTGTCAC | ACCCTATGAG | CCTGCATGGG | 3732 |
| ATGGATGACC | CGGAGAAAGA | AGTGTTAGCA | TGGAAGTTTG | 3772 |
| ACAGCAGCCT | AGCATTCCAT | CACGTGGCCC | GAGAA | 3807 |

( 2 ) INFORMATION FOR SEQ ID NO:6:

( i ) SEQUENCE CHARACTERISTICS:
        ( A ) LENGTH: 855 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Arg | Val | Thr | Glu | Ile | Arg | Lys | Ser | Tyr | Gln | His |
|-----|-----|-----|-----|-----|-----|-----|-----|-----|-----|-----|-----|
| 1   |     |     |     | 5   |     |     |     |     | 10  |     |     |

| Trp | Trp | Arg | Trp | Gly | Ile | Met | Leu | Leu | Gly | Ile | Leu |
| 15  |     |     |     |     | 20  |     |     |     |     |     |     |

| Met | Ile | Cys | Asn | Ala | Glu | Lys | Leu | Trp | Val | Thr |
| 25  |     |     |     |     | 30  |     |     |     | 35  |     |

| Val | Tyr | Tyr | Gly | Val | Pro | Val | Trp | Lys | Glu | Ala | Thr |
| 40  |     |     |     |     | 45  |     |     |     |     |     |     |

| Thr | Thr | Leu | Phe | Cys | Ala | Ser | Asp | Arg | Lys | Ala | Tyr |
| 50  |     |     |     |     | 55  |     |     |     |     | 60  |     |

| Asp | Thr | Glu | Val | His | Asn | Val | Trp | Ala | Thr | His | Ala |
| 65  |     |     |     |     | 70  |     |     |     |     |     |     |

| Cys | Val | Pro | Thr | Asp | Pro | Asn | Pro | Gln | Glu | Val | Glu |
| 75  |     |     |     |     | 80  |     |     |     |     |     |     |

| Leu | Lys | Asn | Val | Thr | Glu | Asn | Phe | Asn | Met | Trp | Lys |
| 85  |     |     |     |     | 90  |     |     |     |     | 95  |     |

| Asn | Asn | Met | Val | Glu | Gln | Met | His | Glu | Asp | Ile | Ile |
| 100 |     |     |     |     | 105 |     |     |     |     |     |     |

| Ser | Leu | Trp | Asp | Gln | Ser | Leu | Lys | Pro | Cys | Val | Lys |
| 110 |     |     |     |     | 115 |     |     |     |     | 120 |     |

| Leu | Thr | Pro | Leu | Cys | Val | Thr | Leu | Asn | Cys | Thr | Asp |
| 125 |     |     |     |     | 130 |     |     |     |     |     |     |

| Leu | Arg | Asn | Ala | Thr | Asn | Gly | Asn | Asp | Thr | Asn | Thr |
| 135 |     |     |     |     | 140 |     |     |     |     |     |     |

| Thr | Ser | Ser | Ser | Arg | Gly | Met | Val | Gly | Gly | Gly | Glu |
| 145 |     |     |     |     | 150 |     |     |     |     | 155 |     |

| Met | Lys | Asn | Cys | Ser | Phe | Asn | Ile | Thr | Thr | Asn | Ile |
| 160 |     |     |     |     | 165 |     |     |     |     |     |     |

| Arg | Gly | Lys | Val | Gln | Lys | Glu | Tyr | Ala | Leu | Phe | Tyr |
| 170 |     |     |     |     | 175 |     |     |     |     | 180 |     |

| Lys | Leu | Asp | Ile | Ala | Pro | Ile | Asp | Asn | Asn | Ser | Asn |
| 185 |     |     |     |     | 190 |     |     |     |     |     |     |

| Asn | Arg | Tyr | Arg | Leu | Ile | Ser | Cys | Asn | Thr | Ser | Val |
| 195 |     |     |     |     | 200 |     |     |     |     |     |     |

| Ile | Thr | Gln | Ala | Cys | Pro | Lys | Val | Ser | Phe | Glu | Pro |
| 205 |     |     |     |     | 210 |     |     |     |     | 215 |     |

| Ile | Pro | Ile | His | Tyr | Cys | Ala | Pro | Ala | Gly | Phe | Ala |
| 220 |     |     |     |     | 225 |     |     |     |     |     |     |

| Ile | Leu | Lys | Cys | Lys | Asp | Lys | Lys | Phe | Asn | Gly | Lys |
| 230 |     |     |     |     | 235 |     |     |     |     | 240 |     |

| Gly | Pro | Cys | Thr | Asn | Val | Ser | Thr | Val | Gln | Cys | Thr |
| 245 |     |     |     |     | 250 |     |     |     |     |     |     |

| His | Gly | Ile | Arg | Pro | Val | Val | Ser | Thr | Gln | Leu | Leu |
| 255 |     |     |     |     | 260 |     |     |     |     |     |     |

| Leu | Asn | Gly | Ser | Leu | Ala | Glu | Glu | Glu | Val | Val | Ile |
| 265 |     |     |     |     | 270 |     |     |     |     | 275 |     |

| Arg | Ser | Ala | Asn | Phe | Ala | Asp | Asn | Ala | Lys | Val | Ile |
| 280 |     |     |     |     | 285 |     |     |     |     |     |     |

| Ile | Val | Gln | Leu | Asn | Glu | Ser | Val | Glu | Ile | Asn | Cys |
| 290 |     |     |     |     | 295 |     |     |     |     | 300 |     |

```
Thr  Arg  Pro  Asn  Asn  Asn  Thr  Arg  Lys  Ser  Ile  His
305            310

Ile  Gly  Pro  Gly  Arg  Ala  Phe  Tyr  Thr  Thr  Gly  Glu
315            320

Ile  Ile  Gly  Asp  Ile  Arg  Gln  Ala  His  Cys  Asn  Leu
325            330                           335

Ser  Arg  Ala  Lys  Trp  Asn  Asp  Thr  Leu  Asn  Lys  Ile
340            345

Val  Ile  Lys  Leu  Arg  Glu  Gln  Phe  Gly  Asn  Lys  Thr
350            355                           360

Ile  Val  Phe  Lys  His  Ser  Ser  Gly  Gly  Asp  Pro  Glu
365            370

Ile  Val  Thr  His  Ser  Phe  Asn  Cys  Gly  Gly  Glu  Phe
375            380

Phe  Tyr  Cys  Asn  Ser  Thr  Gln  Leu  Phe  Asn  Ser  Thr
385            390                           395

Trp  Asn  Val  Thr  Glu  Glu  Ser  Asn  Asn  Thr  Val  Glu
400            405

Asn  Asn  Thr  Ile  Thr  Leu  Pro  Cys  Arg  Ile  Lys  Gln
410            415                           420

Ile  Ile  Asn  Met  Trp  Gln  Glu  Val  Gly  Arg  Ala  Met
425            430

Tyr  Ala  Pro  Pro  Ile  Arg  Gly  Gln  Ile  Arg  Cys  Ser
435            440

Ser  Asn  Ile  Thr  Gly  Leu  Leu  Leu  Thr  Arg  Asp  Gly
445            450                           455

Gly  Pro  Glu  Asp  Asn  Lys  Thr  Glu  Val  Phe  Arg  Pro
460            465

Gly  Gly  Gly  Asp  Met  Arg  Asp  Asn  Trp  Arg  Ser  Glu
470            475                           480

Leu  Tyr  Lys  Tyr  Lys  Val  Val  Lys  Ile  Glu  Pro  Leu
485            490

Gly  Val  Ala  Pro  Thr  Lys  Ala  Lys  Arg  Arg  Val  Val
495            500

Gln  Arg  Glu  Lys  Arg  Ala  Val  Gly  Ile  Gly  Ala  Val
505            510                           515

Phe  Leu  Gly  Phe  Leu  Gly  Ala  Ala  Gly  Ser  Thr  Met
520            525

Gly  Ala  Ala  Ala  Met  Thr  Leu  Thr  Val  Gln  Ala  Arg
530            535                           540

Leu  Leu  Leu  Ser  Gly  Ile  Val  Gln  Gln  Gln  Asn  Asn
545            550

Leu  Leu  Arg  Ala  Ile  Glu  Ala  Gln  Gln  His  Leu  Leu
555            560

Gln  Leu  Thr  Val  Trp  Gly  Ile  Lys  Gln  Leu  Gln  Ala
565            570                           575

Arg  Val  Leu  Ala  Val  Glu  Arg  Tyr  Leu  Arg  Asp  Gln
580            585

Gln  Leu  Leu  Gly  Ile  Trp  Gly  Cys  Ser  Gly  Lys  Leu
590            595                           600

Ile  Cys  Thr  Thr  Ala  Val  Pro  Trp  Asn  Ala  Ser  Trp
605            610

Ser  Asn  Lys  Ser  Leu  Asn  Lys  Ile  Trp  Asp  Asn  Met
615            620
```

-continued

```
Thr  Trp  Ile  Glu  Trp  Asp  Arg  Glu  Ile  Asn  Asn  Tyr
625                      630                      635

Thr  Ser  Ile  Ile  Tyr  Ser  Leu  Ile  Glu  Glu  Ser  Gln
640                      645

Asn  Gln  Gln  Glu  Lys  Asn  Glu  Gln  Glu  Leu  Leu  Glu
650                      655                           660

Leu  Asp  Lys  Trp  Ala  Ser  Leu  Trp  Asn  Trp  Phe  Asp
665                      670

Ile  Thr  Lys  Trp  Leu  Trp  Tyr  Ile  Lys  Ile  Phe  Ile
675                      680

Met  Ile  Val  Gly  Gly  Leu  Ile  Gly  Leu  Arg  Ile  Val
685                      690                           695

Phe  Ser  Val  Leu  Ser  Ile  Val  Asn  Arg  Val  Arg  Gln
700                      705

Gly  Tyr  Ser  Pro  Leu  Ser  Phe  Gln  Thr  His  Leu  Pro
710                      715                           720

Ser  Ser  Arg  Gly  Pro  Asp  Arg  Pro  Gly  Gly  Ile  Glu
725                      730

Glu  Glu  Gly  Gly  Glu  Arg  Asp  Arg  Asp  Arg  Ser  Gly
735                      740

Pro  Leu  Val  Asn  Gly  Phe  Leu  Ala  Leu  Ile  Trp  Val
745                      750                           755

Asp  Leu  Arg  Ser  Leu  Phe  Leu  Phe  Ser  Tyr  His  Arg
760                      765

Leu  Arg  Asp  Leu  Leu  Leu  Ile  Val  Met  Arg  Ile  Val
770                      775                           780

Glu  Leu  Leu  Gly  Leu  Ala  Gly  Gly  Trp  Glu  Val  Leu
785                      790

Lys  Tyr  Trp  Trp  Asn  Leu  Leu  Gln  Tyr  Trp  Ser  Gln
795                      800

Glu  Leu  Lys  Asn  Ser  Ala  Val  Ser  Leu  Leu  Asn  Ala
805                      810                           815

Thr  Ala  Val  Ala  Val  Ala  Glu  Gly  Thr  Asp  Arg  Val
820                      825

Ile  Glu  Val  Leu  Gln  Arg  Ala  Val  Arg  Ala  Ile  Leu
830                      835                           840

His  Ile  Pro  Arg  Arg  Ile  Arg  Gln  Gly  Leu  Glu  Arg
845                      850

Ala  Leu  Leu
855
```